US011806253B2

(12) United States Patent
Mahon et al.

(10) Patent No.: US 11,806,253 B2
(45) Date of Patent: Nov. 7, 2023

(54) LANYARD SYSTEMS FOR PROSTHETIC DEVICES AND RELATED METHODS

(71) Applicant: Click Holdings, LLC, Steamboat Springs, CO (US)

(72) Inventors: Joseph A Mahon, Salt Lake City, UT (US); Nicholas E. Scoville, Salt Lake City, UT (US); Simon T. Scoville, Salt Lake City, UT (US); James A. Capra, Steamboat Springs, CO (US); Arni Thor, San Diego, CA (US)

(73) Assignee: Click Holdings, LLC, Steamboat Springs, CO (US)

( * ) Notice: Subject to any disclaimer, the term of this patent is extended or adjusted under 35 U.S.C. 154(b) by 617 days.

(21) Appl. No.: 16/934,784

(22) Filed: Jul. 21, 2020

(65) Prior Publication Data
US 2020/0345521 A1  Nov. 5, 2020

Related U.S. Application Data

(63) Continuation of application No. 15/284,515, filed on Oct. 3, 2016, now abandoned.
(Continued)

(51) Int. Cl.
*A61F 2/78* (2006.01)
*A61F 2/00* (2006.01)
(Continued)

(52) U.S. Cl.
CPC .............. *A61F 2/78* (2013.01); *A61F 2/0095* (2013.01); *A61F 2/66* (2013.01); *A61F 2/76* (2013.01);
(Continued)

(58) Field of Classification Search
CPC ...... A61F 2002/7831; A61F 2002/5016; A61F 2/78; A61F 2/0095; A61F 2/66;
(Continued)

(56) References Cited

U.S. PATENT DOCUMENTS 5,326,351 A * 7/1994 Sarazin ..................... A61F 2/80
223/111
6,589,289 B2   7/2003 Ingimarsson
(Continued)

FOREIGN PATENT DOCUMENTS

DE   19531070   2/1997
DE   10026399   12/2001
(Continued)

OTHER PUBLICATIONS

Extended European Search Report dated May 17, 2019 for EP application 16852847.9.
(Continued)

*Primary Examiner* — Moshe Wilensky
*Assistant Examiner* — Darrell C Ford
(74) *Attorney, Agent, or Firm* — Dorsey & Whitney LLP

(57) ABSTRACT

A prosthesis device can include a socket or a kit for forming a socket having a lanyard suspension system. In one example, the lanyard suspension system includes a tightening device having a housing, and tightening the lanyard gathers a tensioning line portion of the lanyard into an interior of the housing.

20 Claims, 51 Drawing Sheets

Related U.S. Application Data

(60) Provisional application No. 62/236,852, filed on Oct. 2, 2015.

(51) Int. Cl.
*A61F 2/76* (2006.01)
*A61F 2/50* (2006.01)
*A61F 2/80* (2006.01)
*A61F 2/66* (2006.01)

(52) U.S. Cl.
CPC ......... *A61F 2/80* (2013.01); *A61F 2002/5056* (2013.01); *A61F 2002/7831* (2013.01); *A61F 2002/802* (2013.01); *Y10T 29/49863* (2015.01)

(58) Field of Classification Search
CPC ...... A61F 2/76; A61F 2/80; A61F 2002/5056; A61F 2002/802; A61B 2017/0496; Y10T 29/49863
See application file for complete search history.

(56) References Cited

U.S. PATENT DOCUMENTS

| | | | |
|---|---|---|---|
| 6,793,682 B1 * | 9/2004 | Mantelmacher | A61F 2/7812 623/36 |
| 6,797,008 B1 | 9/2004 | Arbogast et al. | |
| 7,537,199 B1 | 5/2009 | Anderson | |
| 8,641,779 B1 * | 2/2014 | Hollard | A61F 2/7812 623/36 |
| 2005/0209706 A1 * | 9/2005 | Warila | A61F 2/78 623/36 |
| 2005/0256589 A1 | 11/2005 | Slemker et al. | |
| 2008/0243266 A1 | 10/2008 | Haynes et al. | |
| 2010/0121464 A1 * | 5/2010 | Mantelmacher | A61F 2/78 623/33 |
| 2011/0071647 A1 | 3/2011 | Mahon | |
| 2013/0123940 A1 | 5/2013 | Hurley et al. | |
| 2014/0359981 A1 | 12/2014 | Cotterman et al. | |
| 2015/0289999 A1 * | 10/2015 | Radspieler | A61F 2/7812 623/34 |
| 2017/0151072 A1 | 6/2017 | Mahon et al. | |

FOREIGN PATENT DOCUMENTS

| | | |
|---|---|---|
| WO | 2014075808 | 5/2014 |
| WO | 2014197236 | 12/2014 |

OTHER PUBLICATIONS

Mahon, Joseph A., International Search Report and Written Opinion dated Dec. 15, 2016 for PCT/US2016/055211.
Mahon, et al., Office Action dated Feb. 21, 2018 for U.S. Appl. No. 15/284,515.
Mahon, et al., Office Action dated Jun. 24, 2019 for U.S. Appl. No. 15/284,515.
Mahon, et al., Office Action dated Mar. 9, 2020 for U.S. Appl. No. 15/284,515.
Mahon, et al., Office Action dated Oct. 9, 2018 for U.S. Appl. No. 15/284,515.

* cited by examiner

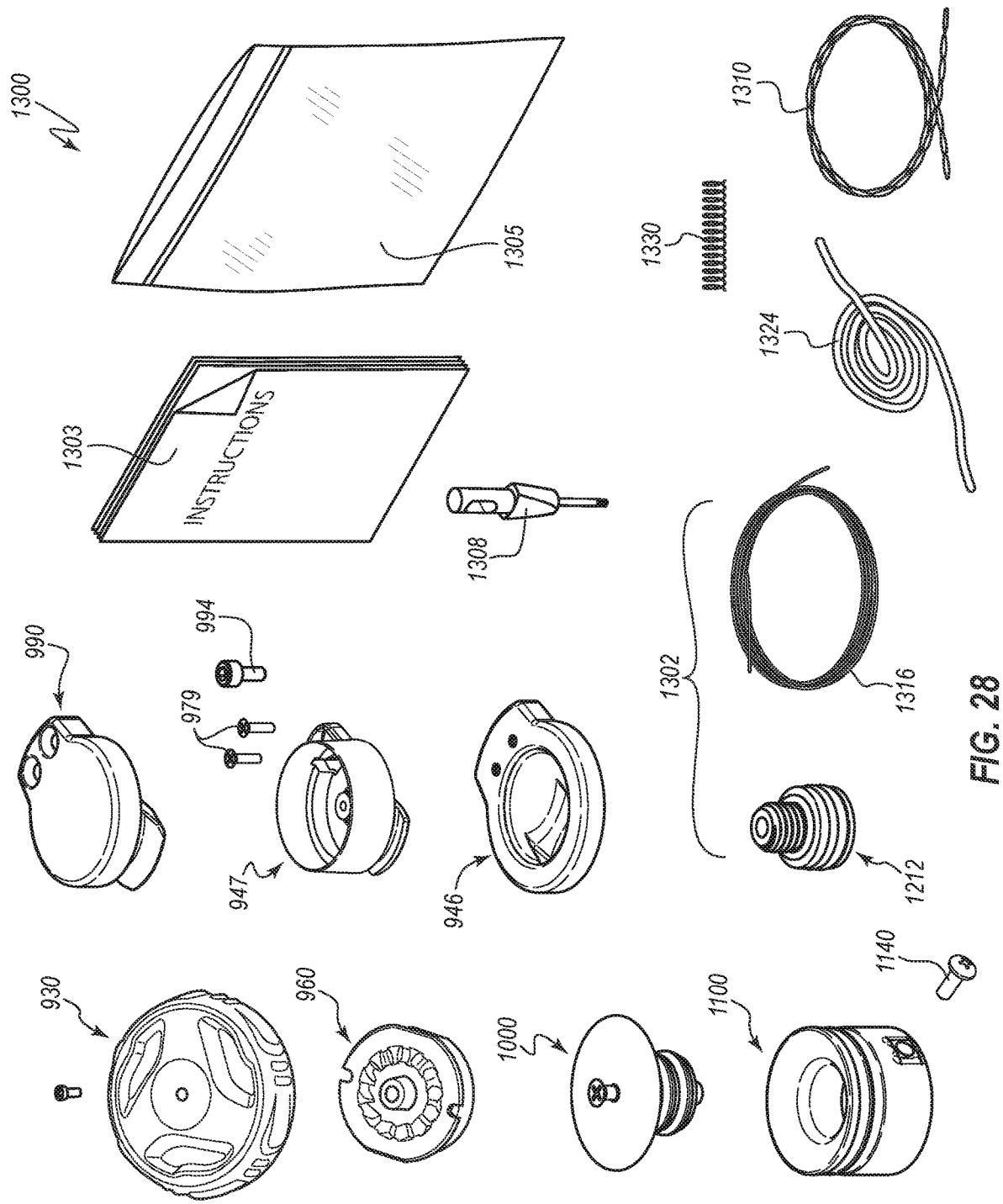

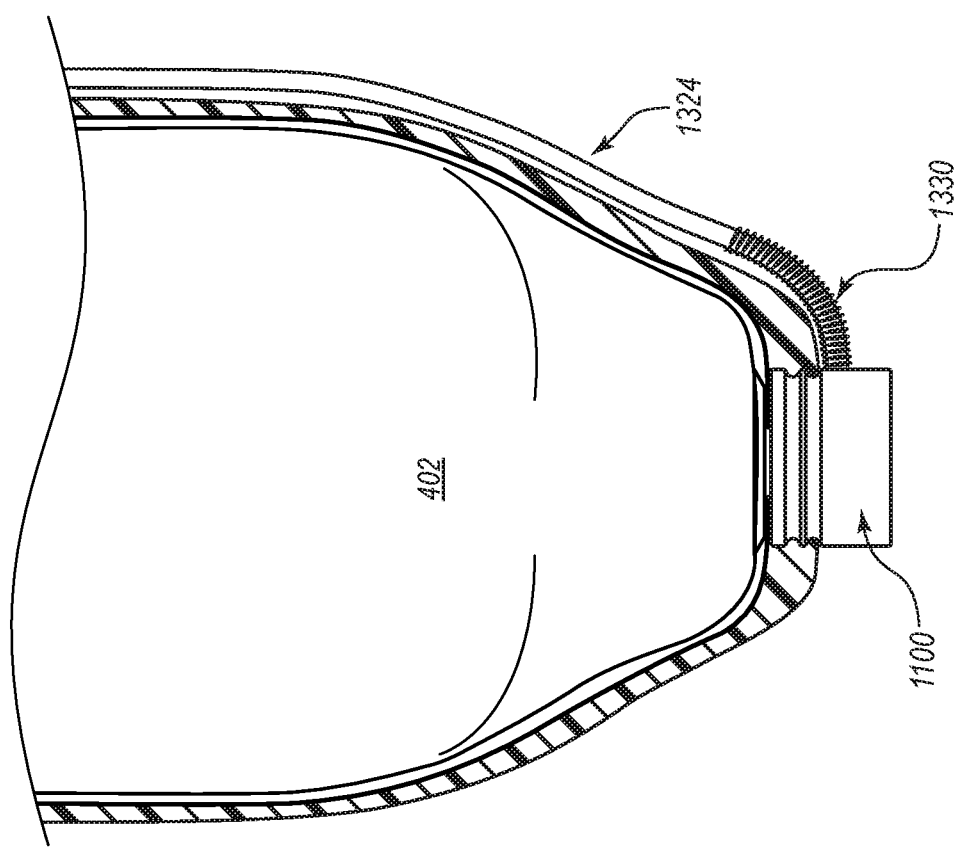

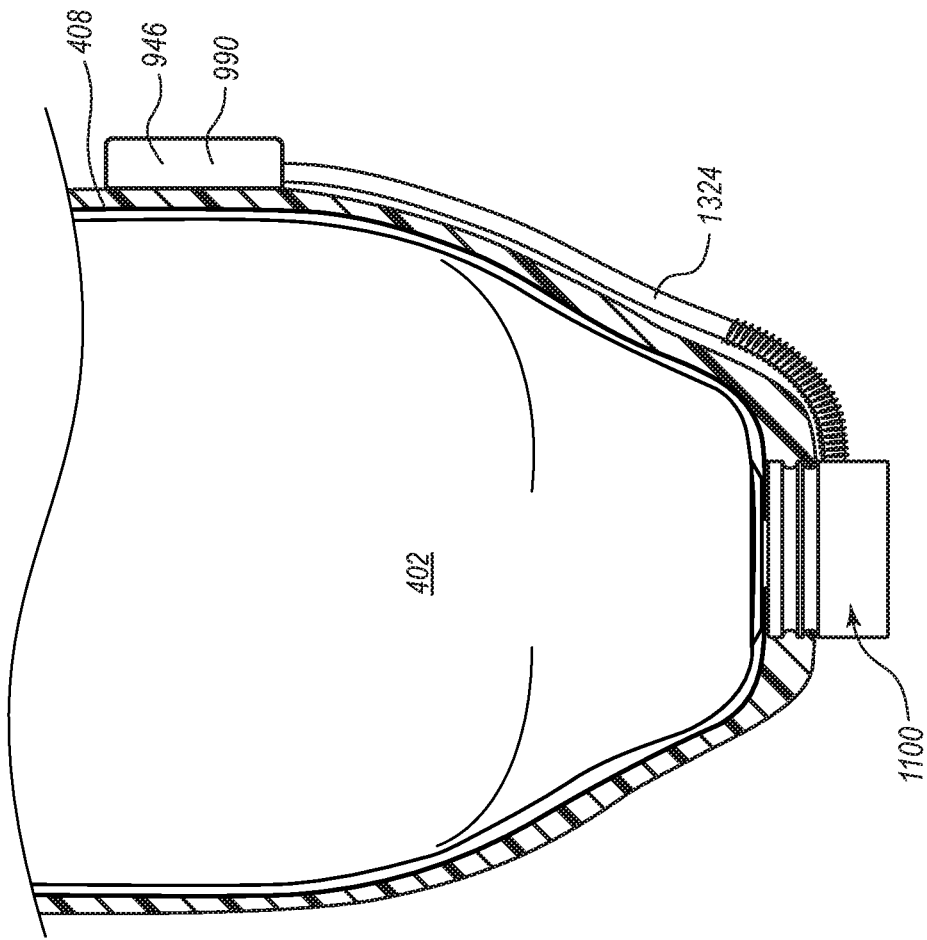
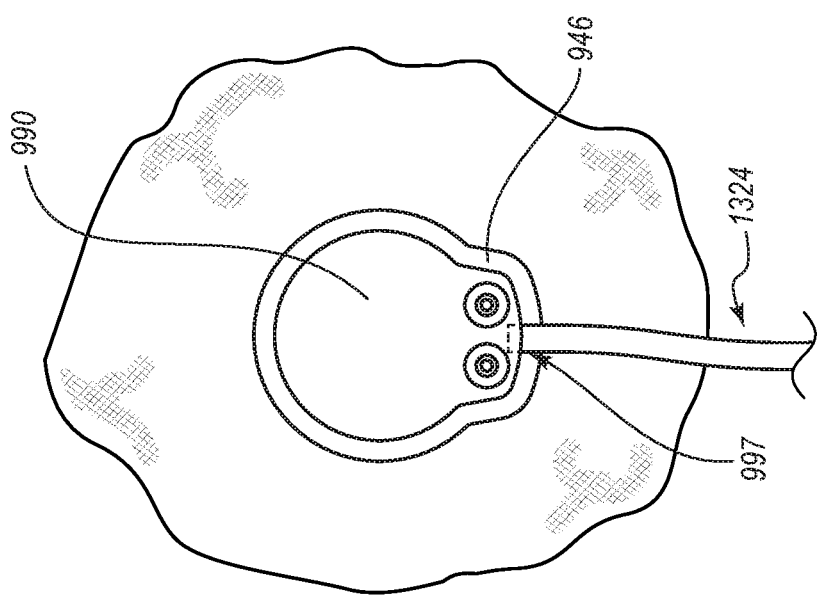

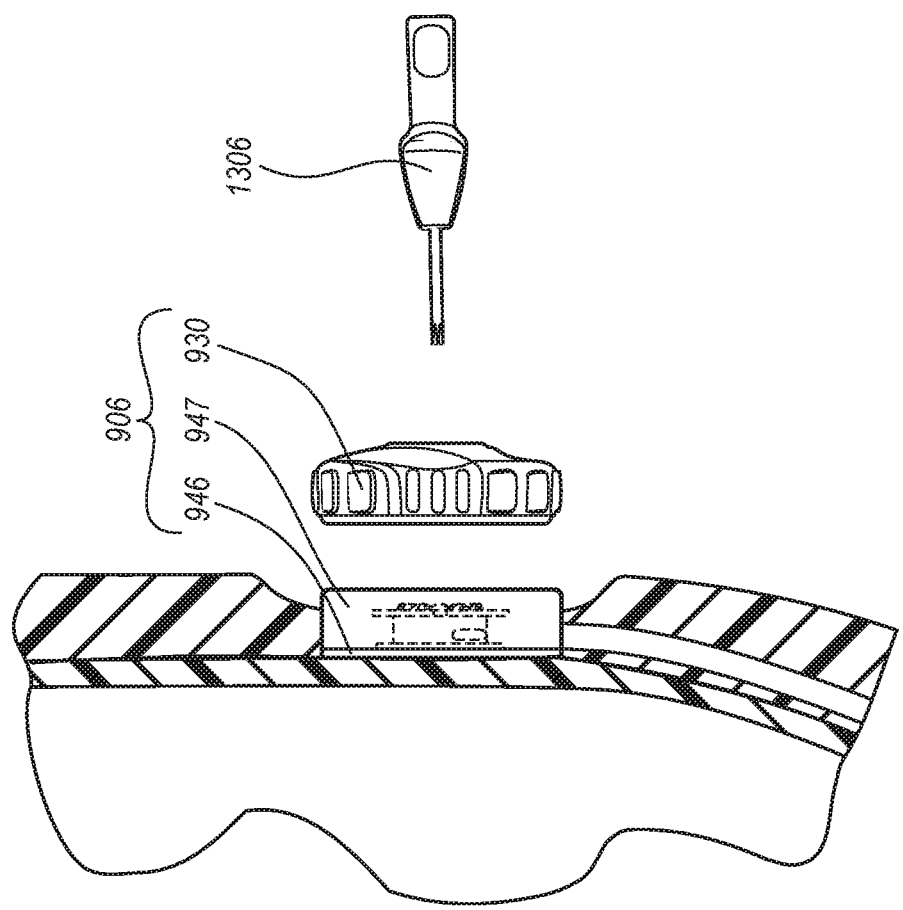

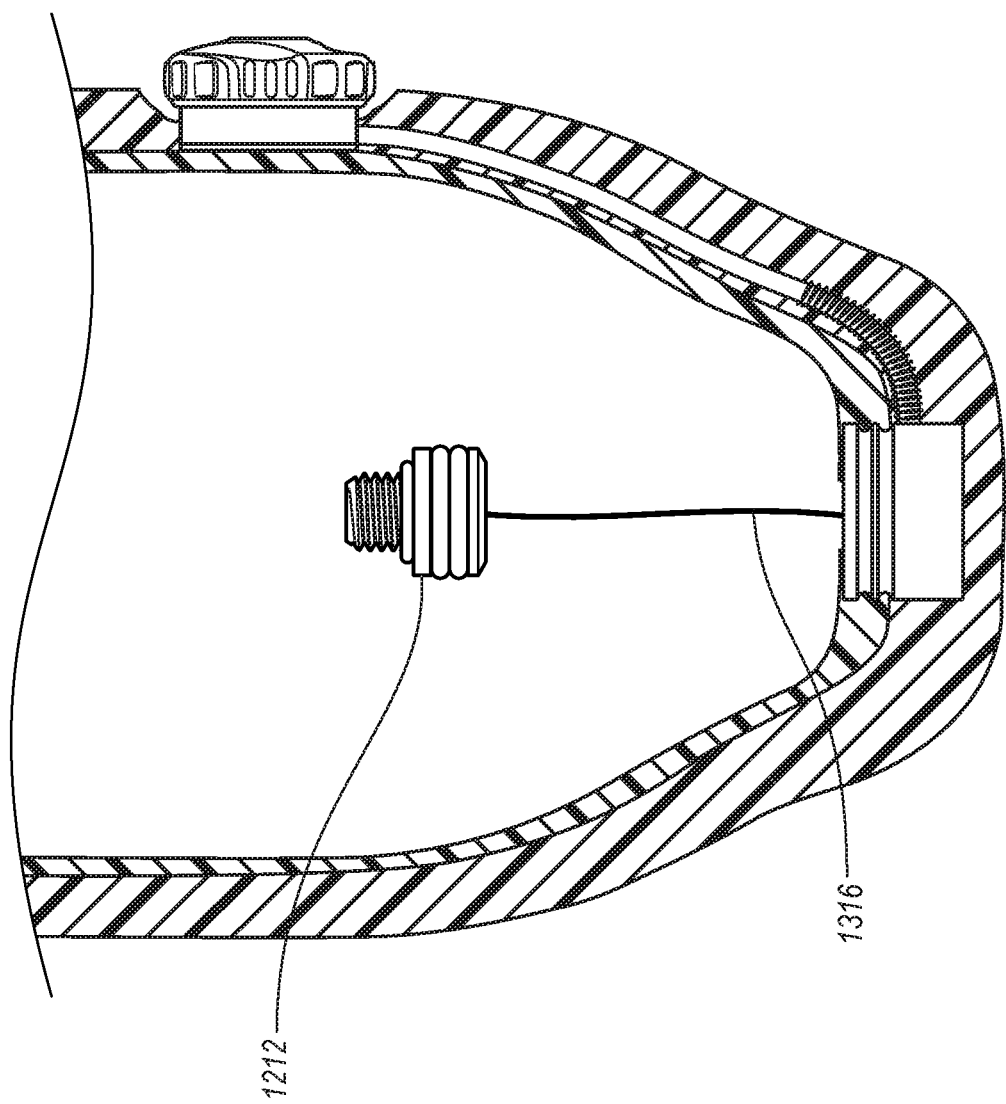

LANYARD SYSTEMS FOR PROSTHETIC DEVICES AND RELATED METHODS

CROSS-REFERENCE TO RELATED APPLICATIONS

This application is a continuation of U.S. patent application Ser. No. 15/284,515, titled LANYARD SYSTEMS FOR PROSTHETIC DEVICES AND RELATED METHODS, which was filed on Oct. 3, 2016, which claims the benefit under 35 U.S.C. § 119(e) of U.S. Provisional Patent Application No. 62/236,852, titled LANYARD SYSTEMS FOR PROSTHETIC DEVICES AND RELATED METHODS, which was filed on Oct. 2, 2015, the entire contents of each of which are hereby incorporated by reference herein.

TECHNICAL FIELD

The present disclosure relates to prosthetic devices and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 18A illustrates placement of a base and a dummy in a coupled state at a desired position during a layup procedure;

FIG. 18B shows that another layer of one or more materials may be provided over the base, the dummy, and the conduit such that those items are sandwiched therebetween;

FIG. 18C illustrates the introduction of liquid resin about the base, the dummy, and the conduit;

FIG. 18D shows the hardened or cured resin and the barrier layers removed;

FIG. 18E shows a portion of the resin removed from above the dummy;

FIG. 18F shows a stage after removal of the dummy to expose the cavity of the base;

FIG. 18G shows the knob coupled to the base;

FIG. 28 is a perspective view of an embodiment of a kit that is configured to be used in the manufacture of a socket;

FIG. 29A is an elevation view of the post mounted to a distal end of a mold or model of a residuum;

FIG. 29H is an elevation view such as that of FIG. 29C that depicts the conduit having been cut to a desired length;

FIG. 29I is a detailed elevation view that omits certain features depicted in FIG. 29H and shows the proximal end of the conduit being coupled with a dummy, wherein the dummy is coupled with a base mounting plate;

FIG. 29J is an elevation view such as that of FIG. 29C that depicts the mounting-plate-and-dummy assembly coupled to an outer layer of material that has been laid up on the model, wherein the proximal end of the conduit is coupled with the dummy;

FIG. 29T is an elevation view similar to that of FIG. 29C depicting the coupling of an actuator to the reel housing;

FIG. 29U is an elevation view similar to that of FIG. 29C depicting the coupling of a connector to the tensioning line;

FIG. 29V is a cross-sectional view of a distal end of the socket that depicts the connector having been drawn into the lanyard housing;

DETAILED DESCRIPTION

Figure 1:
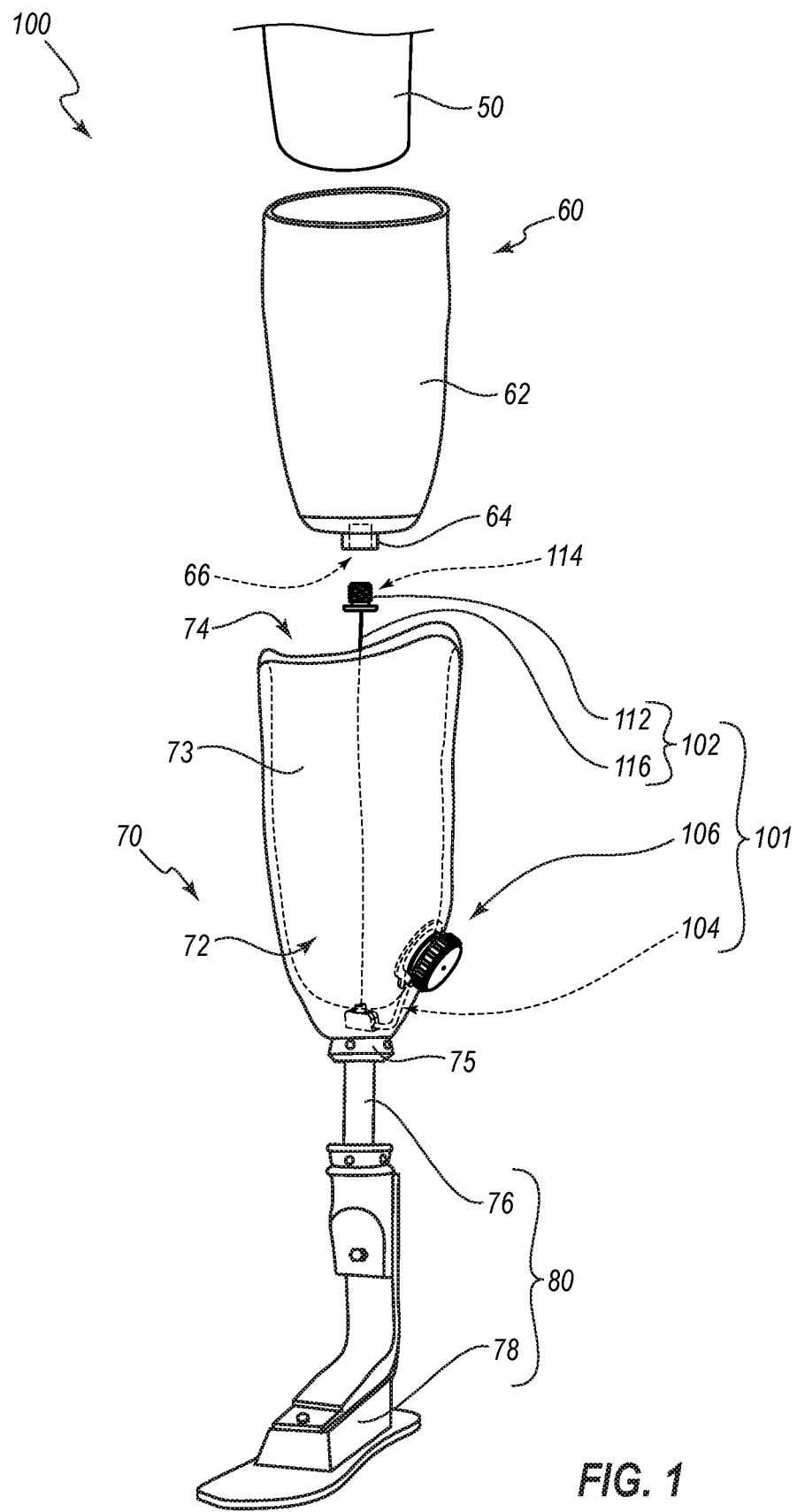
FIG. 1 is an exploded perspective view of an embodiment of a prosthetic system for use with a residuum, the prosthetic system including an embodiment of a socket having an embodiment of a lanyard suspension system.

Various embodiments of lanyard suspension systems for prosthetic devices are described herein. An example of one such embodiment is depicted in FIGS. 1-5, which is discussed in detail below. Methods for fabricating sockets into which the lanyard suspension systems are incorporated, methods for using the lanyard suspension systems, and kits for use in fabricating the sockets are also disclosed. In certain embodiments, a lanyard suspension system includes a lanyard that is configured to be selectively coupled with a liner that interfaces with a residual limb (or "residuum") of an amputee. The system defines a pathway that extends from a distal end of a cavity defined by the socket, through a wall of the socket, to a tightening mechanism that is capable of being actuated from an exterior of the socket. A tensioning line of a lanyard extends through the pathway and is coupled to the tightening mechanism. In certain embodiments, the tightening mechanism can be located at any position at an exterior of the socket, which can facilitate use of the suspension system. In other or further embodiments, the tightening mechanism can gather the tensioning line of the lanyard into an interior space defined by the tightening mechanism, thus advantageously hiding the drawn tensioning line from view and/or protecting the tensioning line from weathering, snagging, etc. In other or further embodiments, the tightening mechanism can distribute forces that arise due to tensioning of the tension line into the socket wall as the tensioning line is being tightened, which can facilitate the tightening process for a user. Other or further features and advantages of the various embodiments described herein will be evident from the disclosure that follows.

For the sake of convenience, much of the following disclosure is directed to prosthetic devices that are configured for use with residual portions of an amputated leg, such as a leg that has undergone a transfemoral (i.e., above-knee) or transtibial (i.e., below-knee) amputation. It should be appreciated that the disclosure is also applicable to other prosthetic devices, such as, for example, those configured for use with the residuum of an amputated arm (e.g., after an above-elbow or below-elbow amputation).

The use of transtibial prostheses by transtibial amputees is generally well known. Transtibial prostheses can include a socket, a shank, and a foot-ankle system. A variety of sockets, shanks, and foot-ankle systems are available, which can be combined in any suitable manner to produce a transtibial prosthesis that is tailored to meet the individual needs of different transtibial amputees. The socket generally acts as an interface between the amputee and the prosthesis. The socket can be instrumental in transferring the weight of a transtibial amputee to the ground by the way of the prosthesis. The shank can transfer vertical loads (e.g., at least a portion of the weight of the amputee) to the foot-ankle system, which interfaces with the ground.

A liner is generally used as an interface between the residuum and the socket. A wide variety of suspension systems are known for securing the liner to the socket. Lanyard suspension systems typically include a lanyard that is selectively coupled to the socket and tightened by the user by directly pulling on a tensioning line portion of the lanyard. The user typically must counter substantially all of the tension in the tensioning line while drawing the liner into the socket, which can be difficult for many users. Moreover, in some systems, the user must pull the tensioning line from a distal end of the socket, which can be awkward or difficult. Embodiments disclosed herein can remedy one or more of the foregoing problems and/or other problems of prior lanyard suspension systems, as will be evident from the discussion that follows.

FIG. 1 illustrates an embodiment of a prosthetic system 100 that includes a liner 60 and a prosthetic device 70, which are used with a residuum 50. In particular, the liner 60 is configured to cover and engage the residuum 60. The liner 60 provides an interface between the residuum 50 and the prosthetic device 70. The illustrated liner 60 includes a flexible sleeve 62 for receiving the residuum and a connector 64 for coupling the flexible sleeve 62 with a suspension system. The connector 64 defines a coupling interface 66, which comprises internal threading in the illustrated embodiment. Any other suitable coupling interface is contemplated.

In the illustrated embodiment, the prosthetic device 70 is configured as a substitute for a portion of a right leg of an amputee. The prosthetic device 70 includes a socket 72, which may also be referred to as a receptacle, that comprises a sidewall or wall 73 that defines a cavity 74. The socket 72 can include a support attachment or adapter 75 to which a pylon 76 can be mounted. The pylon 76 can interface with any suitable ankle-foot structure 78. The pylon and/or the ankle-foot structure may be termed more generally as a prosthetic extremity 80, such that the socket 72 can be said to serve as an interface between the residuum and the prosthetic extremity 80. Any suitable arrangement of the prosthetic extremity 80 is possible.

As previously mentioned, the socket 72 can be configured to receive the residuum 50 and the liner 60 within the cavity 74. The socket 72 can be substantially rigid so as to maintain its shape or form when forces are applied thereto, whether from the residuum 50 when it is positioned therein or from compressive forces at an exterior thereof. The term "substantially rigid" is sufficiently broad to cover arrangements where the socket 72 is sufficiently rigid, solid, or firm so as to undergo no change in shape or configuration due to stresses applied thereto by the residuum under normal use (i.e., solid), as well as arrangements where the socket 72 is very rigid, solid, or firm, but is elastically resilient and may undergo slight, non-permanent deformations due to the standard stresses of use (i.e., flexibly firm).

Figure 6:
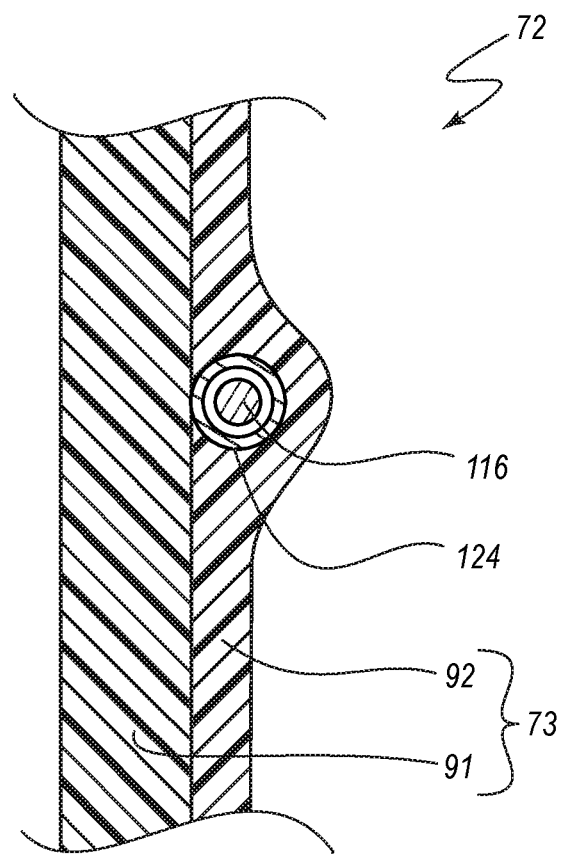
FIG. 6 is a cross-sectional view of a portion of a sidewall of the socket of FIG. 1 taken along the view line 6-6 in FIG. 4.

The wall 73 of the socket 72 can include one or more materials, and may include one or more laminated layers 91, 92 (see FIG. 6). In various embodiments, one or more layers of the wall structure 73 of the socket 72 can include one or more hardened plastic resins (e.g., acrylic, epoxy, polyester). In other or further embodiments, the one or more layers can comprise one or more reinforcement textiles (e.g., fiberglass, nylon, carbon, Nyglass, Dacron®, Kevlar®). Any other suitable materials may be used.

In the illustrated embodiment, the socket 72 comprises a lanyard suspension system 101 that is configured to draw the liner 60 into the socket 72 and retain the liner 60 in the socket 72. The lanyard suspension system 101 comprises a lanyard 102, a guide path 104, and a tightening member 106, which may also be referred to as a tensioning member. In the illustrated embodiment, the lanyard 102 comprises a connector 112 and a tensioning line 116. The connector 112, which may also be referred to as an insert, comprises a coupling interface 114 that is configured to selectively couple with and decouple from the connection interface 66 of the connector 64 portion of the liner 60. In the illustrated embodiment, the connection interface 114 comprises external threading configured to selectively couple with the internal threading of the connector 64. Any suitable connectors 64, 112 and connection interfaces 66, 114 are contemplated.

The connector 112 can be attached to the tensioning line 116 in any suitable manner. In the illustrated embodiment, the connector 112 includes a counterbore 113 sized to retain a knotted end of the tensioning line 116 (see FIG. 3). Any other suitable attachment mechanism is contemplated. The tensioning line 116 can comprise any suitable material, including those commonly known in the art.

Figure 2:
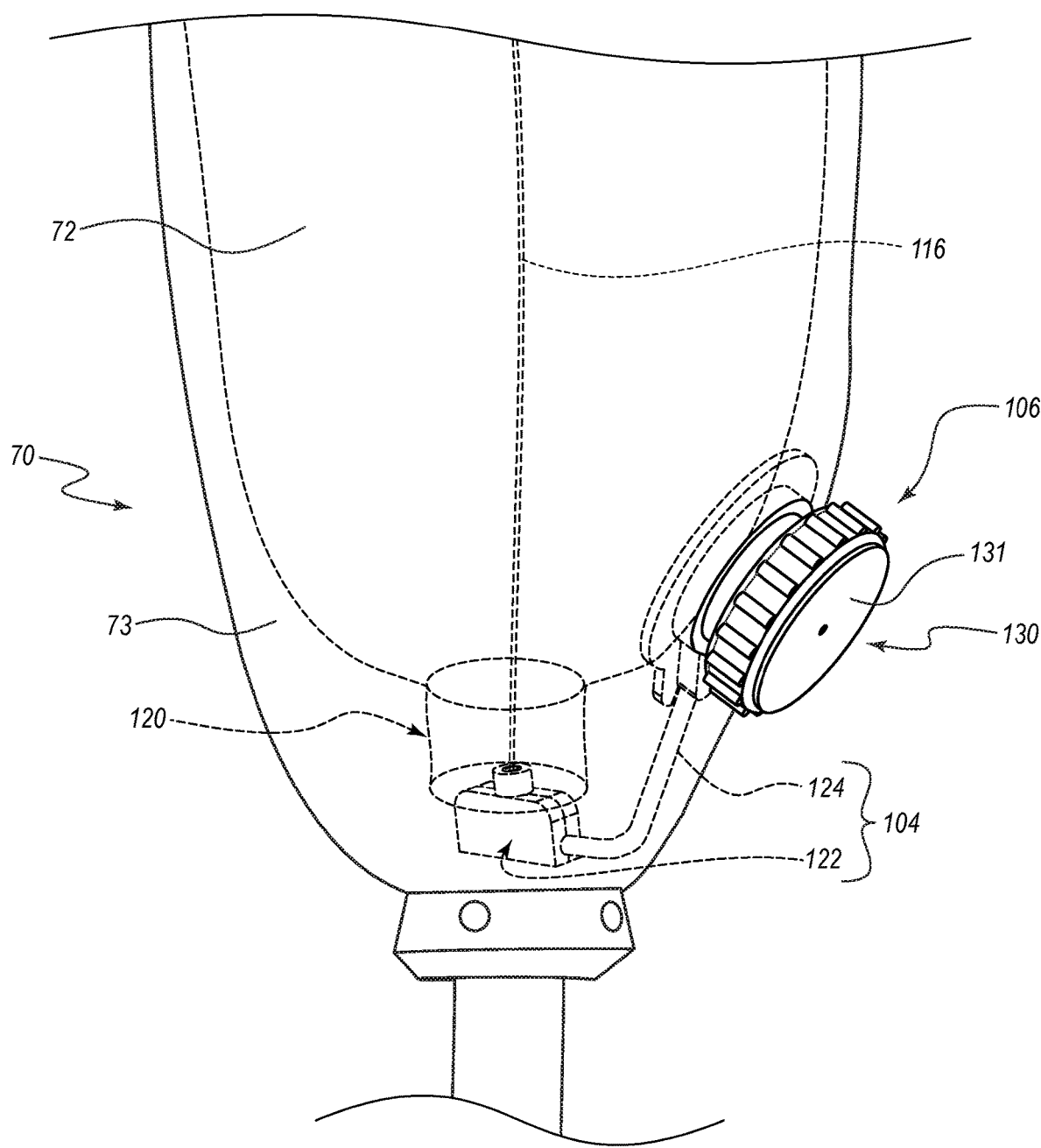
FIG. 2 is an enlarged view of a portion of the prosthetic system of FIG. 1 showing the lanyard suspension system in greater detail.
Figure 3:
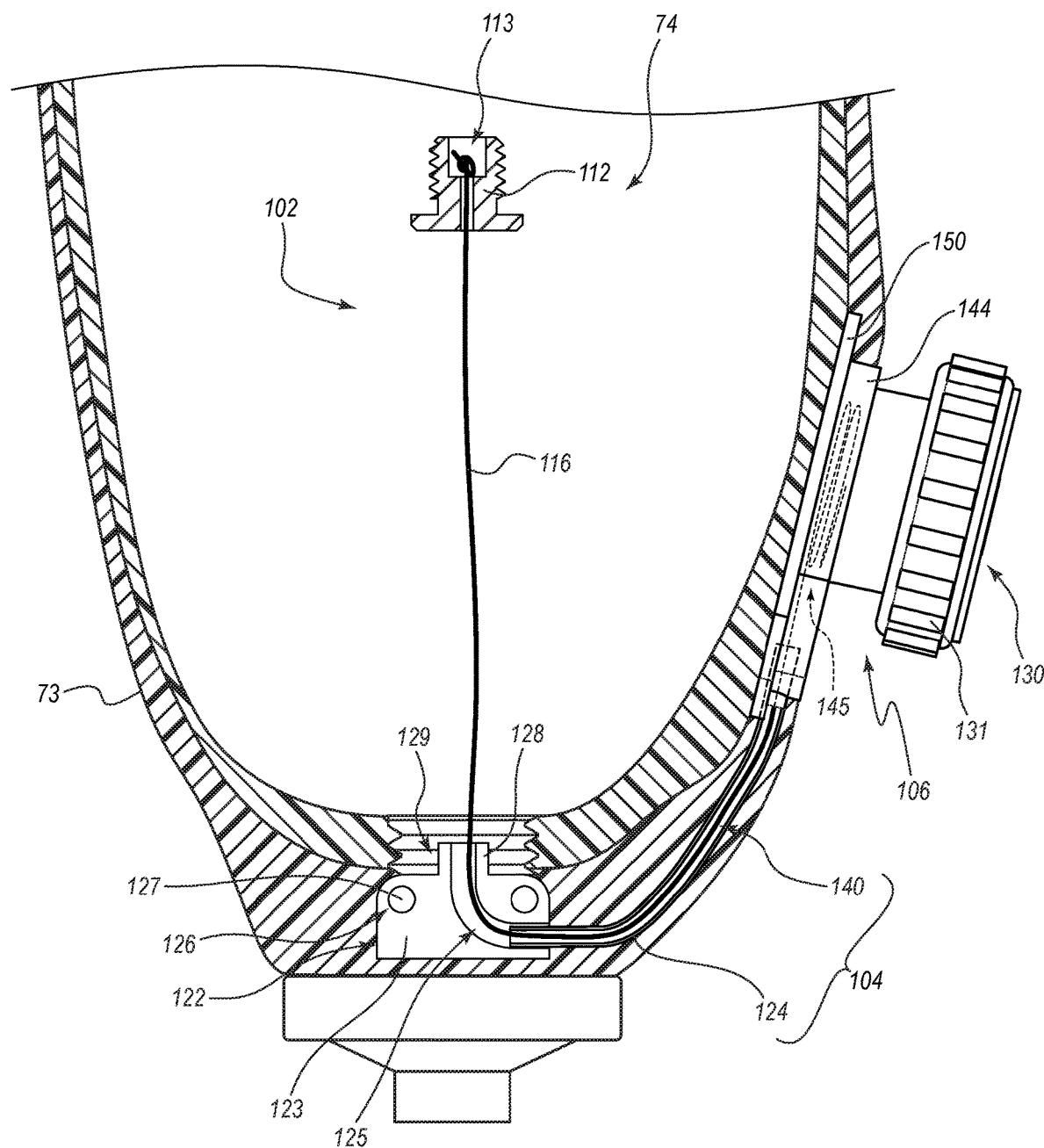
FIG. 3 is a partial cross-sectional view of a distal end of the socket of FIG. 1 showing the lanyard suspension system in further detail and depicting an embodiment of a tightening mechanism, which is shown in a side elevation view, in a tension-release state.

With reference to FIGS. 1-3, the guide path 104 defines a passageway through the wall 73 of the socket 72 such that the tensioning line can extend through the cavity 74 of the socket 72, through the wall 73 of the socket 72, and into the tightening member 106. In the illustrated embodiment, the guide path 104 comprises a diverter 122 and a conduit 124 that are in a coupled arrangement. The diverter 122 defines a duct or passageway 125 and the conduit 124 defines a passageway or duct 140 that are in communication with each other to permit the tensioning line 116 to pass from one to the other.

As shown in FIG. 3, in the illustrated embodiment, an end of the conduit 124 is attached to an inner surface of the diverter 122 that defines the passageway 125. Any suitable attachment mechanism is contemplated, including friction fitting, snap-fit, adhesive, etc. It can be desirable for the engagement mechanism to form a fluid-tight seal, in some instances, to prevent lamination material from entering the guide path 104 at the diverter/conduit interface. As will be apparent from the discussion with respect to FIGS. 18A-19B, and 22 below, in some methods of fabricating the socket 72, either lamination material in liquid form or softened thermoplastic material could potentially enter the guide path 104 in the absence of such a seal. In some instances, however, the connection need not form a fluid-tight seal.

The diverter 122 can comprise any suitable device that is configured to redirect a path of the tensioning line 116. For example, the diverter 122 can be configured to change a direction of the tensioning line 116 from a substantially vertical direction as it passes through the cavity 74 of the socket 72 to a substantially horizontal direction as it passes into the conduit 124. Stated otherwise, the diverter 122 can redirect the tensioning line from movement in a first direction when entering the diverter 122 to movement in a second direction that is different from the first direction when exiting the diverter 122. The first direction can be oriented at a redirection angle relative to the second direction. In the illustrated embodiment, the diverter 122 redirects the path through a 90 degree turn. Stated otherwise, the redirection angle of the diverter 122 is 90 degrees. Other angles of redirection are possible. For example, in various embodiments, the redirection angle is within a range of from about 5 degrees to about 180 degrees, from about 45 degrees to about 180 degrees, or from about 90 degrees to about 180 degrees; is no less than about 30, 45, 60, 75, 90, 120, 150, or 180 degrees; or is no greater than about 30, 45, 60, 75, 90, 120, 150, or 180 degrees.

In some instances, it can be desirable for the redirection to be smooth so as to reduce wear on the tensioning line 116. For example, in the illustrated embodiment, the passageway 125 defines an arc about which the tensioning line 116 is bent. The inner surface of the diverter 122 that defines the passageway can be smooth. Other arrangements are also contemplated.

The diverter 122 can be formed in any suitable manner. In the illustrated embodiment, the diverter 122 is a separate unit that is integrated into the distal end of the socket 72. Further, the diverter 122 is formed of two mated plates 123, each of which forms a longitudinal half of the passageway 125. The plates 123 can be joined in any suitable manner, and in the illustrated embodiment, they are joined by fasteners 127 that extend through threaded through holes 126. In other embodiments, the diverter 122 can merely comprise an end of the conduit 124 that has been rounded to form a diverting path. In such instances, care can be taken to ensure that the bent portion of the conduit 124 is not crushed or kinked during formation of the socket 72, as such a condition could prevent passage of the tensioning line 116. In still further embodiments, the diverter 122 can comprise reinforcements that strengthen the bent portion of the conduit 124 and inhibit crushing or kinking thereof. In various embodiments, it may be desirable for the diverter 122 to comprise a rigid structure to resist crushing or kinking of the passageway 125. In some embodiments, the diverter 122 and/or the conduit 124 may comprise a material that is resistant to degradation when forming the carbon or composition outer shell such as, for example, Teflon, Delrin®, or nylon.

The diverter 122 can define a connection interface 129 that is configured to couple with a plug 500 during formation of the socket 72, as discussed further below with respect to FIGS. 19A-19B. In the illustrated embodiment, the connection interface 129 comprises a boss 128, which extends substantially vertically relative to the upright socket 72 in the illustrated embodiment.

Figure 5:
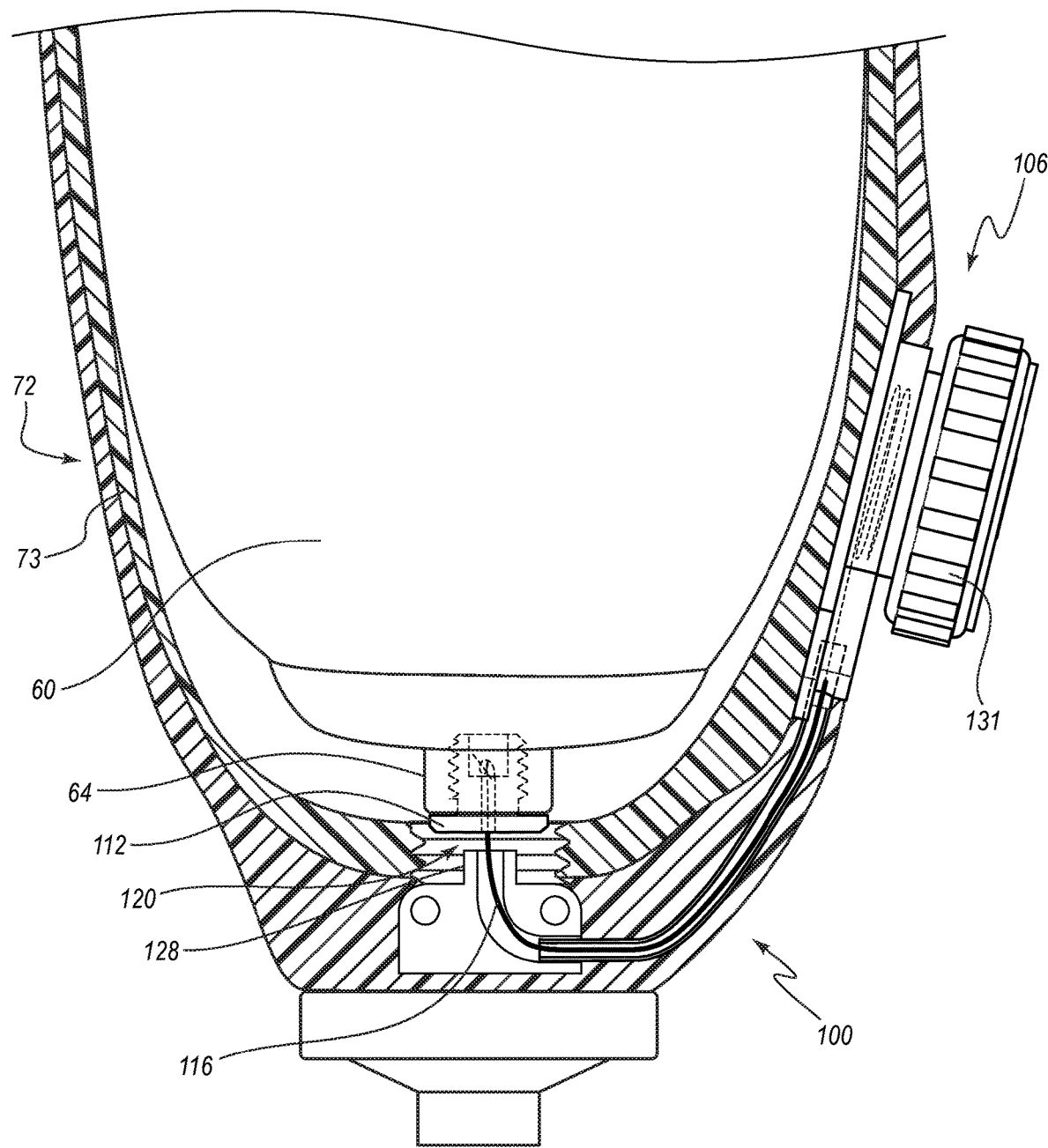
FIG. 5 is another partial cross-sectional view of the distal end of the socket of FIG. 1 showing the lanyard suspension system having fully drawn the liner into the socket.

As shown in FIGS. 2, 3, and 5 (and as discussed further with respect to FIGS. 19A-19B), the plug 500 can leave a recess 120 in the wall 73 of the socket 72. The recess 120 can be sized to receive at least a portion of the connector 112 and/or the connector 64. For example, in some instances, the recess 120 may be sufficiently deep to receive an entirety of the connectors 64, 112 when in a coupled state. In other or further instances, the recess 120 may be sufficiently wide (e.g., have a sufficient inner diameter) to receive the connector 64 therein.

Figure 4:
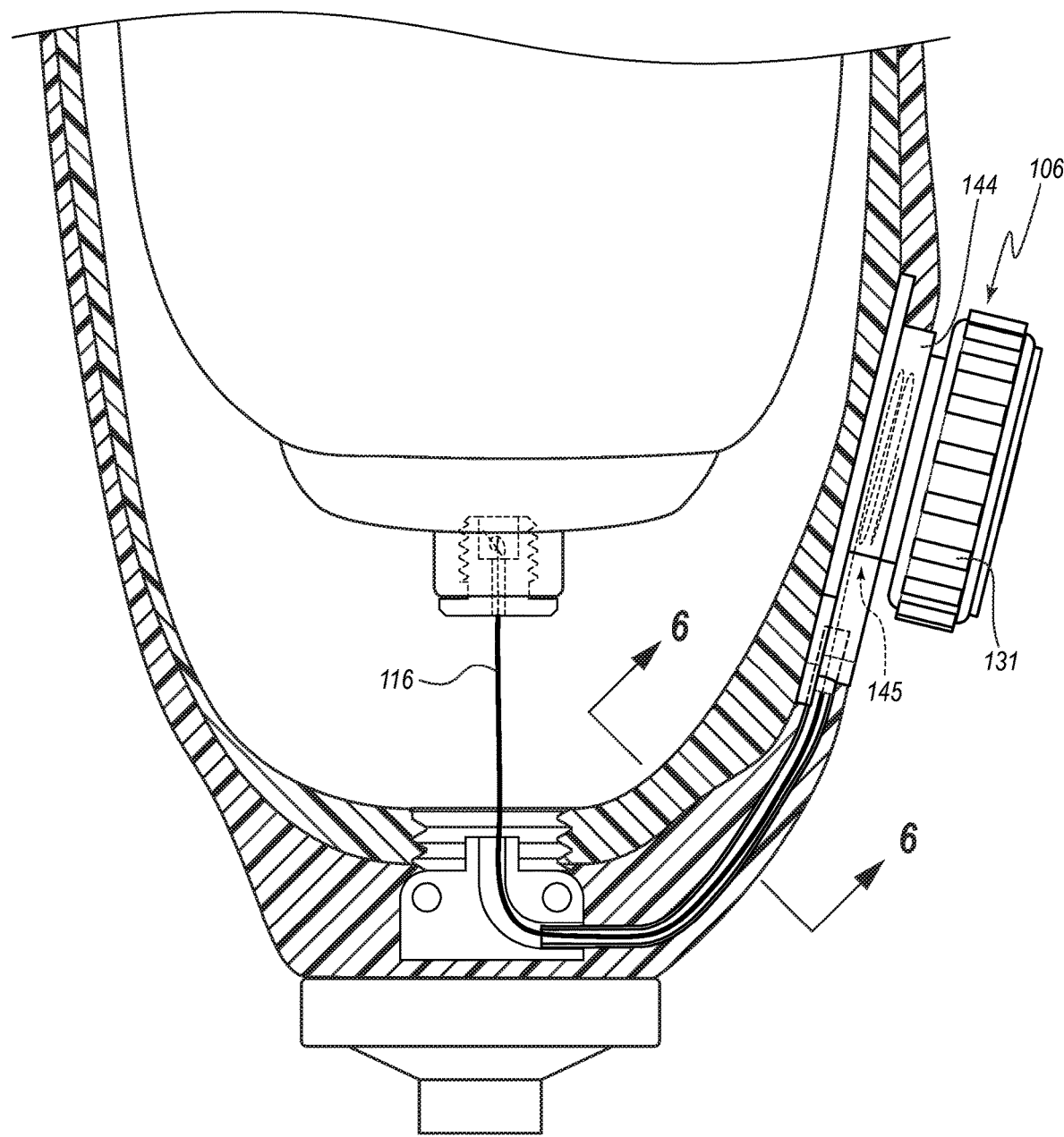
FIG. 4 is another partial cross-sectional view of the distal end of the socket of FIG. 1 showing the lanyard suspension system coupled with a liner and showing the tightening mechanism in an engaged state and drawing the liner into the socket.

The sidewall 73 of the socket 72 can be formed of a single layer of laminated material, or as mentioned previously, it can be formed of multiple layers. In FIGS. 3-5, two schematic layers are depicted, although these are not necessarily to scale, nor are the inner contours of these layers necessarily accurate. Each schematic layer can include one or more layers of reinforcement textiles, such as those previously discussed. A more accurate depiction of the relationship between the layers 91, 92 of the sidewall 73 are depicted in FIG. 6, although this is also a schematic depiction. As shown in this drawing, and as will be more apparent from the discussion of FIGS. 18A-18G below, the conduit 124 can be positioned between the layers 91, 92. The conduit 124 thus can serve as a tunnel through the sidewall 73 through which the tensioning line 116 can translate.

With reference again to FIGS. 3-5, at least a portion of the tightening member 106 can be embedded in the sidewall 73. In the illustrated embodiment, a housing or base 144 of the tightening member 106 is shown as being embedded. The housing or base 144 may include a base mounting portion 146, such as a base mounting plate, and may also include a reel housing portion 147. In the illustrated embodiment, the base mounting portion 146 and the reel housing portion 147 are integrally formed into a single component, such that the single component is referred to herein interchangeably either as the housing 144 or the base 144. In other embodiments, the base mounting portion 146 and the reel housing portion 147 may be separate components that can be coupled with each other, as described more fully with respect to other embodiments (see, e.g., FIGS. 23A-23C and associated written description).

Figure 8:
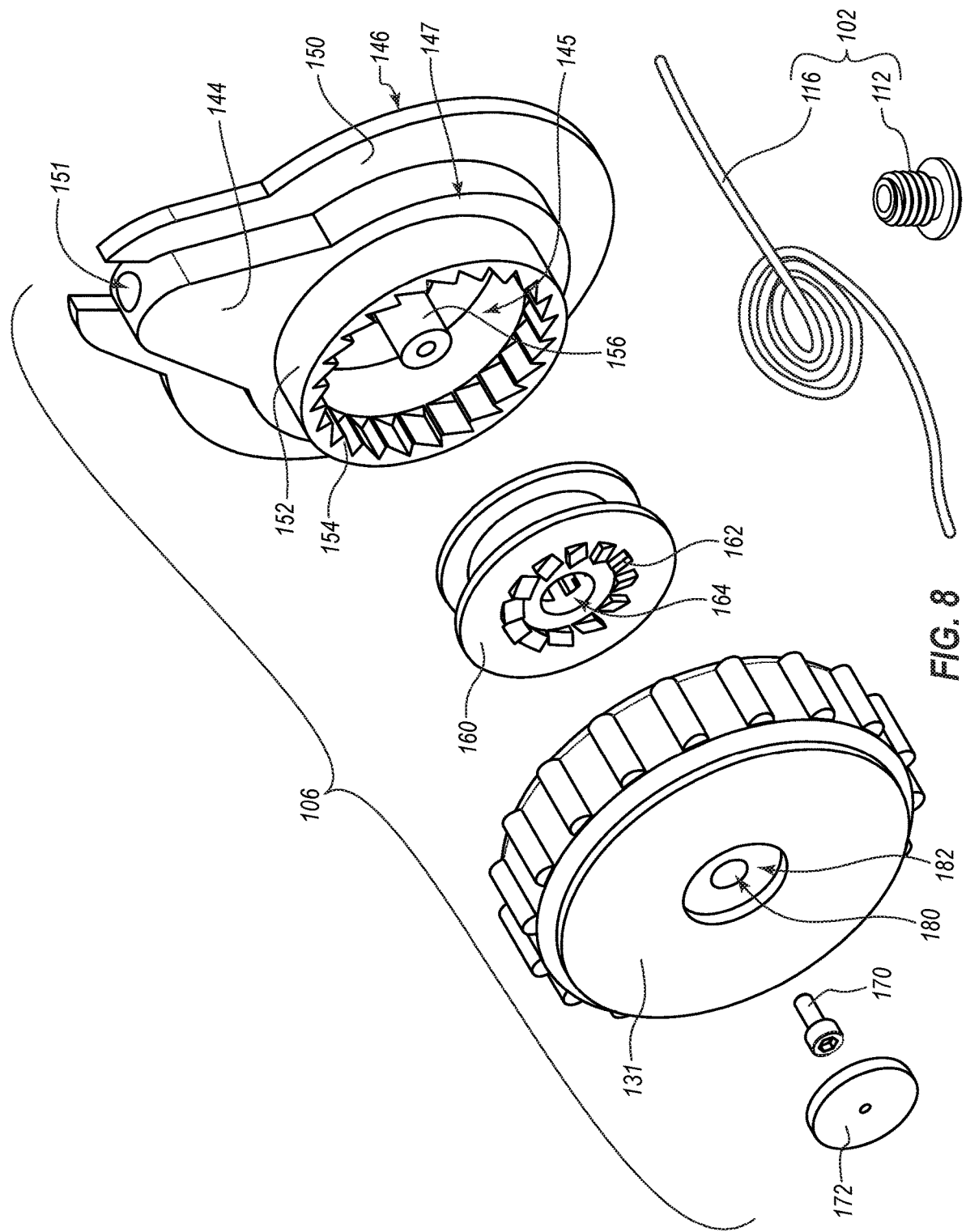
FIG. 8 is an exploded perspective view of the tightening mechanism and the lanyard.

The base mounting portion 146 of the base 144 can include an outwardly extending flange 150 (see FIGS. 3 and 8). At least the flange 150 of the base 144 is depicted as being laminated between two layers of the sidewall 73. The reel housing portion 147 of the base 144 can define a recess or cavity 145 into which the tensioning line 116 can be gathered as the lanyard 102 draws the liner 60 into the socket 72. As the tensioning line 116 is gathered into the tightening device 106, it can be fully housed or encased within the tightening device 106. Such an arrangement can keep the tensioning line 116 out of view when the liner 60 is being suspended in the socket 72, such as, for example, if the housing 144 and a cover 131 (FIG. 2) over the housing 144 are continuous and opaque. In other or further arrangements, housing or encasing the tensioning line 116 within the tightening device 106 can inhibit or prevent the tensioning line 116 from inadvertent snagging (which could trip a user, for example), weathering, and/or other undesirable results of exposure.

The tightening member 106 can be configured to increase or decrease a tension in the tensioning line 116. The tightening member 106 can include an actuator 130 that effects the gathering of the tensioning line 116. In some embodiments, the actuator 130 can be used to selectively and/or incrementally increase the tension in the tensioning line 116. In other or further embodiments, the actuator 130 can be used to selectively and/or incrementally decrease the tension in the tensioning line 116. In the illustrated embodiment, the actuator 130 comprises a substantially disk-shaped knob 131 (which was previously referred to as a cover, as the knob additionally functions as a cover relative to the housing 144 in the illustrated embodiment). The knob 131 can be transitioned between a tension-release state and an engaged state. The tension-release state is shown in FIG. 3, and the engaged state is shown in FIGS. 4 and 5.

As shown in FIG. 3, in the illustrated embodiment, the knob 131 is retracted away from the base 144 to move the actuator 130 to the tension-release state. In this state, the tensioning line 116 can be drawn or pulled out of the tightening member 106. Thus, in FIG. 3, the lanyard 102 can be pulled vertically through the socket cavity 74 to facilitate coupling of the connector 112 with the liner 60. In moving the lanyard 102 in this manner, portions of the tensioning member 116 can move from the cavity 145 of the housing 144, through the duct 140 of the tube 124, through the passageway 125 of the diverter 122, and into the cavity 74 of the socket 72.

As shown in FIG. 4, in the illustrated embodiment, the knob 131 is advanced toward the base 144 to move the actuator 130 to the engaged state. In this state, the actuator 130 can be actuated to tighten the tensioning line 116. In the illustrated embodiment, the actuator 130 is actuated by rotating the knob 131. As further discussed below, this action can cause the tensioning line 116 to be reeled up within the cavity 145 defined by the base 144 of the tightening member 106.

FIG. 5 depicts a stage of operation at which the liner 60 has been drawn into the socket 72 and is being held tightly in place via the lanyard suspension system 100. Transition to this state from the state shown in FIG. 4 can be achieved by additional rotation of the knob 131 to draw additional amounts of the tensioning line 116 into the tightening member 106. At certain periods of this process, the tension in the tensioning line 116 can increase. Advantageously, due to the manner in which the tightening member 106 operates (discussed below with respect to FIGS. 7-9), at least a portion of the forces that arise due to this increased tension are distributed into the socket wall 73.

For example, in the illustrated embodiment, as further discussed below (with respect to FIG. 8), the tensioning line 116 is wrapped about a spool or reel 160 that is pivotally mounted to a post 156 defined by the base 144. As tension in the tensioning line increases, forces are distributed from the post 156, which assists in keeping one end of the tensioning line 116 taut, to other portions of the base 144 that are in direct contact with the socket wall 73. The socket wall 73 is able to counter these forces that are distributed to it via the base 144 in order to maintain the tensioning line 116 in tension. Such an arrangement can facilitate tensioning of the tensioning line, as a user is not required to provide all of the force that might otherwise be necessary to snugly secure the liner 60 in the socket 72. As will be appreciated in view of the discussion below regarding operation of the tightening member 106, the tightening member 106 can distribute force, which is due to tension in the tensioning line, into the socket 72 throughout an entirety of an actuation event by which actuation of the actuator 130 increases tension in the tensioning line 116. For example, the post 156 can distribute forces from the reel 160, which forces arise from the tensioning line, to the portions of the base 144 that are in direct contact with the socket wall 73 throughout an entirety of an actuation event in which the knob 131 is rotated, or repeatedly rotated, to increase the tension on the tensioning line 116.

Figure 7:
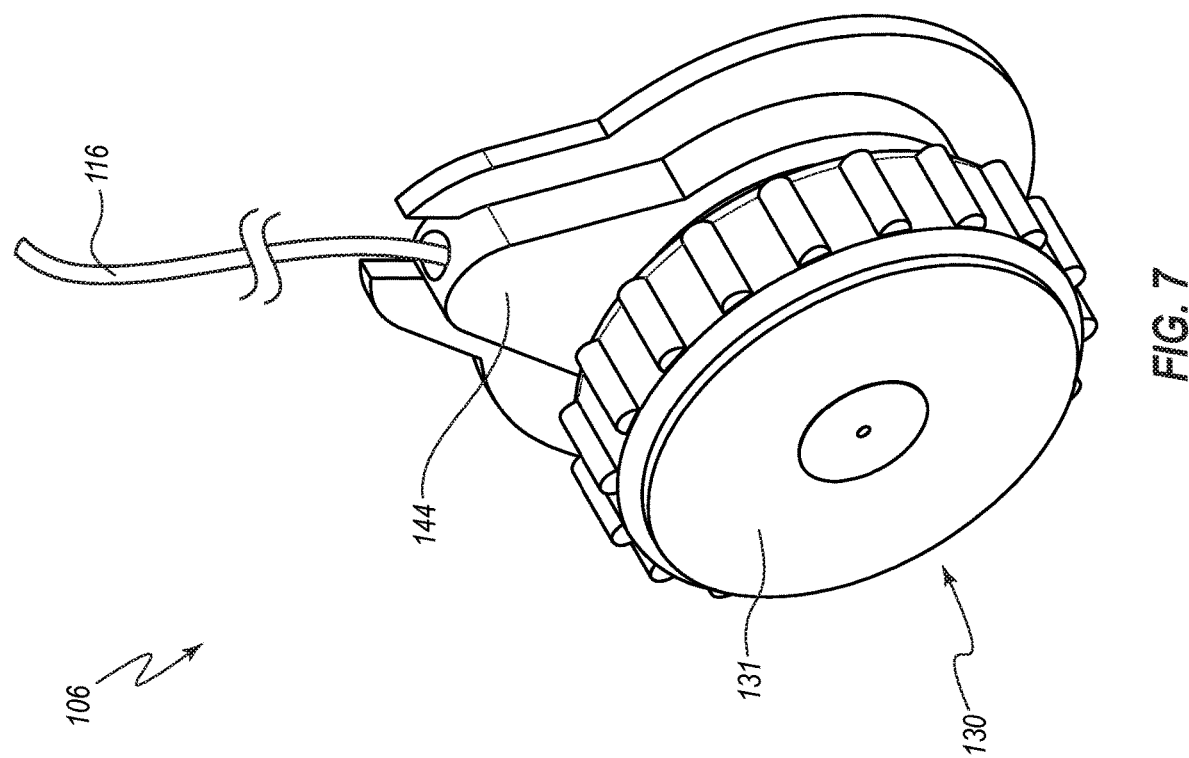
FIG. 7 is a perspective view of the tightening mechanism coupled with the tensioning line of an embodiment of a lanyard.
Figure 9:
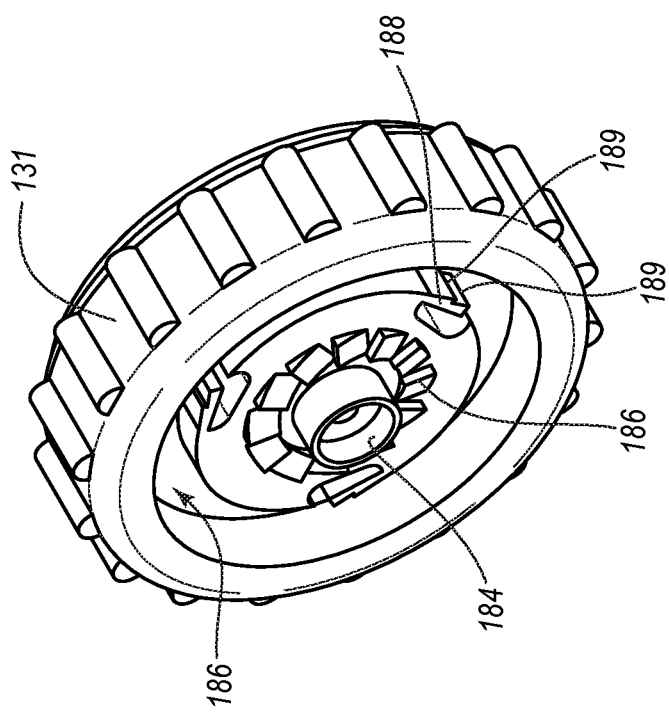
FIG. 9 is a reverse perspective view, relative to FIG. 8, of an actuator portion of the tightening mechanism of FIG. 7.

With reference to FIGS. 7-9, the illustrated tightening device 106 can include the housing or base 144 and the actuator 130. As will be appreciated from the discussion that follows, the illustrated embodiment of the tightening device uses a ratcheting mechanism in operation. Accordingly, the tightening device 106 may also be referred to herein as a ratcheting device.

In FIG. 7, the ratcheting device 106 is shown coupled with the tensioning line 116. The actuator 130 is operable to selectively rotate in a first direction (e.g., clockwise) so as to gather the tensioning line 116 within the housing 144 when the actuator is in an engaged state, and is operable to permit a release of tension from the tensioning line 116 (whether full or partial) when the actuator is in a tension-release state.

With reference to FIGS. 7-9, the illustrated actuator 130 includes a knob 131 that has a plurality of pawls 188. As shown in FIG. 9, the knob 131 further includes a plurality of teeth 186. The knob 131 cooperates with the base 144 to secure a spool 160 in the cavity 145 of the base. The base 144 includes an upward protrusion 152 that has a plurality of teeth 154 that are configured to engage with the pawls 188 defined by the knob 131 so as to permit the knob 131 to move in a first direction relative thereto but to prevent movement in a second direction relative thereto. In particular, the pawls 188 include angled surfaces 189 that are configured to compress the pawls 188 as they rotate relative to the teeth 154 in a first direction, but are configured to engage the teeth 154 and prevent rotation in a second direction. The knob 131 further defines a protrusion 184 that can receive a portion of spool 160 so as to maintain an alignment thereof.

The base 144 defines the cavity 145 for receiving the spool 160. The base 144 further defines a channel 151 into the cavity 145 through which the tensioning line 116 can enter the device 106 so as to wrap around the spool 160. The spool 160 includes teeth 162 that are configured to engage with the teeth 186 of the knob 188 so as to rotate the spool 160 when the knob 188 is rotated in the first direction.

The post 156 can be secured to the knob 131 via a screw 170. A plate 172 may be secured over the screw 170, such as to permit the screw 170 to be held loosely when the actuator 130 is moved to the tension release state. When the knob 131 is pushed downwardly, it is in an engaged or tightening state in which the pawls 188 of the knob 131 are engaged with the teeth 154 of the protrusion 152 of the base 144.

With sufficient force, the knob 131 can be pulled outwardly so as to disengage the pawls 188 and the teeth 154. When in this position, the knob 131 is in the tension-release state, as the pawls 188 no longer engage the teeth 154 and the teeth 186 of the knob 131 no longer engage the teeth 162 of the spool 160. The spool is thus free to rotate in a direction opposite of that used to tighten the tensioning line 116, and may do so, for example, until sufficient tension is released for the rotation to terminate.

The ratcheting device 106 thus permits rotation of the knob 131 in a single direction while limiting rotation of the knob 131 in the opposite rotation direction. Moreover, the ratcheting device 106 may allow incremental adjustments feature to tension in the line 116. A larger number of teeth 154 can allow for small increments of change in the tension.

In various embodiments, the teeth can permit anywhere from 1 to 30 degrees of rotation, which can result in a small amount of change in tension in the tensioning line 116 with each step. Such capability of applying incremental amounts of tension in the tensioning line 116 may permit a user to tighten the liner 60 into the socket 72, as needed or as desired.

Any suitable tightening device 106 is contemplated. In various embodiments, the ratcheting device 106 can comprise a B1109 reel-based tightening system available from BOA TECHNOLOGY INC. of Denver, Colorado Other suitable devices are disclosed, for example, in U.S. Pat. No. 8,091,182, the entire contents of which are hereby incorporated by reference herein.

With reference to FIGS. 2-5 and 10, as previously mentioned, the base 144 can be integrated into the socket 72. Various stages of an embodiment of a method for such incorporation are depicted in FIGS. 18A-18G. In many applications, it can be undesirable for the actuator 130 to be coupled with the base 144 during fabrication of the socket 72. For example, in lamination processes, the laminating material (e.g., resin) can solidify about the actuator 130 in ways that can greatly inhibit or prevent the proper operation thereof. As can be appreciated from the present discussion of FIG. 10, however, it can also be undesirable to fabricate the socket 72 with the base 144 alone, as the laminating material can enter the cavity 145 and/or the channel 151. Similar problems can arise when the socket 72 is formed of thermoplastic materials.

Figure 11:
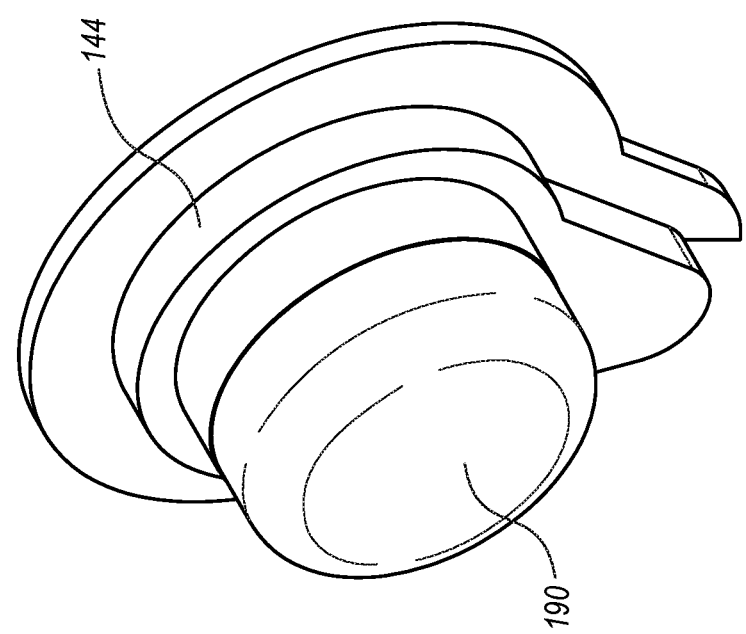
FIG. 11 is a perspective view of the base portion of the tightening mechanism coupled with an embodiment of a dummy.
Figure 10:
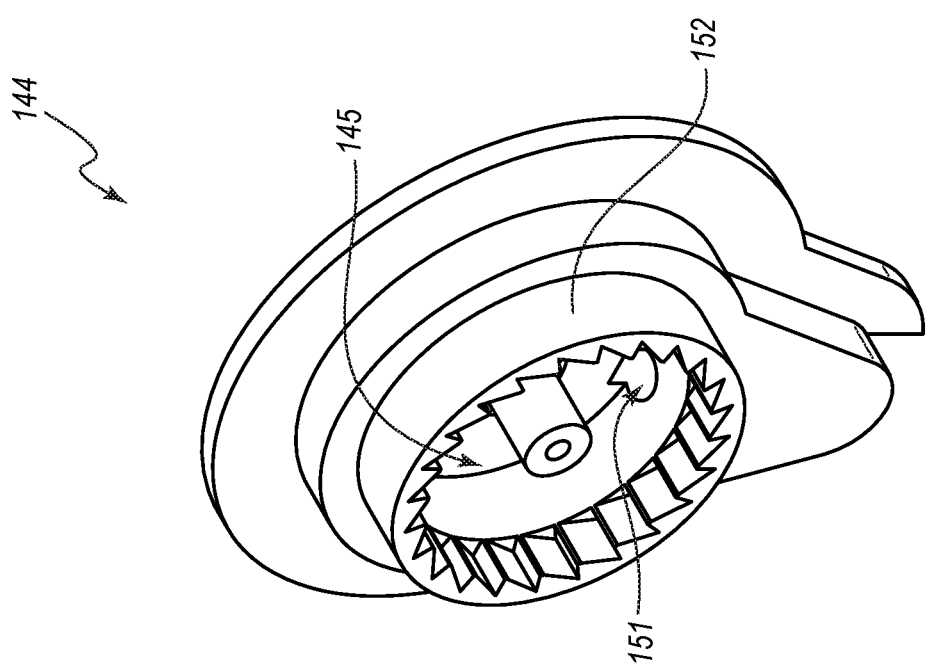
FIG. 10 is a perspective view of a base portion of the tightening mechanism.

With reference to FIG. 11, in various embodiments, a sacrificial dummy 190 or blank is used with the base 144 for formation of the socket 72. When the socket is completed, the dummy 190 can be removed and replaced with the actuator 130. The dummy 190 can be configured to close off the cavity 145 to prevent material (e.g., lamination material, thermoplastic) from entering therein during fabrication of the socket 72. In some embodiments, the dummy 190 can form a fluid-tight seal with the base 144.

In the illustrated embodiment, the dummy 190 comprises silicone that has been overmolded to the base 144. The silicone can fill a portion of the channel 151 and substantially all of the cavity 145. The silicone can be easily removed from the base 144 after the formation of the socket. In some instances, a seal between the dummy 190 and the base 144 can be formed or enhanced as vacuum is applied to the layup of the socket during distribution of the lamination material. For example, operating under vacuum or suction can, in some instances, cause the dummy to more tightly compress against the base 144, which may be formed of any suitable material and may, in many instances, be more rigid than the dummy 190. In various embodiments, the base 144 comprises a rigid or semi-rigid plastic. Further, in some embodiments, the dummy 190 may be configured to readily release from a hardened resin material. In some embodiments, the dummy 190 comprises a plastic, such as a thermoplastic (e.g., Delrin®).

In some embodiments, the dummy 190 can comprise a cover or cap that merely extends over the cavity 145 and is configured to seal against the base 144 about a periphery of the cavity 145. In various embodiments, at least a portion of the dummy 190 can extend about a full periphery of the exterior of the vertical projection 152, can contact the vertical projection 152 around an entire upper surface thereof, and/or can interface with the full inner periphery of the vertical projection 152. In various embodiments, the dummy 190 can be a single-piece unit, such as the silicone overmold discussed above. In other embodiments, multiple pieces may be used, such as a plastic cap coupled with an o-ring. In various instances, the dummy 190 can be formed separately from the base 144, rather than via overmolding. For example, in some embodiments, the dummy 190 can comprise a silicone plug that is sized to fit within the cavity 145 and extend over an upper end of the annular projection 152. Such a dummy 190 can be inserted into the cavity 145 during layup of the socket, and application of vacuum or suction during introduction of a lamination material may aid in ensuring that none of the material enters the cavity 145. Any suitable format of the dummy 190 is contemplated.

FIGS. 12-16 illustrate another embodiment of a tightening mechanism, tightening device, or ratcheting device 206, which can resemble the tightening device 106 described above in certain respects. Accordingly, like features are designated with like reference numerals, with the leading digits incremented to "2." Relevant disclosure set forth above regarding similarly identified features thus may not be repeated hereafter. Moreover, specific features of the ratcheting device 206 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the ratcheting device 206. Any suitable combination of the features and variations of the same described with respect to the tightening device 106 can be employed with the ratcheting device 206, and vice versa. This pattern of disclosure applies equally to further embodiments depicted in subsequent figures and described hereafter.

Figure 12:
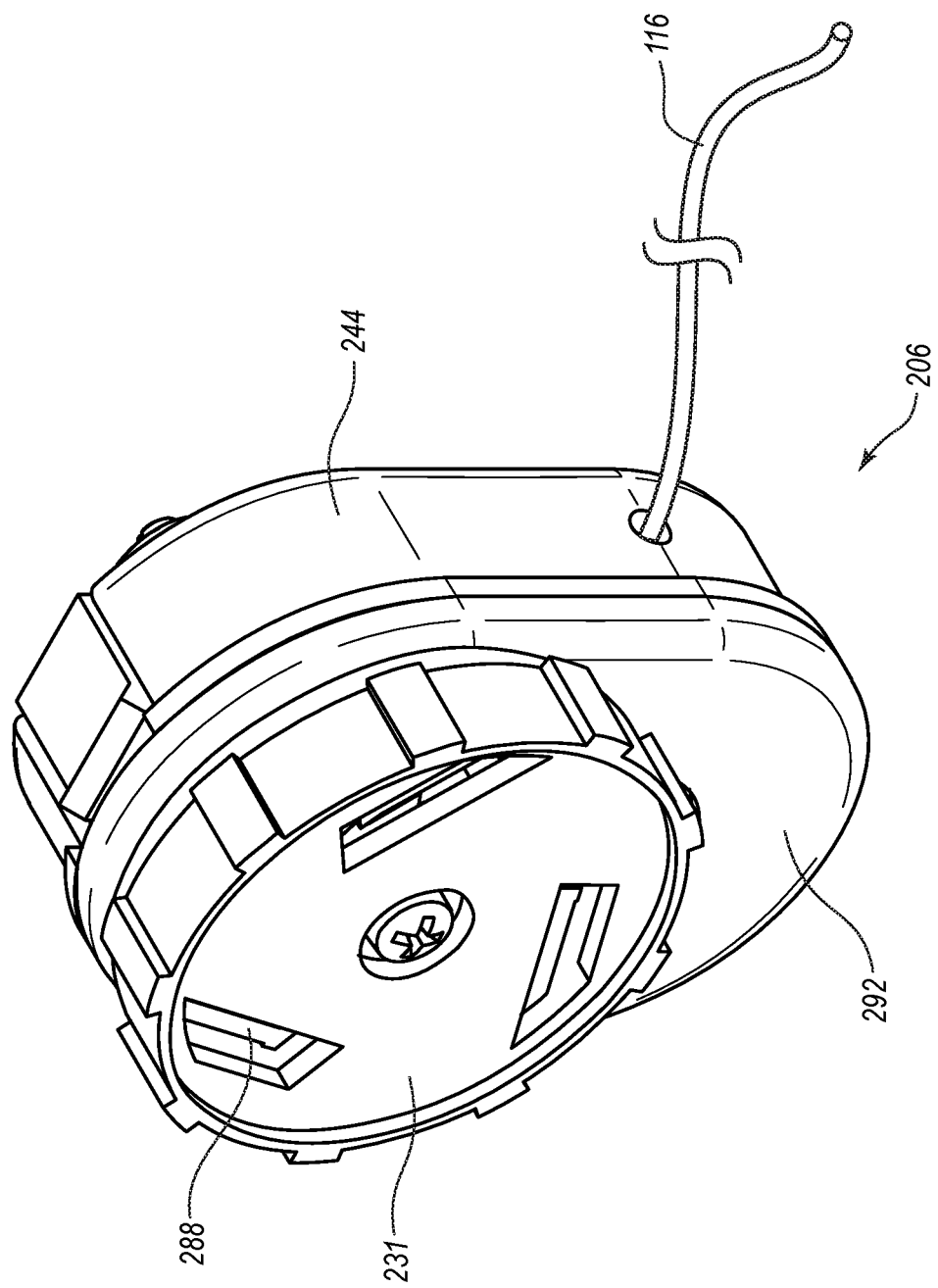
FIG. 12 is a perspective view of another embodiment of a tightening mechanism coupled with the tensioning line of an embodiment of a lanyard.
Figure 13:
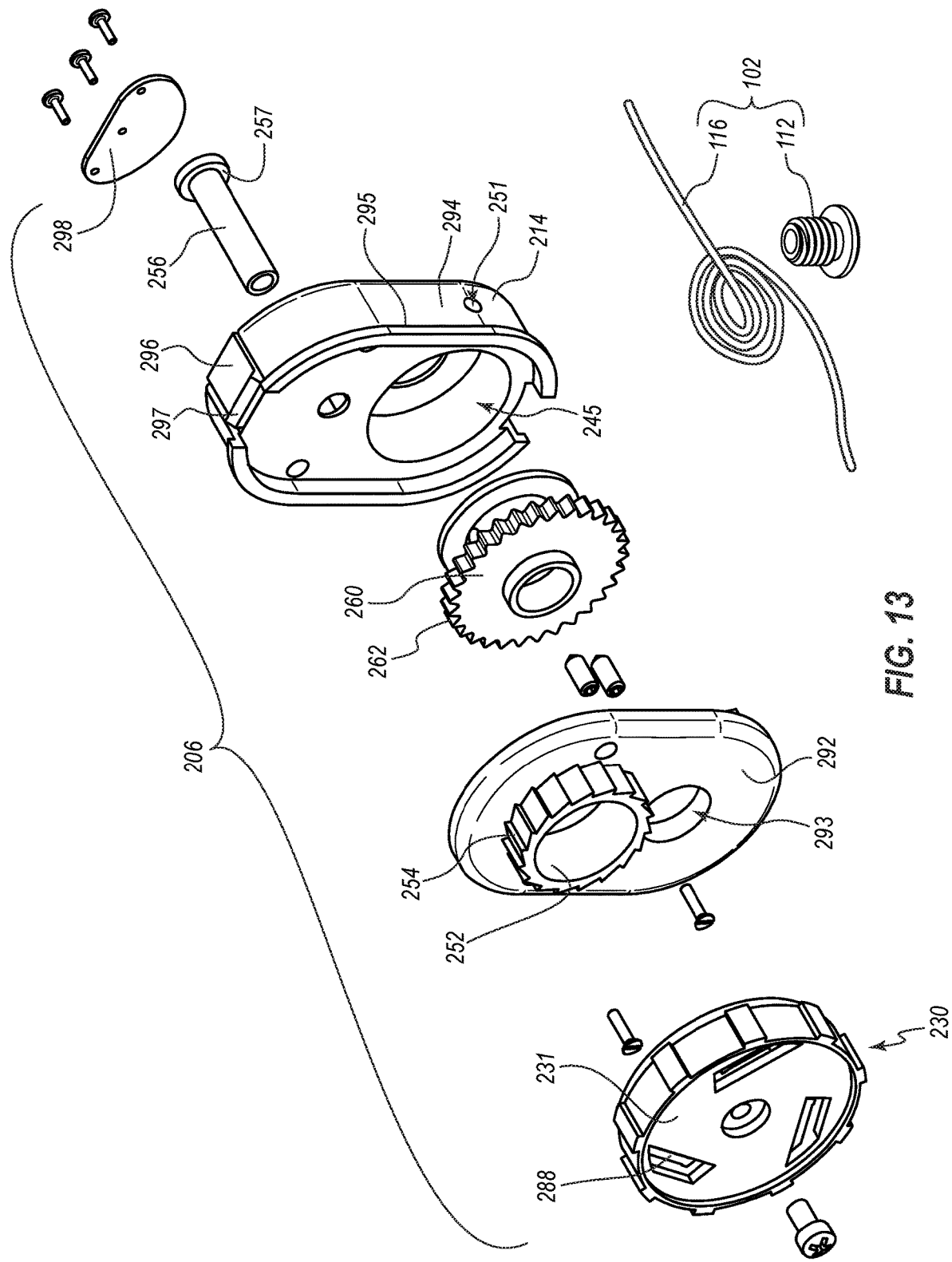
FIG. 13 is an exploded perspective view of the tightening mechanism of FIG. 12 and the lanyard.

The ratcheting device 206 can include a housing or base 244, a cover 292, and an actuator 230. In FIG. 12, the ratcheting device 206 is shown coupled with a tensioning line 116. The actuator 230 is operable to selectively rotate in a first direction (e.g., clockwise) so as to gather the tensioning line 116 within the base 244 (which may also be referred to herein as a housing or housing element) and the cover 292 when the actuator is in an engaged state, and is operable to permit a release of tension from the tensioning line 116 (whether full or partial) when the actuator is in a tension-release state.

Figure 14:
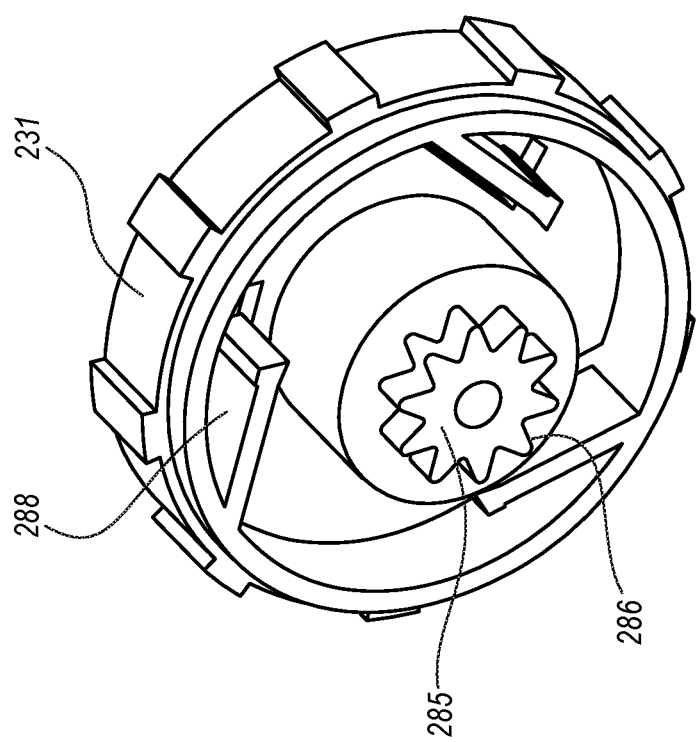
FIG. 14 is a reverse perspective view, relative to FIG. 13, of an actuator portion of the tightening mechanism of FIG. 12.
Figure 16:
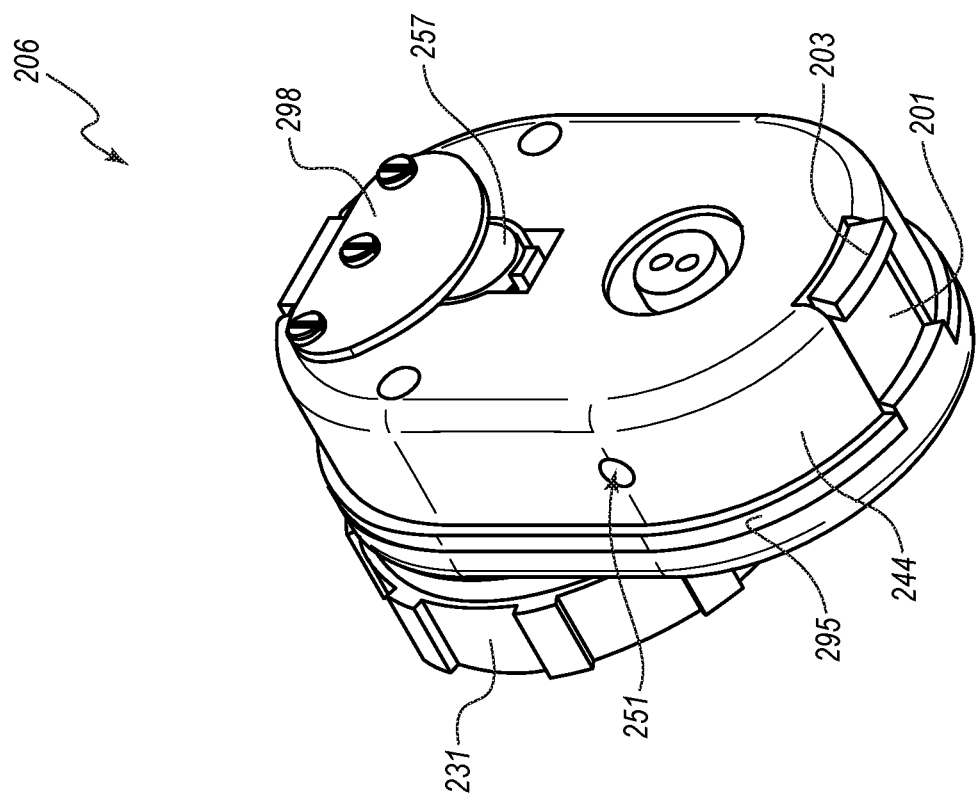
FIG. 16 is a lower rear perspective view of the tightening mechanism of FIG. 12.

The actuator 230 includes a knob 231 that has a plurality of pawls 288. As shown in FIG. 14, the knob 231 includes a gear 285 with teeth 286. The cover 292 and the base 244 cooperate with each other to secure a spool 260 therein. The cover 292 includes an upward protrusion 252 that has a plurality of teeth 254 that are configured to engage with the pawls 288 so as to permit the knob 231 to move in a first direction relative thereto but to prevent movement in a second direction relative thereto. The cover 292 defines an opening 293 that can receive a portion of spool 260 so as to maintain an alignment thereof. The cover 292 further defines a resilient arm 201 that defines a tab 203 at an end thereof (see FIGS. 15 and 16).

The base 244 defines a cavity 245 for receiving the spool 260. The base 244 defines a channel 251 through which the tensioning line 116 can enter the housing so as to wrap around the spool 260. The spool 260 includes teeth 262 that are configured to engage with the teeth 286 of the knob 288 so as to rotate the spool 260.

The base 244 includes a base region 294 that is bordered by a flange 295 at an upper end thereof. The base 244 includes a resilient arm 296 that includes a tab 297 at an upper end thereof.

Figure 15:
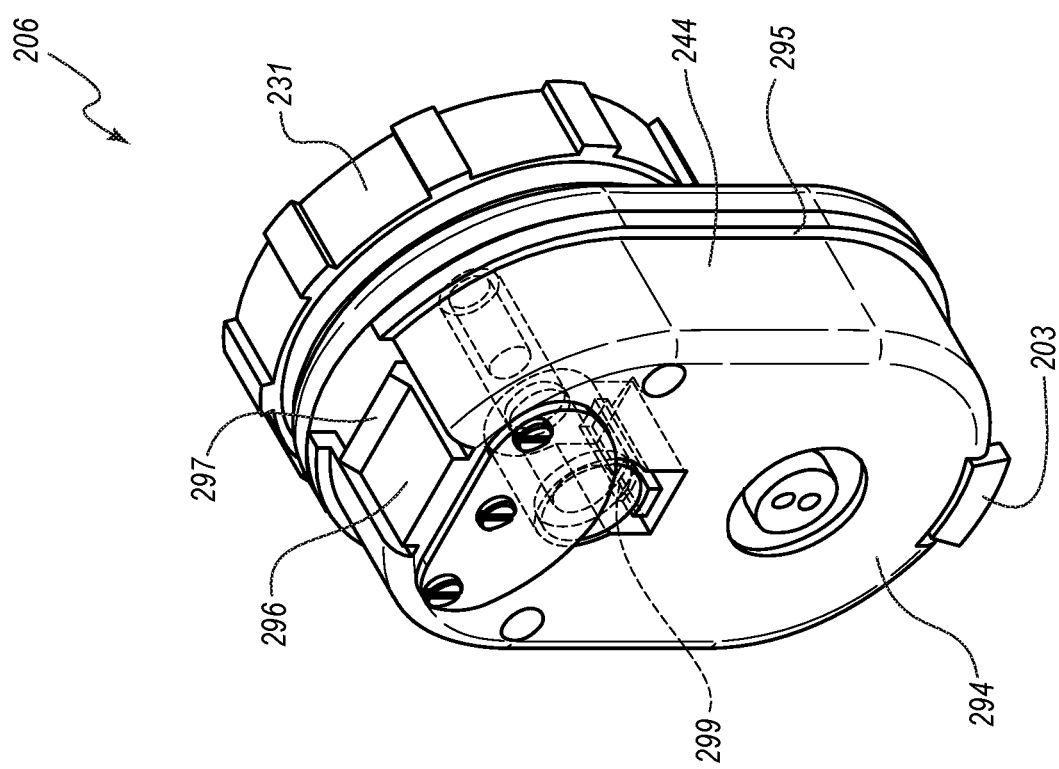
FIG. 15 is an upper rear perspective view of the tightening mechanism of FIG. 12.

A post 256 can extend through the base region 294 of the base 244 and can be secured to the knob 231 via a screw. A plate 298 can be attached to the base 244 so as to prevent the post 256 from being removed from the base 244. The post includes a flange 257, and the base 244 defines a resilient catch 299 (FIG. 15). When the knob 231 is pushed downwardly, the flange 257 of the post 256 bypasses the catch 299 and is held in place thereby. The knob 231, when in this position, is in an engaged or tightening state. When in this state, the pawls 288 of the knob 231 are engaged with the teeth 254 of the protrusion 252 of the cover 292.

With sufficient force, the knob 231 can be pulled outwardly so as to move the flange 257 of the post 256 upwardly past the catch 299. When in this position, the knob 231 is in the tension-release state, as the pawls 288 no longer engage the teeth 254 and the teeth 286 of the gear 285 of the knob 231 no longer engage the teeth 262 of the spool 260. The spool is thus free to rotate in a direction opposite of that used to tighten the tensioning line 116, and may do so, for example, until sufficient tension is released for the rotation to terminate.

The ratcheting device 206 thus permits rotation of the knob 231 in a single direction while limiting rotation of the knob 231 in the opposite rotation direction. Moreover, the ratcheting device 206 may allow incremental adjustments feature to tension in the line 116.

Figure 17:
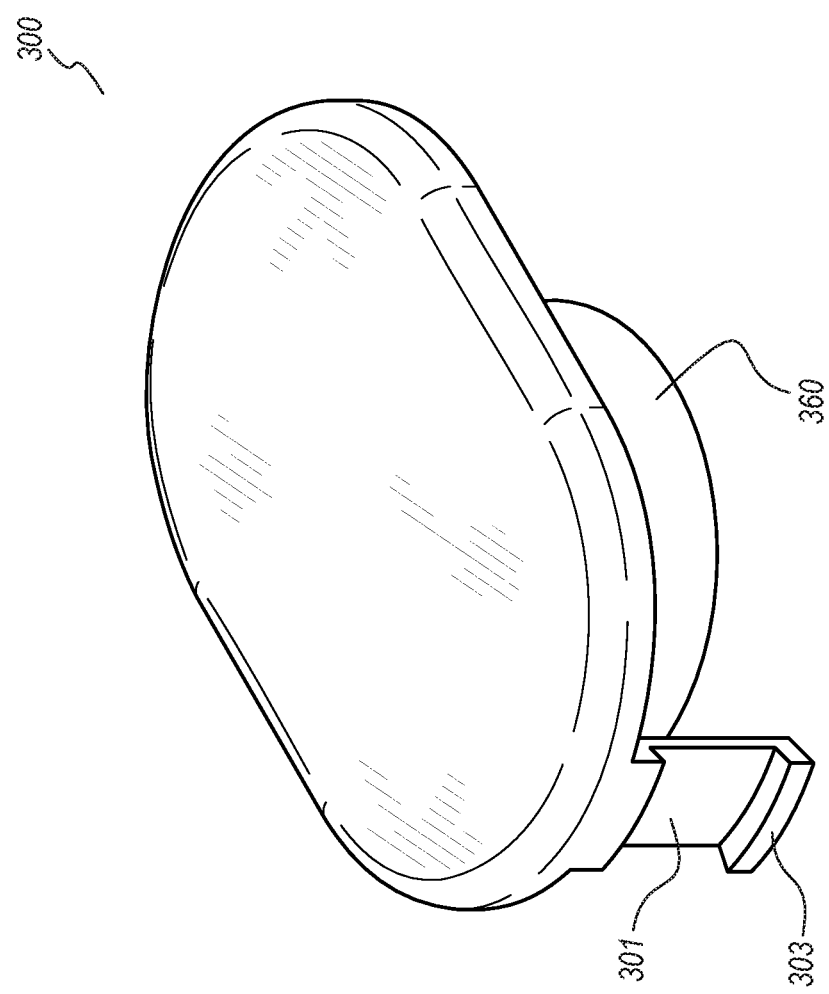
FIG. 17 is a perspective view of another embodiment of a dummy that is configured for use with a base portion of the tightening mechanism of FIG. 12.

FIG. 17 illustrates another embodiment of a dummy or template 300 that can be used in forming a socket 72, such as via a laminating procedure or a thermoforming procedure. The template 300 can serve as a cap to prevent material (e.g., liquid resin) from entering the base 244. In particular, in some procedures, the base 244 and the template 300 can be joined together and the base 244 is then laminated directly in place. The template 300 can include a protrusion 360 that extends into and fills the base 244. The template 300 can also include a flexible arm 301 and tab 303 that resemble the arm 201 and the tab 203 described above.

FIGS. 18A-18G illustrate various stages of an illustrative method in which the dummy 190 (see FIG. 11) can be used in the formation of a socket, such as the socket depicted in FIG. 1. Some portions of the procedures are known in the art, and thus will not be described in detail. It is also noted that many different materials and procedures are possible, and that the following discussion is merely illustrative of examples of the same.

Figure 18B:
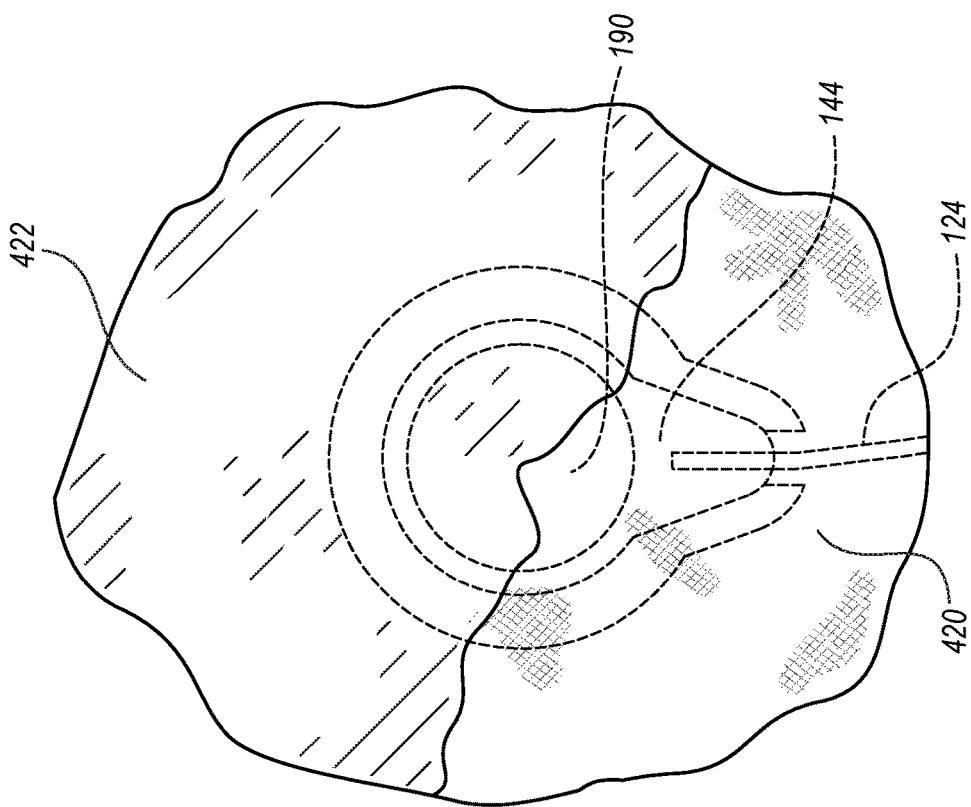
FIGS. 18A-18G are schematic plan views of various stages of an illustrative method for manufacturing the socket.
Figure 18A:
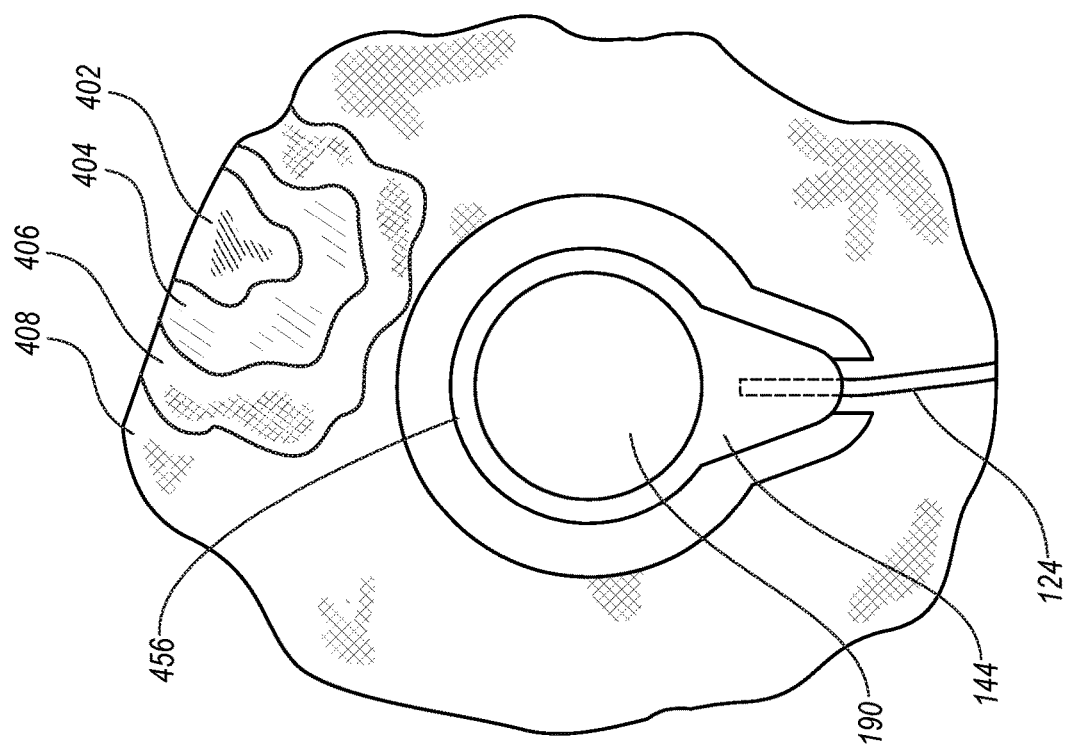

FIG. 18A illustrates placement of the base 144 and the dummy 190 in a coupled state at a desired position during a layup procedure. In the illustrated embodiment, the dummy 190 has been overmolded to the base 144, but other arrangements are possible, as described above. The conduit 124 is also shown coupled to the base 144 in a desired path. An end of the conduit 124 is inserted deeply into the base 144 (i.e., into the channel 151). The conduit 124 can form a tight fit with the channel 151 so as to prevent liquid resin from entering therein.

A mold 402 that represents the residuum is covered with a barrier layer 404 of flexible plastic or foam, such as a PVA bag. The mold may be of any suitable variety, such as, for example, a dried and hardened plaster mold or a carved-out foam mold. Another layer 406 of plastic, such as a PVA bag is positioned over the layer 404. These layers are covered by one or more layers of fibers and/or fabric, such as a carbon fiber layer 408. The base 144 may be attached to the layup in any suitable manner, such as by an adhesive.

FIG. 18B shows that another layer 420 of one or more materials (e.g., fabric and or fibers) may be provided over the base 144, the dummy 190, and the conduit 124 such that these items are sandwiched therebetween. Another barrier layer 422 of plastic is provided over the layer 420.

Figure 18C:
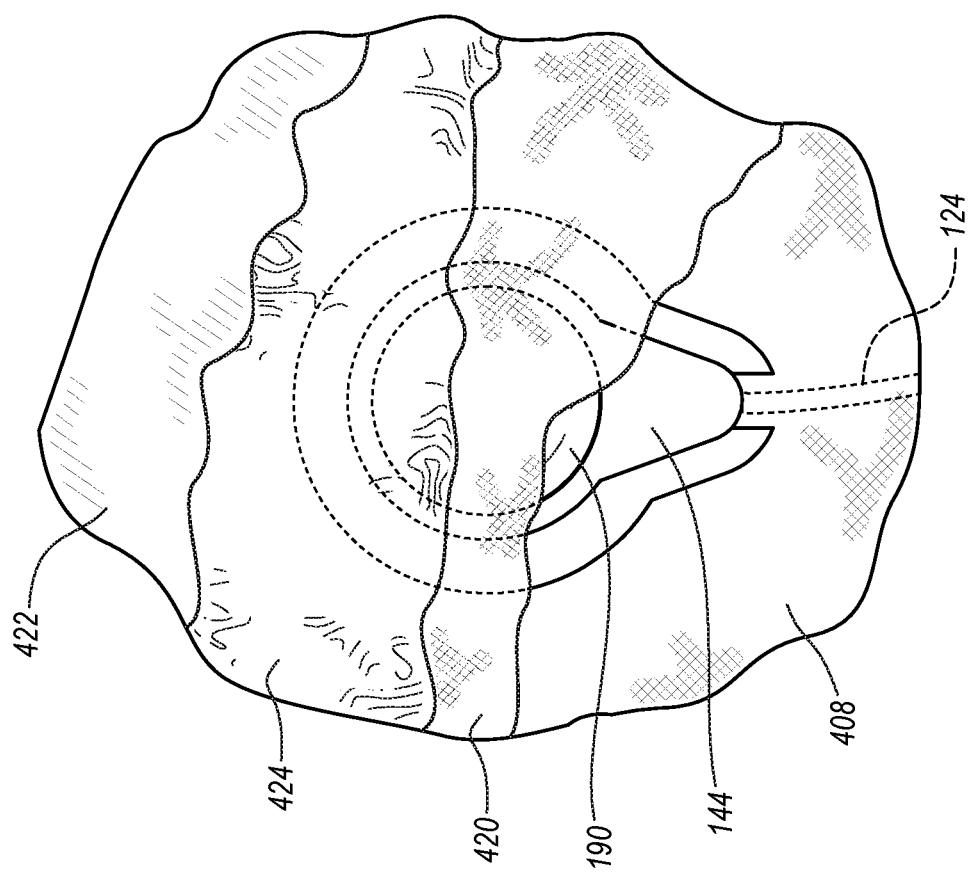

FIG. 18C illustrates the introduction of liquid resin 424 about the base 144, the dummy 190, and the conduit 124. The resin 424 can saturate the fabric layers 408, 420, and can be constrained by the barrier layers 406, 422.

Figure 18E:
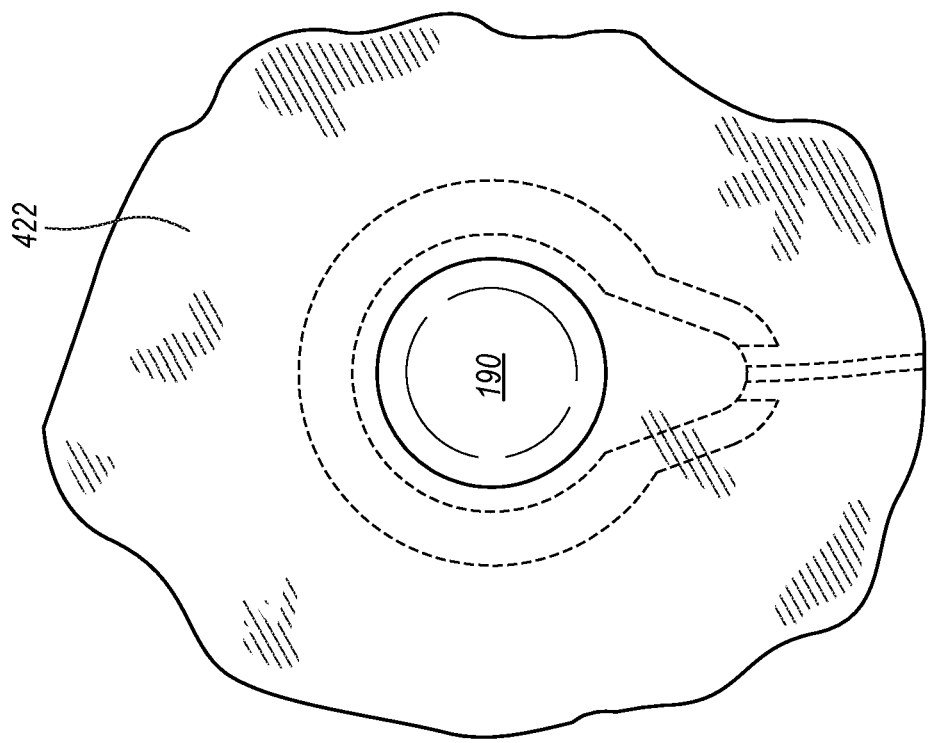
Figure 18D:
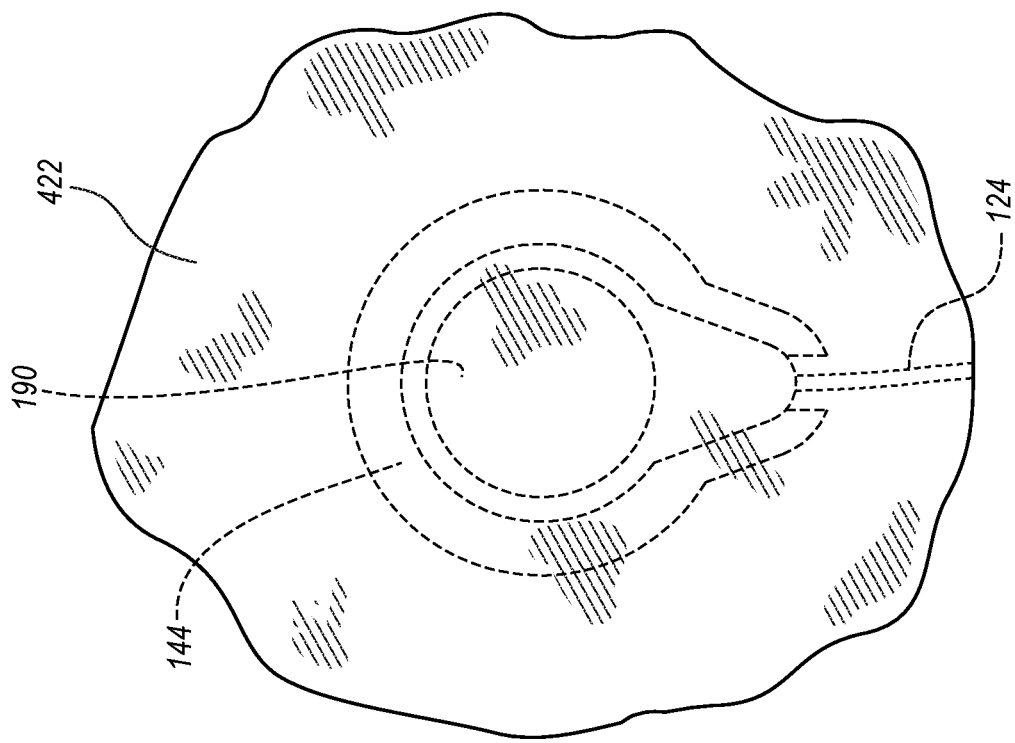

FIG. 18D shows the hardened or cured resin 424 and the barrier layers 406, 422 removed. The base 144, the dummy 190, and the conduit 124 are thus positioned within a single laminated layer.

FIG. 18E shows a portion of the resin 424 removed from above the dummy 190. The resin 424 can be removed in any suitable manner, such as by cutting, sanding, or grinding. Caution may be used in some instances to remove only sufficient amount of the material above the dummy 190 to expose the top surface of the dummy 190.

Figure 18G:
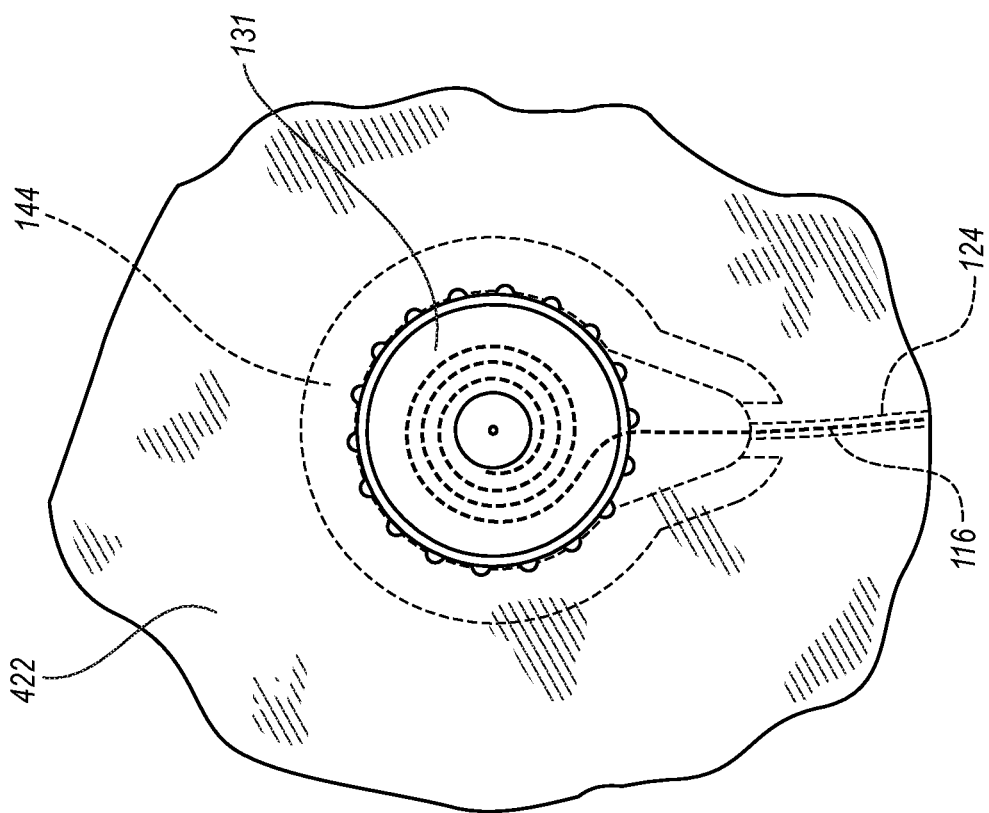
Figure 18F:
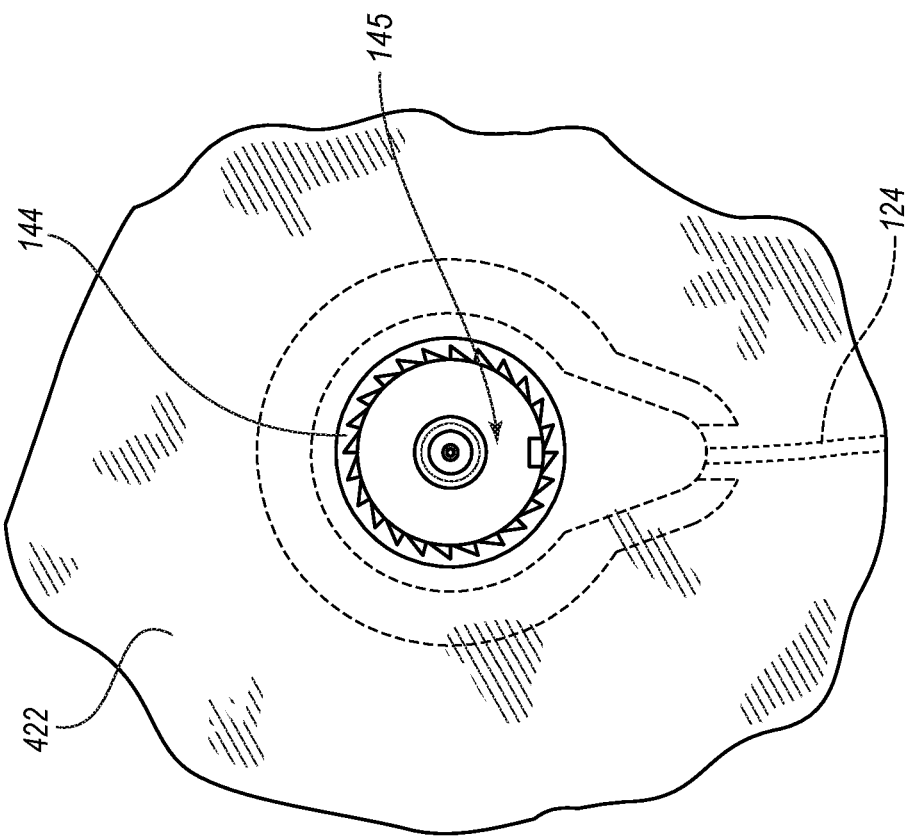

FIG. 18F shows a stage after removal of the dummy 190 to expose the cavity 145 of the base 144. The conduit 124 remains on the original guide path that it defined during layup.

FIG. 18G shows the knob 131 coupled to the base 144. Prior to coupling the knob 131 with the base 144, the tensioning line 116 can be advanced through the conduit 124 (and, in the illustrated embodiment, through the diverter 122) such that at least a portion of the tensioning line 116 is positioned in the base 144 for coupling with the reel 160 and another portion thereof is positioned in the socket 72 for coupling with the connector 112. Additional and/or other methods for securing the ratcheting device 106 also may be employed, such as the use of adhesives. The tensioning line 116 can be tightened by rotation of the knob 131.

The foregoing method is an example of a single-lamination method. In other methods, multiple laminations may be performed. For example, with reference to FIG. 18A, in some embodiments, the base 144 may originally be secured to a first laminated layer, rather than to unlaminated materials. An additional laminated layer can then be formed about the base 144 in manners such as described above, such that the base 144 is embedded in the second lamination layer. The foregoing methods may also be used at other positions of the socket 72 other than the position depicted in FIG. 1. For example, in some implementations, the base 144 may be positioned closer to a proximal end of the socket 72.

Figure 19A:
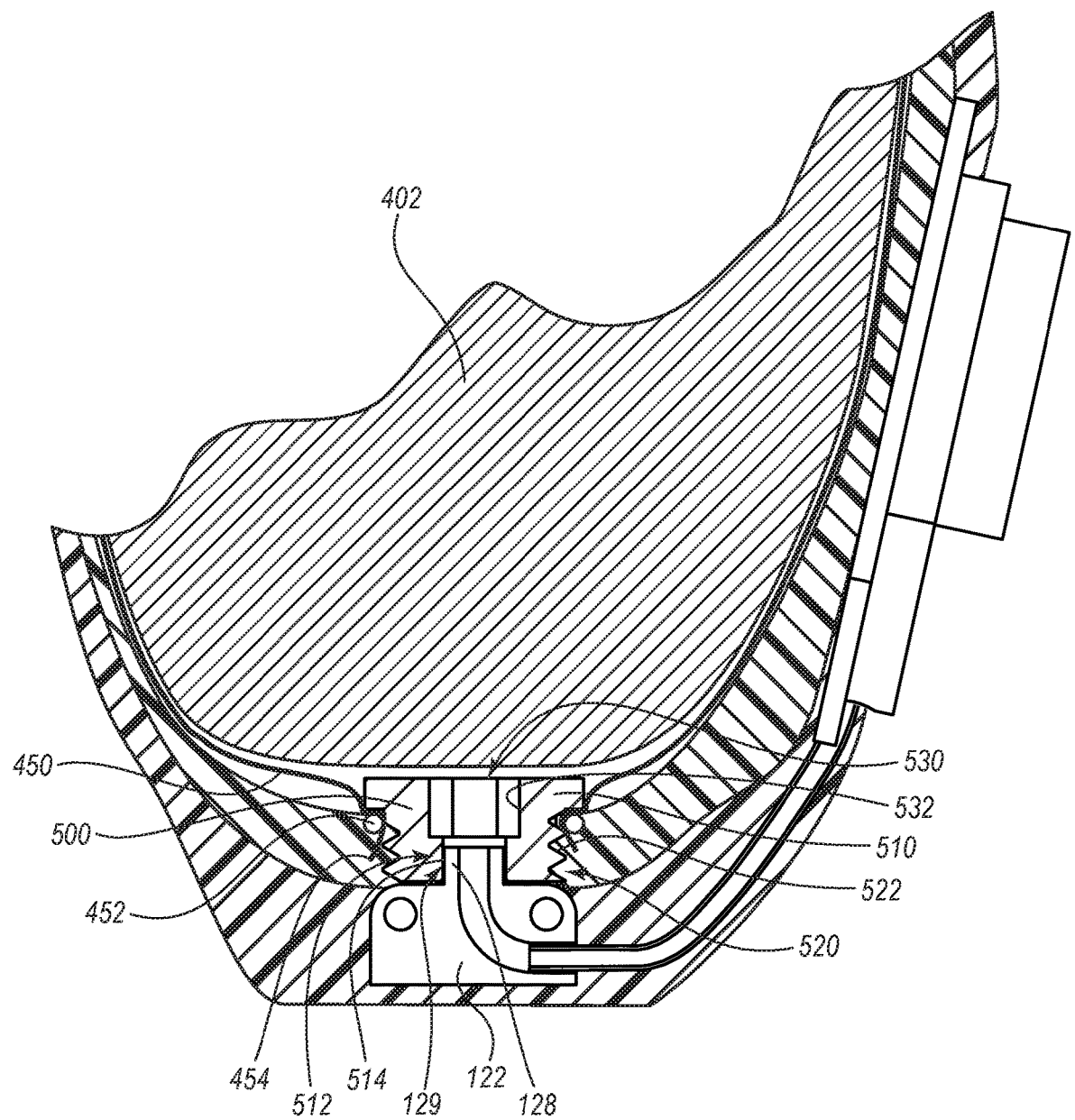
FIGS. 19A and 19B are partial cross-sectional views of various stages of the illustrative method for manufacturing the socket.
Figure 19B:
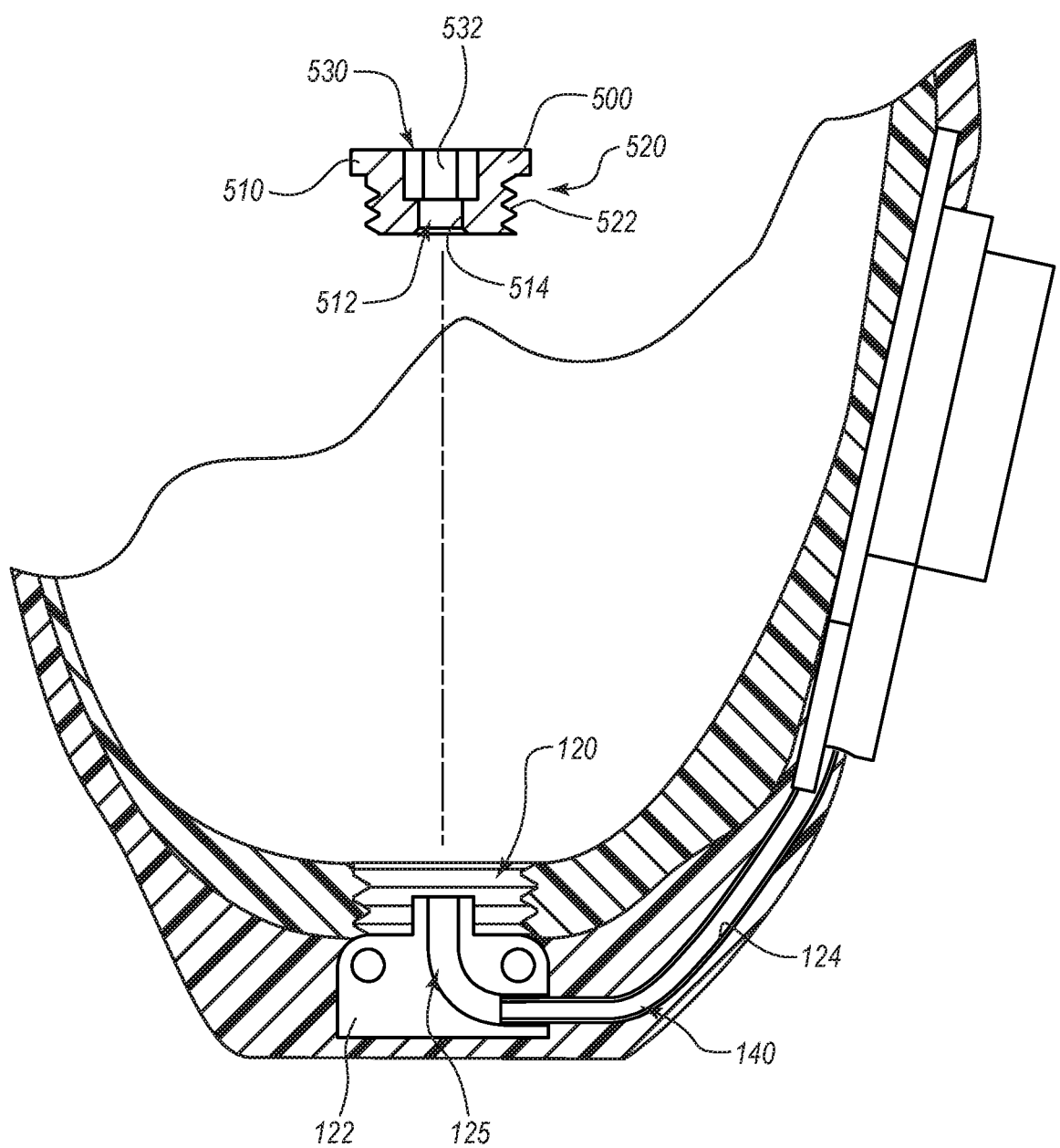

FIGS. 19A and 19B represent separate stages in the formation of an embodiment of a socket 72, such as the socket depicted in FIG. 1. In some instances, one or more of the steps can be performed in conjunction (before, after, or concurrently) with certain of the method steps discussed above with respect to FIGS. 18A-18G.

FIGS. 19A and 19B depict usage of the dummy, blank, or plug 500 to form the recess 120 discussed above. In the illustrated embodiment, the plug 500 defines a shelf 510 that extends radially outwardly about a periphery of a proximal end of the plug 500. As discussed below, the shelf 510 can be useful in tying off a PVA bag in a lamination procedure.

A distal portion of the plug 500 is narrower than the shelf 510. The distal portion can define a backout-assisting interface 520. In the illustrated embodiment, the interface 520 comprises external threading 522. A proximal end of the plug 500 can define a tool interface 530 configured to couple with a tool to assist in backing out the plug 500 after formation of the socket 72. In the illustrated embodiment, the tool interface 530 comprises a female hex socket 532 for interfacing with a hex tool. Any other suitable interface is contemplated.

The distal portion of the plug 500 can define a diverter interface 512 for coupling with the connection interface 129 of the diverter 122. In the illustrated embodiment, the diverter interface 512 comprises a substantially cylindrical region 514 that is configured to engage the boss 128 of the diverter 122 in a friction fit. The engagement can yield a fluid-tight seal, in some arrangements. Other suitable cooperating interfaces 129, 512 are possible. For example, in some embodiments, the plug 500 can engage the boss 128 via a threaded coupling. In other or further embodiments, an o-ring or other seal is used to form a seal between the plug 500 and the diverter 122.

With reference to FIG. 19A, in forming the socket 72, the proximal end of the plug 500 can be positioned adjacent to the distal end of the mold 402 that represents the residuum. Thereafter, a barrier layer 450, such as a PVA bag, can be placed over the plug 500 and the mold 402. The bag 450 can be tied off in any suitable manner, such as via a string or cable 452. In some arrangements, an end of the bag 450 can be cut, thus leaving a free distal end 454 that can be incorporated into the socket wall 73.

In some embodiments, the diverter 122 is coupled to the plug 500 at any suitable stage prior to the introduction of laminating material over the layup. The coupling 500 between the plug 500 and the diverter 122 can prevent laminating material from entering the passageway 125 of the diverter 122 or the duct 140 of the conduit 124 (see FIG. 19B).

With reference to FIG. 19B, after the lamination is completed, the plug 500 can be removed from the socket 72. Removal of the plug 500 yields the recess 120 and also provides access to the passageway 125 of the diverter 122 or the duct 140 of the conduit 124.

Figure 20:
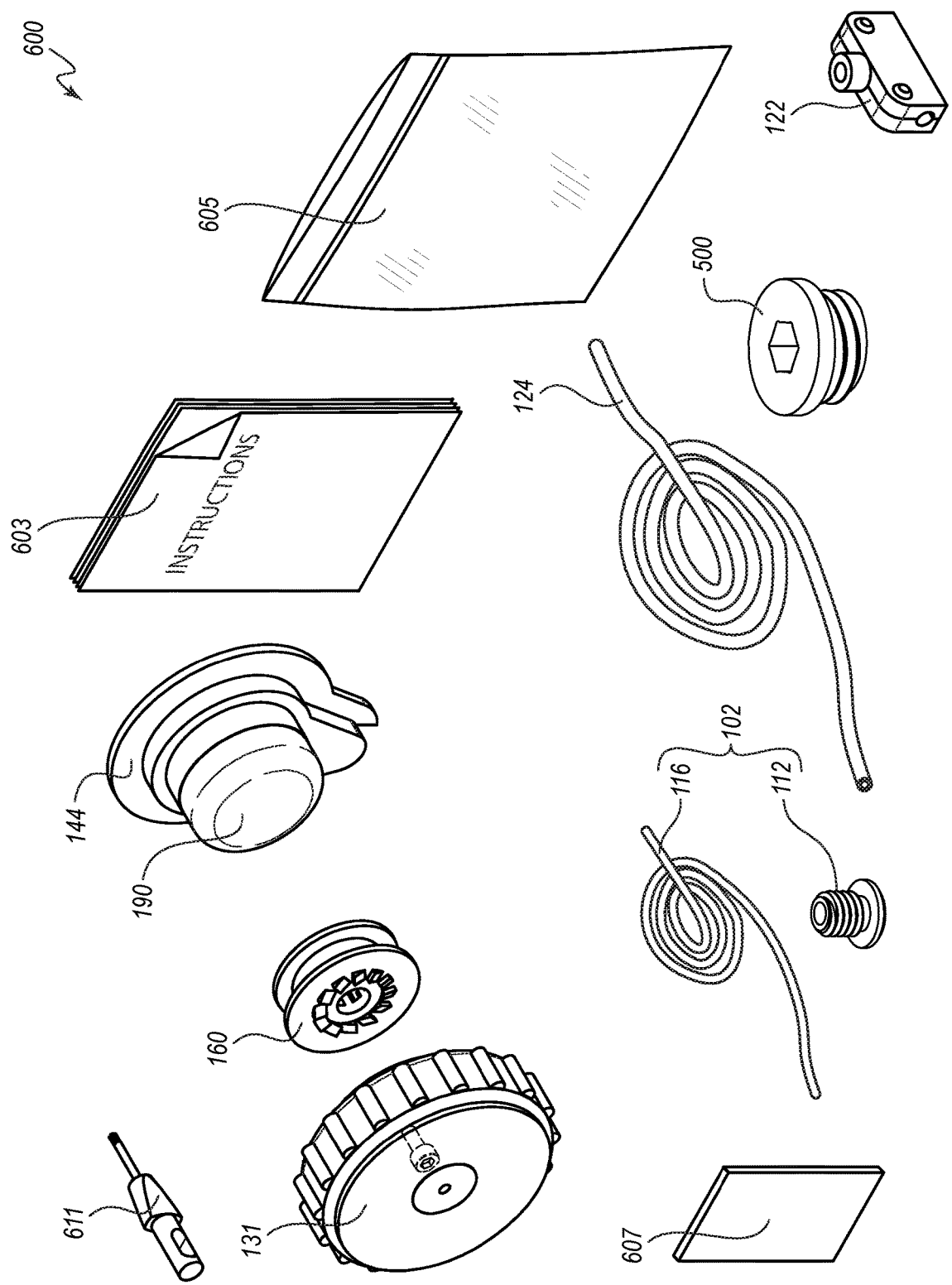
FIG. 20 is a perspective view of an embodiment of a kit that is configured to be used in the manufacture of a socket.

FIG. 20 illustrates an embodiment of a kit 600 that includes materials for use in a lamination procedure, such as the lamination procedures described above, or in other suitable procedures for forming a socket, such as thermoforming methods (which can yield a socket such as depicted in FIG. 22). The kit 600 can include any suitable combination of the following components: the various elements of the tightening device 106, including the spool 160, the base 144, and the knob 131; the dummy 190, which can either be provided individually or in a coupled arrangement with the base 144; the lanyard 102, which can include the tensioning line 116 and the connector 112 in a coupled or decoupled state; the diverter 122; the conduit 124; the plug 500; an adhesive 607, which can be used in placement of the base 144 of the tightening device 106; and instructions 603. Fewer or more items may be included in the kit 600. For example, in some implementations, the adhesive 607 may be omitted. In other or further implementations, a tool 611 for use in assembling or disassembling the tightening device 106 may also be included in the kit 600.

The instructions 603 can include directions for performing any and/or all of the steps of a method for creating a socket that includes a lanyard suspension system, such as any of the procedures or sub-processes thereof discussed above and/or below. In other or further embodiments, the instructions 603 may provide directions for accessing such directions. For example, the instructions may list a web address, a mailing address, and/or a telephone number that can be used to locate instructions for preparing a socket. One or more of the foregoing items can be included in and/or on (e.g., in the case of the instructions) packaging 605 for the kit. Any suitable form of packaging 605 is contemplated.

Figure 21:
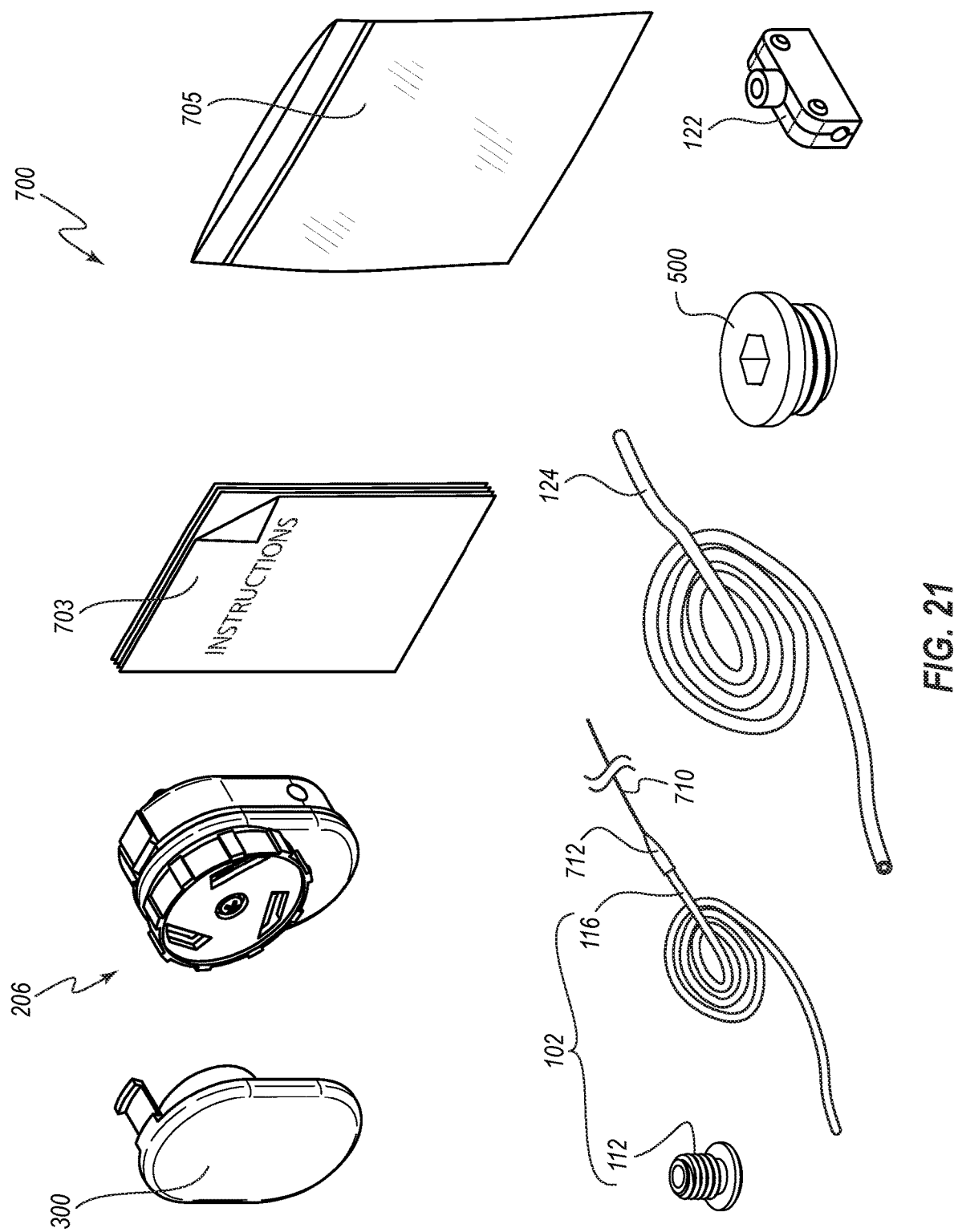
FIG. 21 is a perspective view of another embodiment of a kit that is configured to be used in the manufacture of a socket.

FIG. 21 illustrates another embodiment of a kit 700 that includes materials that can be used in a socket formation procedure, such as those described above. The kit 700 can include any suitable combination of the ratcheting device 206; the dummy 300; the lanyard 102, including a tensioning line 116 and a connector 112; a diverter 122; a conduit 124; a plug 500; and instructions 703, any or all of which can be contained in packaging 705. In some instances, the ratcheting device 206 can be a more heavy duty device. It may be configured for use with a different tensioning line 116 that may be wider and/or stronger. The tensioning line 116 may be a flexible material or cord that can benefit from a relatively stiff feeder 710 for threading the tensioning line 116 through the conduit 124. The feeder 710 can comprise a wire or other elongated stiff member, and may be referred to as a threading wire. In the illustrated embodiment, the feeder 710 comprises a threading wire that is attached to the tensioning line 116 via any suitable connection 712. After threading of the tensioning line 116, the feeder 710 and the connection 712 can be cut from the tensioning line 116. In other embodiments, the feeder 710 can define an eyelet at a proximal end thereof through which the tensioning line 116 may be threaded for temporary attachment.

In some embodiments, the kits 600, 700 may be used either for retrofitting an existing socket or for creating a new socket. In some embodiments, the kits 600, 700 can include mounting hardware, adhesives, and or attachment devices of any suitable variety by which various components may be attached to the socket after formation of the socket, rather than being incorporated into a wall of the socket.

As previously mentioned, in some instances, the dummies 190, 300 may be used in a vacuum forming technique or thermoforming technique. In one example, a lamination dummy is constructed as a lid to seal off the inner portions of the tightening mechanism to protect them during the lamination process. A flange or skirt portion of the base of the tightening mechanism may laminated between layers in the socket. In other embodiments, the flange portion of the base may function as a stop lip on vacuum formed socket. The flange portion can permit increased tension applied on an outer surface of the socket without pulling the tightening mechanism out of the socket.

Figure 22A:
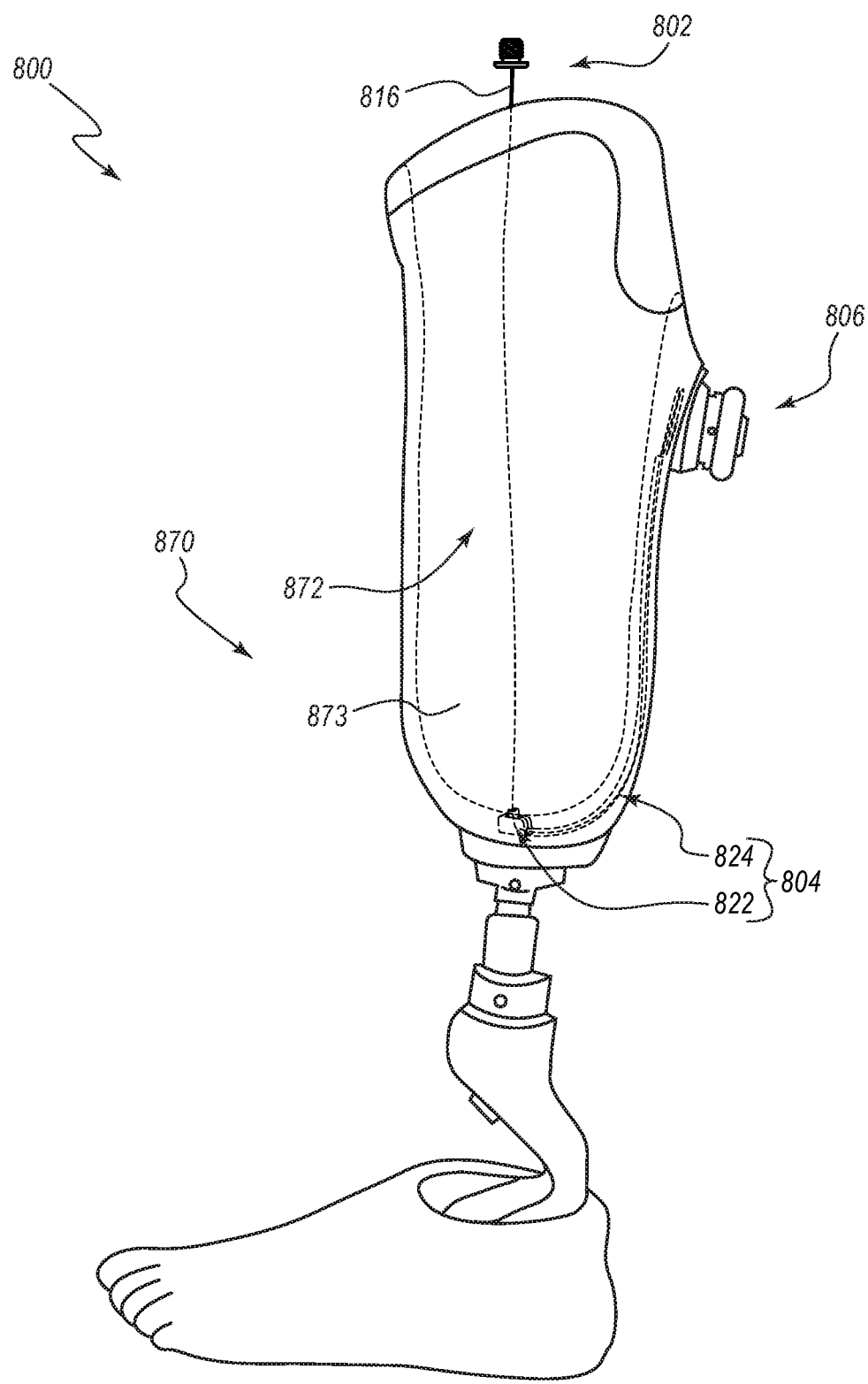
FIG. 22A is a perspective view of another embodiment of a prosthetic system for use with a residuum, the prosthetic system including another embodiment of a socket having another embodiment of a lanyard suspension system.

FIG. 22A depicts an embodiment of a prosthetic system 800 that includes a prosthetic device 870 that can be used with a liner, such as the liner 60 (FIG. 1). The prosthetic system 800 can include a socket 872 having a sidewall 873 that is formed in a different manner than the laminated sidewall 73. For example, the sidewall 873 can be vacuum formed or thermoformed, and may comprise a thermoformed plastic. Otherwise, fabrication methods for the socket 872 are similar to those discussed above and below, and can employ the plug 500 and/or the dummies 190, 300. As with the system 100, the system 800 can include a lanyard suspension system 801, which can include a lanyard 802, a guide path 804, and a tightening mechanism 806. In some embodiments, one or more of these components are integrated into the sidewall 873 of the socket 872. In other or further embodiments, one or more of the components may be coupled to the sidewall 873 in any other suitable manner, such as via one or more of adhesive, fasteners, or other suitable mechanisms. For example, in some embodiments, the tightening mechanism 806 may be attached to the sidewall 873 via one or more fasteners (e.g., screws, bolts, rivets). In the illustrated embodiment, a diverter 822 and a conduit 824 are incorporated into at least a distal end of the socket 872.

Figure 22B:
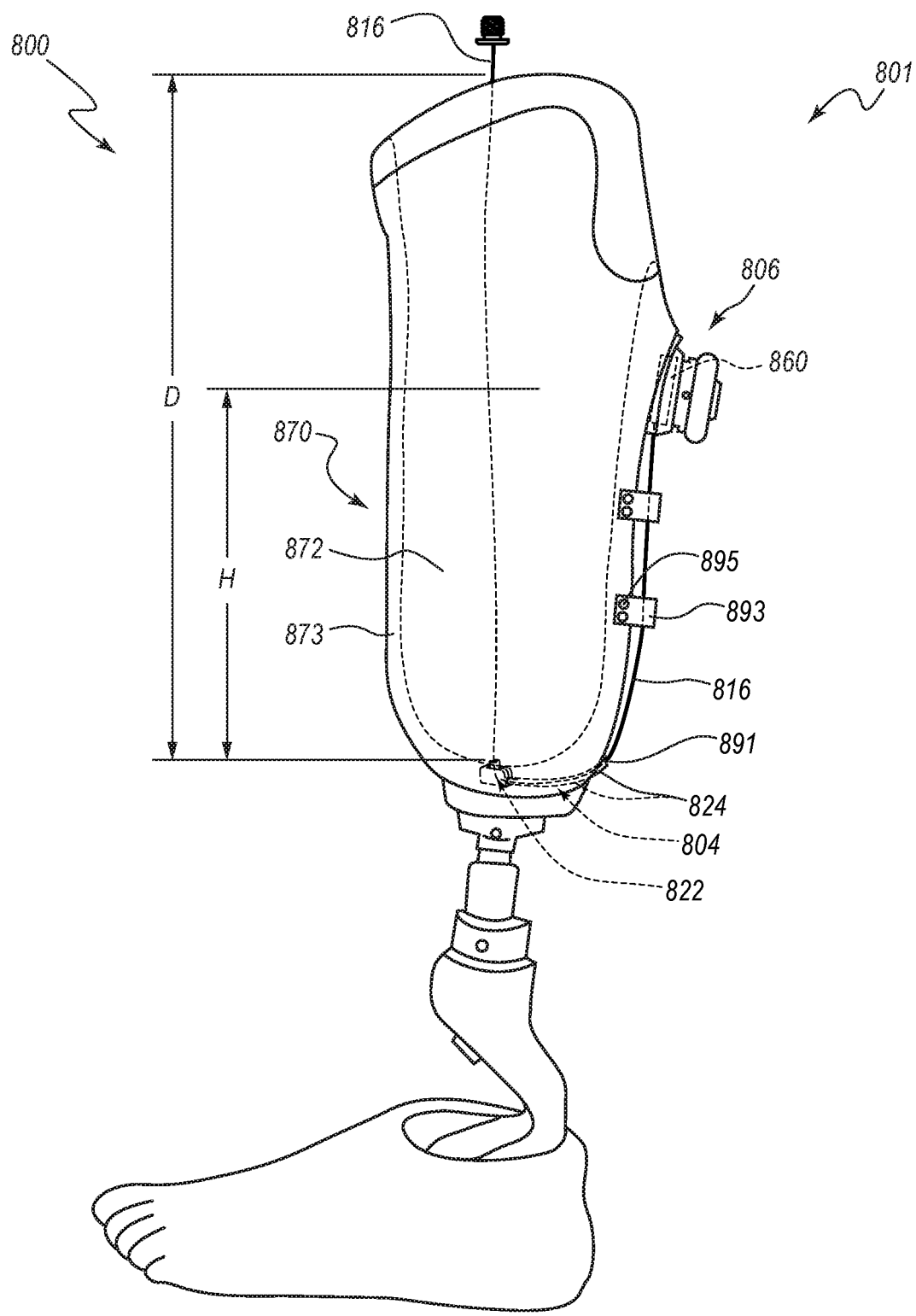
FIG. 22B is a perspective view of another embodiment of a prosthetic system for use with a residuum, the prosthetic system including another embodiment of a socket having another embodiment of a lanyard suspension system.

FIG. 22B depicts another embodiment of a prosthetic system 801 that includes a prosthetic device 870 for use with a liner. The prosthetic system 800 includes a socket 872 having a sidewall 873. The system 801 includes a guide path 804 for a tensioning line 816. The guide path 804 differs from the guide path 104 discussed above (FIG. 1-3) in certain respects.

For example, with reference to FIGS. 1-3, the illustrated guide path 104 is substantially enclosed along an entire length thereof. That is, the passageway 125 is encompassed along a full length thereof by the diverter 122, and the duct 140 is encompassed along a full length thereof by the conduit 124. Moreover, in the illustrated embodiment, the guide path 104 is fully embedded within the wall of the socket 72. That is, the socket wall 73 fully encompass the guide path 104 along a full length thereof.

In various embodiments, an enclosed guide path 104, or a portion thereof, may have a maximum inner diameter that is greater than a maximum outer diameter of the tensioning line by a specific amount. For example, in various embodiments, the inner diameter of the guide path 104 is greater than the outer diameter of the tensioning line 116 by a factor within a range of from about 1.1 to about 4, from about 1.25 to about 4, or from about 1.33 to about 4; is no less than about 1.1, 1.2, 1.3, 1.5, or 2; or is no greater than about 2, 3, or 4.

With reference again to FIG. 22B, the guide path 804 is enclosed along only a portion thereof and only a portion of the guide path 804 is embedded within the wall 873 of the socket 872. In the illustrated embodiment, an exit port of the diverter 822 is coupled with a conduit 824. Only a portion of the conduit 824 is embedded in the wall 873 of the socket 872. A free end 891 of the conduit 824 is at an exterior of the socket 872. Accordingly, the tensioning line 816 is exposed to an environment at the exterior of the socket 872. Moreover, the guide path 804 includes guides 893 that are positioned at the exterior of the socket 872. The guides 893 encompass only small portions of the tensioning line 816. The guides 893 may be fastened to the socket 872 in any suitable manner, such as via fasteners 895 (e.g., rivets).

In still other embodiments, the tensioning line 816 may be enclosed along no portion thereof and/or no portion of the guide path 104 may be embedded within the wall of the socket 872. For example, in some embodiments, the diverter 122 may be embedded in the socket 872, or positioned at an exterior thereof, and defines an exit port that is not coupled to a conduit and that feeds directly to an exterior of the socket 872. Embodiments may not include guides 895 that fully encompasses the tensioning line.

In various embodiments, a total length of the tensioning line 816 may be selected to provide for a relatively small tightening mechanism 806 (e.g., a small housing portion thereof), while still providing a user a convenient length of line to work with when coupling the liner with the lanyard. The length of the line 816 may be expressed as a ratio relative to a depth D of the socket 872, wherein the depth D is the distance from the proximal-most tip of the socket 872 to the distal-most point of the wall 873 at an interior of the socket 872. In various embodiments, a ratio of the length of the line 816 to the depth D is within a range of from about 1:1 to about 4:1, from about 1:1 to about 3:1, or from about 1:1 to about 2:1; is no less than about 1:1, 1.5:1; 2:1, 3:1, or 4:1; or is no greater than about 1:1, 1.5:1, 2:1, 3:1 or 4:1. In some embodiments, the socket depth D is about 35 centimeters and the length of the tensioning line 816 is about 55 centimeters. In various embodiments, the socket depth D may range from about 15 centimeters to about 54 centimeters. Other arrangements are also contemplated.

In various embodiments, a position of the tightening mechanism 806 may be selected to achieve a desired reachability for a user, and in some instances, may be distanced from the proximal or distal ends of the socket 872. For example, a height H at which a center point of the spool 860 or other gathering region of the tensioning line 816 is positioned above the distal-most point of the wall 873 at the interior of the socket 872 may be selected to be a specific percentage of the depth D. In various embodiments, the height H is within a range of from about 5 to about 95 percent, from about 25 to about 75 percent, or from about 40 percent to about 60 percent of the depth D. In other embodiments, the height H is no less than about 5, 10, 15, 25, 50, or 75 percent of the depth D. Other arrangements are also contemplated.

Many variations of the components discussed herein are possible. For example, where a tightening mechanism includes an actuator (e.g., the actuator 130 of the tightening mechanism 106), the actuator can comprise any suitable actuation interface, such as a knob, lever, button, etc. In various embodiments, the actuator can be actuated in any suitable manner, such as for example, by any suitable movement (e.g., rotation, pushing, pulling, or sliding). It is also noted that the term "tightening" as used herein with respect to the tightening mechanism can refer to the development of increased tension in a tensioning line. The tightening mechanism may also be referred to as an adjustment mechanism.

Figure 23A:
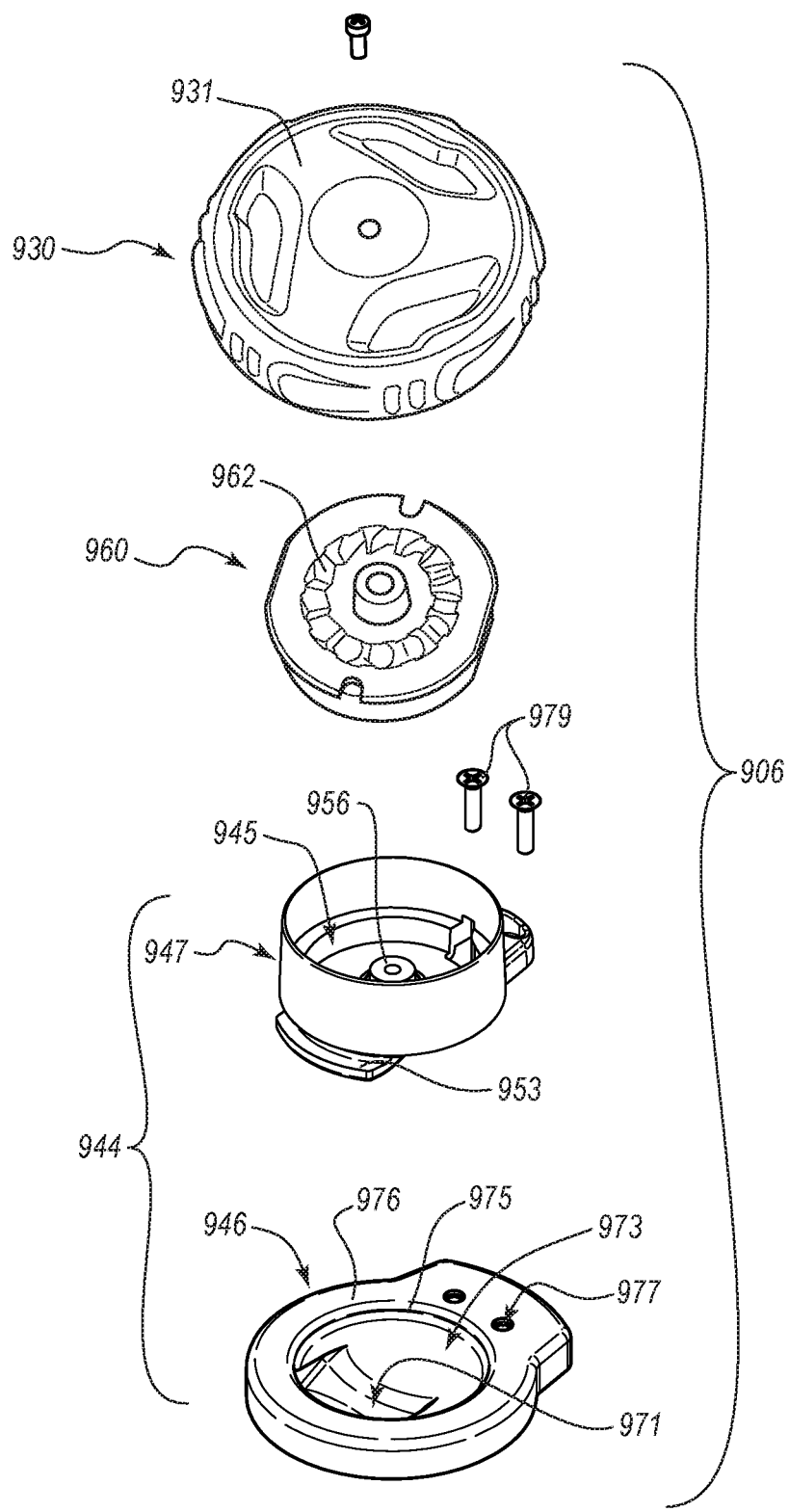
FIG. 23A is an exploded perspective view of another embodiment of a tightening mechanism that is configured to couple with a socket for use with embodiments of a lanyard suspension system.

FIG. 23A depicts another embodiment of a tightening mechanism 906 that can be used with any of the embodiments discussed herein. The tightening mechanism 906 includes a base or base mounting plate 946 and a housing or reel housing 947 that can be selectively coupled with each other and/or selectively decoupled from each other. Stated otherwise, the reel housing 947 is attachable to and/or removable from the base mounting plate 946. Accordingly, in some instances, the base mounting plate 946 may be substantially permanently incorporated into the sidewall of a socket (e.g., laminated into the sidewall). The reel housing 947 can thereafter be coupled to the base mounting plate 946. In other or further embodiments, the reel housing 947 can be decoupled from the base mounting plate 946 as desired—such as for replacement due to wear, malfunction, etc.—without damaging the sidewall of the socket. Thus, one reel housing 947 can be replaced with a different reel housing 947, which may prolong the life of a socket.

In some embodiments, when the reel housing 947 and the base mounting plate 946 are coupled together, they can function substantially the same as the housing or base features 144, 244 discussed above. Accordingly, the reel housing 947 and the base mounting plate 946 may collectively be referred to as a base or housing 944.

In the illustrated embodiment, the base mounting plate 946 defines an insertion recess 971 and a retention recess 973 into which portions of the reel housing 947 can seat. The insertion recess 971 extends downwardly from the retention recess 973. A perimeter of the retention recess 973 is defined by a sidewall 975. The sidewall 975 extends downwardly from an upper face of a flange 976. As further discussed below, in some instances, the flange 976 can have an initial thickness that may be reduced during an installation procedure. For example, the upper face of the flange 976 may be shaved, sanded, ground down, or otherwise removed to reduce the thickness of the flange 976, which can also reduce the depth of the retention recess 973.

In the illustrated embodiment, the flange 976 includes two coupling channels 977 into which fasteners 979 (e.g., screws) can be mounted to secure the reel housing 947 to the base mounting plate 946.

Figure 23B:
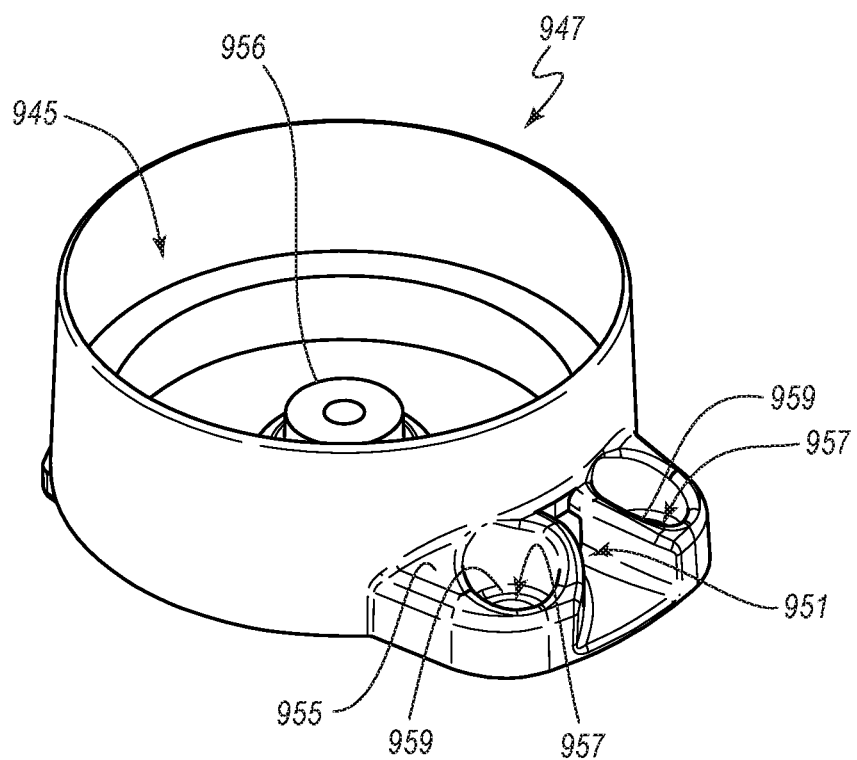
FIG. 23B is another perspective view of a reel housing portion of the tightening mechanism of FIG. 23A.
Figure 23C:
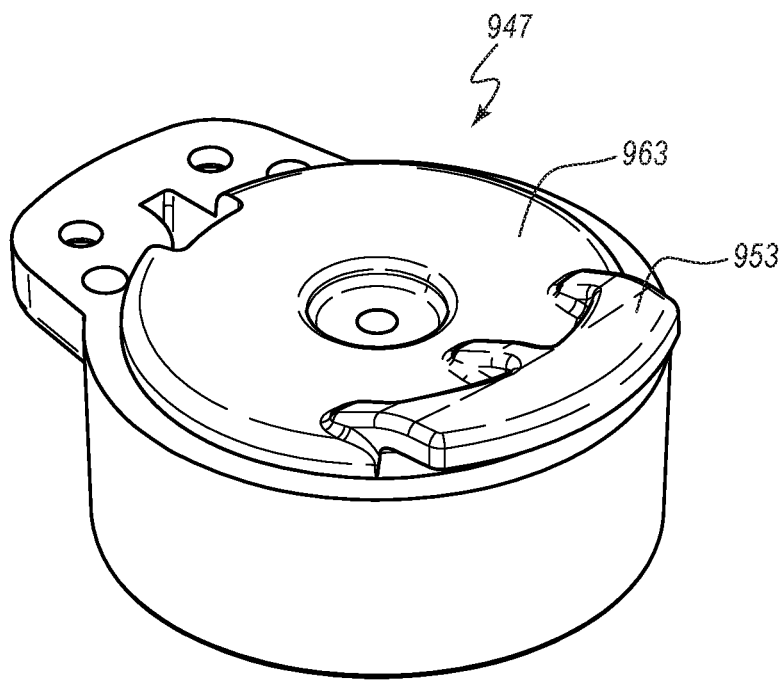
FIG. 23C is another perspective view of the reel housing portion of the tightening mechanism of FIG. 23A.

With reference to FIGS. 23A-23C, the reel housing 947 can include a protrusion, tab, or tongue 953 that is configured to couple with the base mounting plate 946 when advanced into the insertion recess 971. The tongue 953 and the recess 971 can include any suitable coupling interface.

The reel housing 947 can further include a protrusion 955 that includes features for securing the reel housing 947 to the base mounting plate 946. In the illustrated embodiment, the protrusion 955 defines a pair of coupling channels 959 that are configured to align with the coupling channels 977 of the base mounting plate 946. The protrusion 955 further defines shelves 959 against which portions of the fasteners 979 (e.g., screw heads) can press when the fasteners 979 are advanced into the channels 957.

The reel housing 947 can define a retention protrusion 963 that is sized for insertion into the retention recess 973 of the base mounting plate 946. In some instances, it can be desirable for the retention recess 973 to have a sufficient depth to be able to fully receive the retention protrusion 963 therein. Accordingly, it may be desirable to ensure that the sidewall 975 retains a height that is greater than a depth of the retention protrusion 963.

As with other housing portions described herein, the reel housing 947 can define a cavity 945 for receiving a reel 960. The reel housing 947 may further define a post 956 to which the reel 960 is pivotally mounted.

With reference again to FIG. 23A, the reel 960 can include any of the features discussed with respect to other reels herein. For example, in the illustrated embodiment, the reel 960 includes a plurality of teeth 962 that can interact with an actuator 930 to effect tightening of a tensioning line around the spool 960. The actuator 930 may be of any suitable variety, such as previously discussed. In the illustrated embodiment, the actuator 930 comprises a dial 931 that can be rotated to tighten the tensioning line in manners such as those previously discussed. The actuator 930 may also be referred to as a cover, as this component can effectively cover or close the cavity 945 of the reel housing 947 when coupled with the reel housing 947.

Figure 24A:
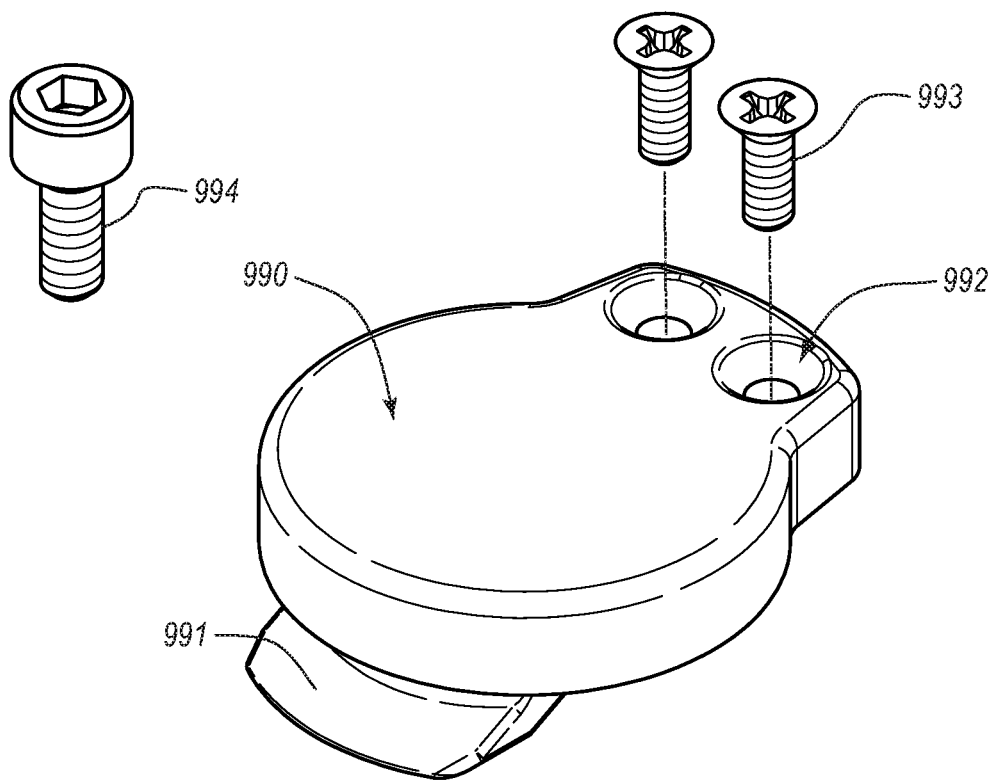
FIG. 24A is an exploded perspective view of an embodiment of a dummy and associated hardware that is compatible for use with the tightening mechanism of FIG. 23A, such as for installation of the tightening mechanism in a socket.
Figure 24B:
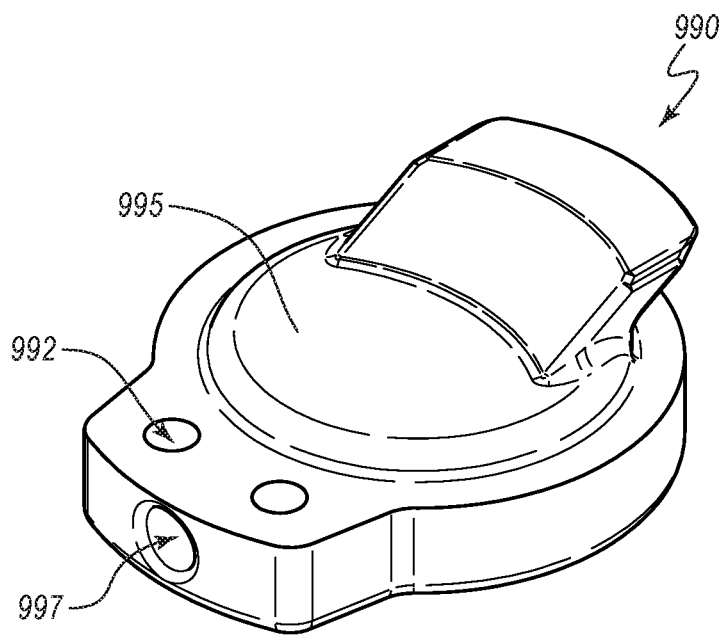
FIG. 24B is another perspective view of the dummy of FIG. 24A.

FIGS. 24A and 24B depict an embodiment of a dummy 990 that can be coupled with the base mounting plate 946 for purposes of installing the base mounting plate 946 in the wall of a socket. For example, the dummy 990 can be used for incorporating the base mounting plate 946 into the wall of a socket during a lamination procedure. The dummy 990 may be formed of any suitable material, such as those previously discussed. For example, in some embodiments, the dummy 990 may be formed of a resiliently flexible material that can deform when under vacuum to form a tight seal with the base mounting plate 946 to prevent lamination material from entering the either of the recesses 971, 973 (FIG. 23A).

The dummy 990 can include a tongue 991 and a retention protrusion 995 that may resemble the tongue 953 and the retention protrusion 963 of the reel housing 947. The tongue 991 and the retention protrusion 995 can be received within the insertion recess 971 and the retention recess 973 of the base mounting plate 946.

The dummy 990 can define coupling channels 992 through which fasteners 993 can be advanced to attach the dummy 990 to the base mounting plate 946. In some instances, rather than using separate fasteners 993, the fasteners 979 (FIG. 23A) may be used with the dummy 990 as well as with the reel housing 947.

In some embodiments, an extraction device 994, such as a bolt, may be used to assist in separating the dummy 990 from the base mounting plate 946. For example, in some embodiments, the extraction device 994 comprises a bolt that has a diameter slightly larger than an outer diameter of the channels 977 of the base mounting plate 946 (FIG. 23A). Upon removal of the fasteners 993 or 979 from the channels 992 of the dummy 990, the extraction device 994 can be advanced through one of the channels 992. When the distal face of the extraction device 994—e.g., a bolt—meets the upper surface of the flange 976 of the base mounting plate 946 (FIG. 23A), continued rotation of the bolt 994 will not advance the bolt into the channels 977 of the base mounting plate 946 due to the size of the bolt. Rather, as the distal tip of the bolt remains flush with the flange 976, the rotation causes the dummy 990 to lift from the base mounting plate 946. Such lifting can facilitate removal of the dummy 990. In some instances, the head of the extraction bolt 994 can be grasped (e.g., by hand or with a tool, such as pliers) and pulled to further effect separation of the dummy 990 and the base mounting plate 946.

The dummy 990 can define a port or recess 997 that is configured to receive an end of a conduit during formation of a socket. For example, an end of a conduit can be inserted into the recess 997 of the dummy 990 during a lamination procedure to inhibit or prevent lamination material from entering into the conduit.

Figure 25A:
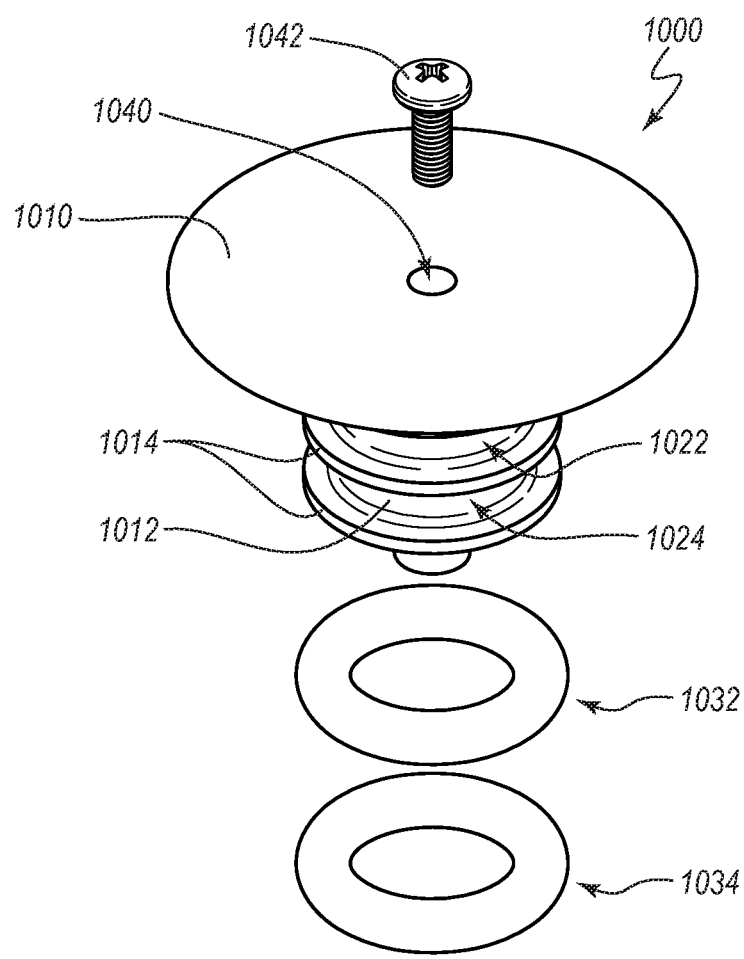
FIG. 25A is an exploded perspective view of an embodiment of a post.
Figure 25B:
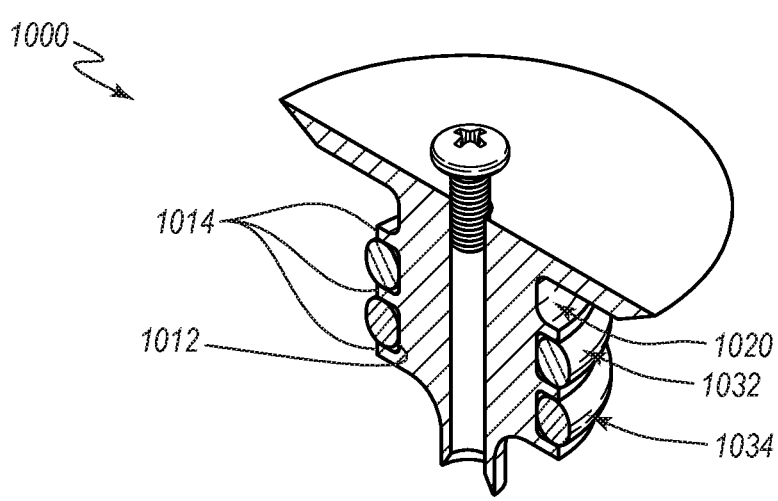
FIG. 25B is a cross-sectional view of the post in an assembled state.

FIGS. 25A and 25B depict an embodiment of a post 1000 that can be used when installing a lanyard system in a socket. The post 1000 may resemble the plug 500 in certain respects, and may also be referred to herein as a plug. The post 1000 can be used, for example, in lamination procedures. In the illustrated embodiment, the post 1000 includes a proximal base 1010 and a shaft 1012 that extends distally from the base 1010. A plurality of annular flanges 1014 extend radially outwardly from the shaft 1012 and cooperate therewith to define a plurality of grooves 1020, 1022, 1024. The groove 1020 can be sized for receiving a layer of barrier material and a coupling element (e.g., tied-off string, thread, cord) for securing the barrier material to the post 1000. Each of the grooves 1022, 1024 can be sized to receive therein a separate sealing element or seal 1032, 1034, respectively. In the illustrated embodiment, the seals 1032, 1034 are elastomeric O-rings. Any other suitable seal is contemplated.

The post 1000 can define a central channel 1040 into which a fastener 1042 can be received. The fastener 1042 can aid in coupling the post 1000 to a model or mold that represents a residuum, such as, for example, a plaster mold or a foam mold. In the illustrated embodiment, the fastener 1042 is a screw or bolt that is advanced into the channel 1040. In other embodiments, the fastener 1042 can comprise an protrusion from the post 1000 that is integrally formed with the post 1000.

Figure 26A:
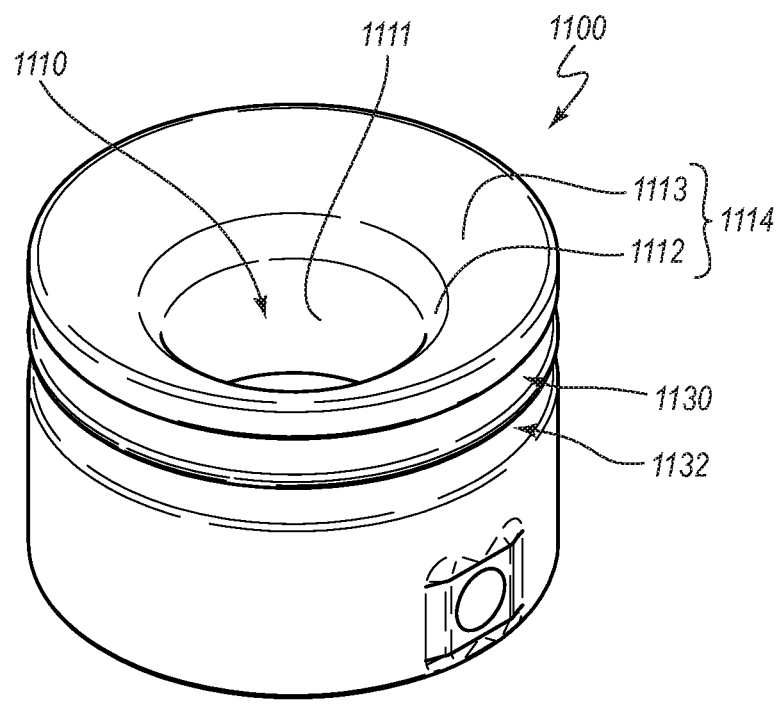
FIG. 26A is a perspective view of an embodiment of a lanyard housing that may, in some instances, be used with the post of FIGS. 25A and 25B.
Figure 26B:
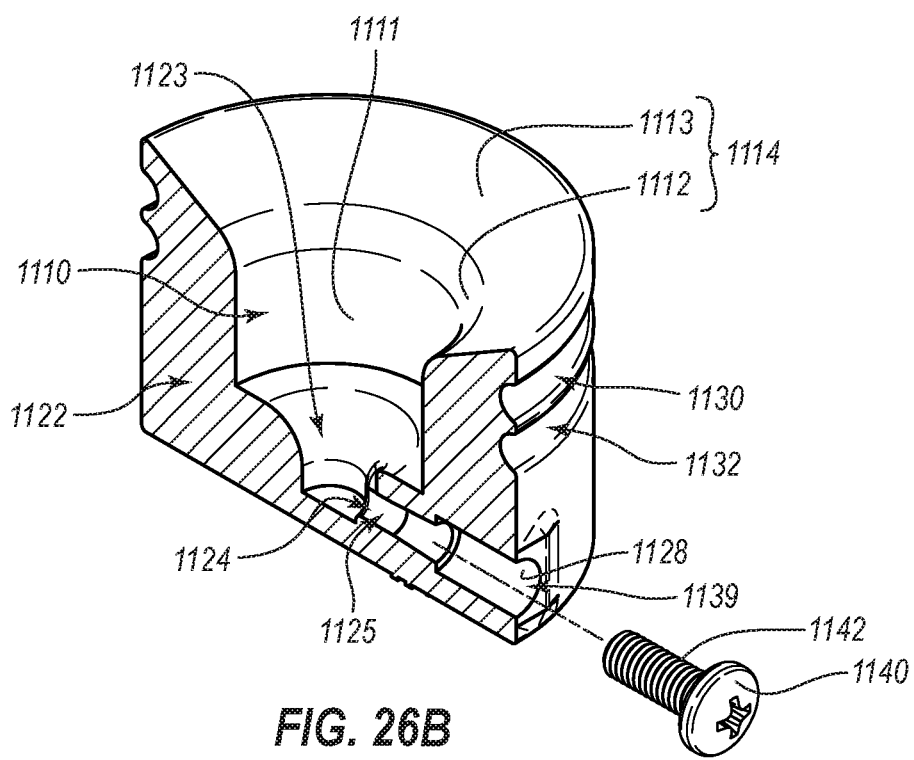
FIG. 26B is a cross-sectional view of the lanyard housing of FIG. 26A.

FIGS. 26A and 26B depict an embodiment of a lanyard housing 1100 that can be used when installing a lanyard system in a socket and/or for interacting with the lanyard system. The lanyard housing 1100 can be used, for example, in lamination procedures. In the illustrated embodiment, the lanyard housing 1100 defines a receptacle 1110 that is sized to receive therein a distal portion of the post 1000. In particular, the lanyard housing 1100 includes a sidewall 1111 that defines the receptacle 1110. In the illustrated embodiment, the sidewall 1111 is substantially cylindrical, and is capable of engaging the sealing members 1032, 1034 of the post 1000 so as to form a fluid-tight seal therewith. The seal thus formed can inhibit or prevent lamination material from entering the lanyard housing 1100 and/or a conduit coupled therewith during a lamination procedure. As discussed further below, the receptacle 1110 can be sized to instead, or additionally, form a fluid-tight seal with a lanyard connector during use of the lanyard.

The upper end of the sidewall 1111 includes a rounded region 1112 that flares outwardly toward a funnel region 1113. As discussed further below, the funnel region 1113 can assist in coupling the lanyard connector into the receptacle 1110. The funnel region 1113 also may permit a portion of the liner 60 to be positioned within the lanyard housing 1100, or otherwise permit the lanyard connector to seat further down within the receptacle 1110 (see FIG. 29V).

At the base of the receptacle 1110 is a diverter portion 1122 that can function similarly to the other diverters discussed above. The diverter portion 1122 includes a recess 1123 that, in the illustrated embodiment, is positioned along a central longitudinal axis of the lanyard housing 1100. A channel, pathway, or passageway 1125 through which a tensioning line may pass is offset from the central longitudinal axis. In particular, an opening 1124 into the passageway 1125 is offset to one side of the recess 1123. In some arrangements, this offset can reduce the strain on a tensioning line as it changes direction from an orientation substantially aligned with the central longitudinal axis of the lanyard housing 1100 to an orientation substantially aligned with a longitudinal axis of the passageway 1125.

In the illustrated embodiment, the diverter portion 1122 changes the direction of the tensioning line through an angle of approximately ninety degrees. Stated otherwise, in the illustrated embodiment, the central longitudinal axis of the lanyard housing 1100 and the longitudinal axis of the passageway 1125 are oriented at ninety degrees relative to one another. In other embodiments, the diverter portion 1122 changes the direction of the tensioning line through an angle: within a range of from about 5 degrees to about 180 degrees, from about 45 degrees to about 180 degrees, or from about 90 degrees to about 180 degrees; that is no less than about 30, 45, 60, 75, 90, 120, 150, or 180 degrees; or that is no greater than about 30, 45, 60, 75, 90, 120, 150, or 180 degrees.

The lanyard housing 1100 can include a conduit port 1139 that includes a connection interface 1128 at which a distal end of a conduit can be coupled. In further embodiments, a plug 1140 may be coupled to the lanyard housing 1100 at the connection interface 1128. In the illustrated embodiment, the plug 1140 comprises a bolt having external threading 1142. The connection interface 1128 comprises internal threading suitable for coupling with the external threading 1142 of the plug 1140. Any other suitable connection interface is contemplated. Moreover, in some instances, the connection interface 1128 may interact with the plug 1140 in a first manner, such as via complementary threading, yet may interact with the conduit in another manner, such as via a friction-fit engagement. The plug 1140 may be used to close the passageway 1125 during lamination.

The lanyard housing 1100 may include further features that can be useful when installing the lanyard housing 1100 in a socket, such as during a lamination procedure. For example, in the illustrated embodiment, the lanyard housing 1100 defines a plurality of grooves 1130, 1132 at an external surface thereof. The grooves 1130, 1132 may be sized to receive at least a portion of one or more materials during layup of the socket. Moreover, the grooves 1130, 1132 may provide useful gripping surfaces when using a coupling element (e.g., tied-off string, thread, cord) for securing the one or more layers of layup material to the lanyard housing 1100.

The lanyard housing 1100 may be formed of any suitable material, including any of the materials discussed above with respect to the diverter 122. For example, in some embodiments, the lanyard housing 1100 is formed of Delrin®. In some embodiments, it can be desirable for at least the diverter portion 1122 of the lanyard housing 1100 to be substantially rigid. It may be desirable for the inner surfaces of the diverter portion 1122 to be smooth, so as to reduce wear on the tensioning line.

Figure 27A:
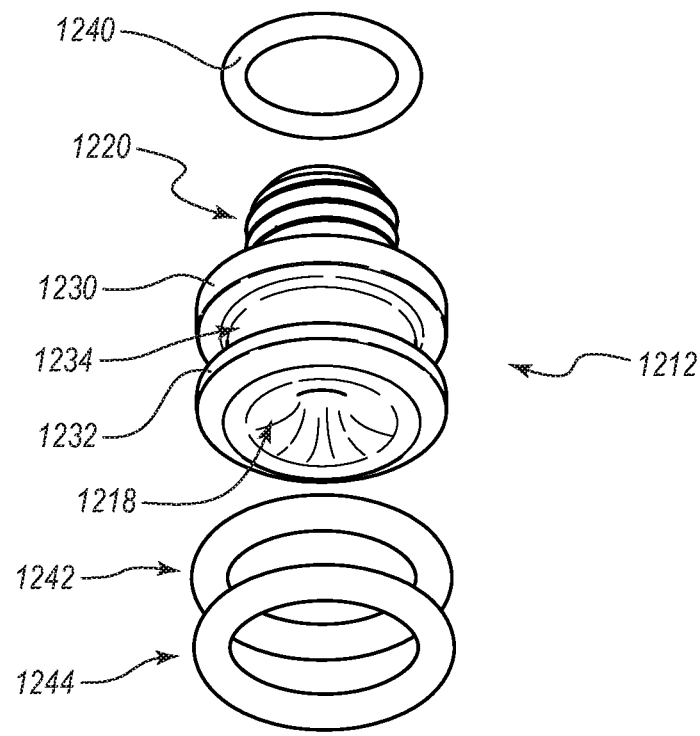
FIG. 27A is an exploded perspective view of an embodiment of a connector portion of a lanyard.
Figure 27B:
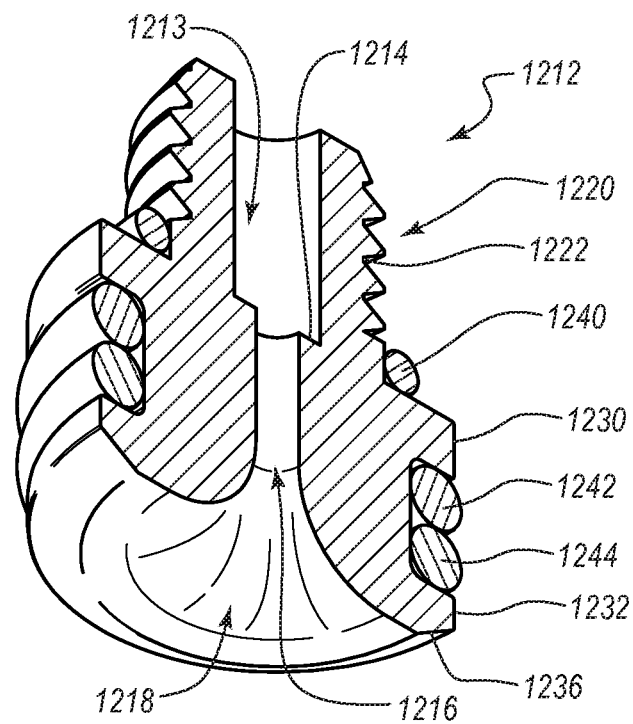
FIG. 27B is a cross-sectional view of the connector portion of the lanyard in an assembled state.

FIGS. 27A and 27B depict an embodiment of a lanyard connector 1212 that can be used with any of the lanyard systems disclosed herein. The lanyard connector 1212 includes a counterbore, at the base of which is an annular ledge 1214 configured for retaining a proximal end of a tensioning line. For example, in some embodiments, the proximal end of the tensioning line is knotted, and the knot is received within the counterbore 1213 and retained from passing through a channel 1216 by the annular ledge 1214. Any other suitable mechanism for coupling the tensioning line to the connector 1212 is contemplated.

A distal end of the passageway 1216 is flared so as to substantially define a trumpet shape. The flared end 1218 can help route the tensioning line to the opening 1124 of the passageway 1125 of the lanyard housing 1100 (FIG. 26B) and reduce strain on the tensioning line as the connector 1212 is pulled into the receptacle 1110 of the lanyard housing 1100.

The In the illustrated embodiment, the lanyard connector 1212 includes two annular flanges 1230, 1232 that extend radially outwardly and cooperate to define a grooves 1234. The groove 1234 can be sized to receive therein one or more sealing elements or seals 1242, 1244. In the illustrated embodiment, the seals 1242, 1244 are elastomeric O-rings. Any other suitable seal is contemplated. The seals 1242, 1244 can be sized to form a fluid-tight seal with the sidewall 1111 of the lanyard housing 1100 when the lanyard connector 1212 is drawn into the receptacle 1110 of the lanyard housing 1100.

In some embodiments, the connector 1212 includes a sealing member or seal 1240, such as an O-ring. The seal 1240 can be configured to form a fluid-tight seal with a distal end of a liner connector, such as the liner connector 64 (FIG. 5), to which the connector 1212 attaches. For example, the connector 1212 can include a connection interface 1220 for attachment to a liner connector, such as the liner connector 64. In the illustrated embodiment, the connection interface 1220 is external threading 1222 that is complementary to internal threading of the liner connector 64. When the connectors 1212, 64 are threaded together, a distal end of the connector 64 can compress the seal 1240 against an upper face of the upper flange 1230, thereby forming a fluid-tight seal. This fluid-tight seal can prevent air from entering into the passage 1216 vie the proximal end of the connector 1212.

Although the connection interface 1220 in the illustrated embodiment comprises threading 1222, any other suitable connection interface is contemplated. For example, in various embodiments, the connectors 1212, 64 can be coupled via one or more fasteners of any suitable variety, including without limitation one or more of buckles, straps, snaps, hook-and-pile fasteners (e.g., Velcro®), etc. In other or further embodiments, the connection interface can comprise a magnetic connection interface. For example, in various embodiments, any of a variety of magnetic coupling arrangements available from Fidlock® may be used.

In some embodiments, the connector 1212 includes a chamfered or otherwise angled rim 1236. The rim 1236 can interface with the funnel region 1113 of the lanyard housing 1100 to guide the connector 1212 into the receptacle 1110 of the lanyard housing 1100.

FIG. 28 illustrates an embodiment of a kit 1300 that includes materials for use in a socket-formation procedure. For example, in some embodiments, the kit 1300 may be used for thermoformed/vacuum formed sockets (see, e.g., FIG. 22). In other embodiments, the kit 1300 may be used for lamination procedures, such as one-stage or two-stage lamination procedures.

The kit 1300 can include any suitable combination of the following components: the post 1000; the lanyard housing 1100; the plug 1140 for use with the lanyard housing 1100; the various elements of the tightening device 906, including the base mounting plate 946, the reel housing 947, the fasteners 979, the reel 960, and the actuator 930; the dummy 990; the dummy extraction device 994; a lanyard 1302, which can include the connector 1212 and a tensioning line 1316; a conduit 1324; a kink-resistant member 1330, such as a spring; a line feeder 1310; and instructions 1303. Further, in the illustrated embodiment, the kit 1300 includes a tool 1308 for use in assembling or disassembling the tightening device 906, such as for mounting or removing the actuator 930. In various embodiments, the kit 1300 may include more or fewer components than those depicted in FIG. 28.

The instructions 1303 can include directions for performing any and/or all of the steps of a method for creating a socket that includes a lanyard suspension system, such as any of the procedures or sub-processes thereof discussed above and/or below. In other or further embodiments, the instructions 1303 may provide directions for accessing such directions. For example, the instructions may list a web address, a mailing address, and/or a telephone number that can be used to locate instructions for preparing a socket. One or more of the foregoing items can be included in and/or on (e.g., in the case of the instructions) packaging 1305 for the kit. Any suitable form of packaging 1305 is contemplated.

Figure 29B:
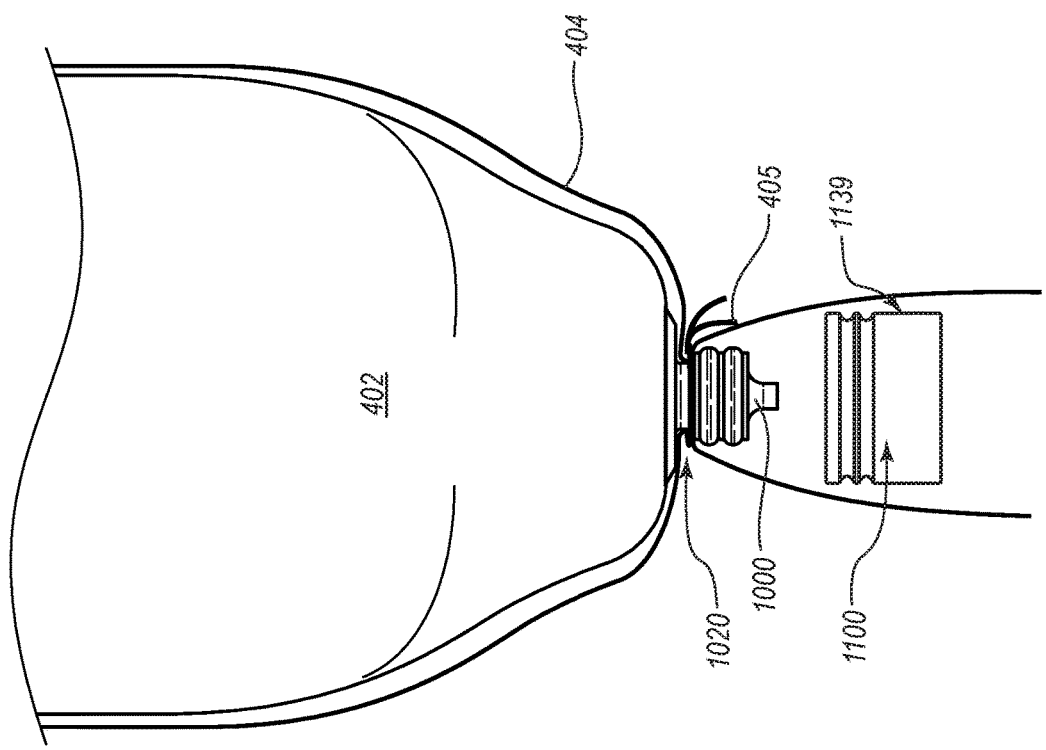
FIG. 29B is an elevation view of the model and post of FIG. 29A with a barrier layer, such as a PVA bag, mounted to the post, wherein the lanyard housing is being moved into proximity to the post to be coupled therewith.
Figure 29A:
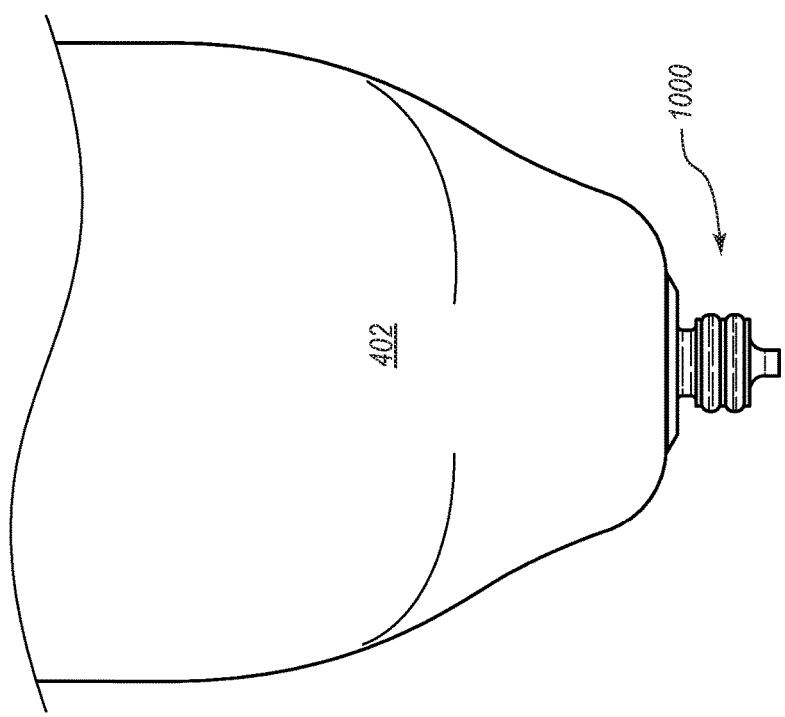
FIGS. 29A-29V are views of different stages in an illustrative method for manufacturing a socket using the components of the kit of FIG. 28.
Figure 29D:
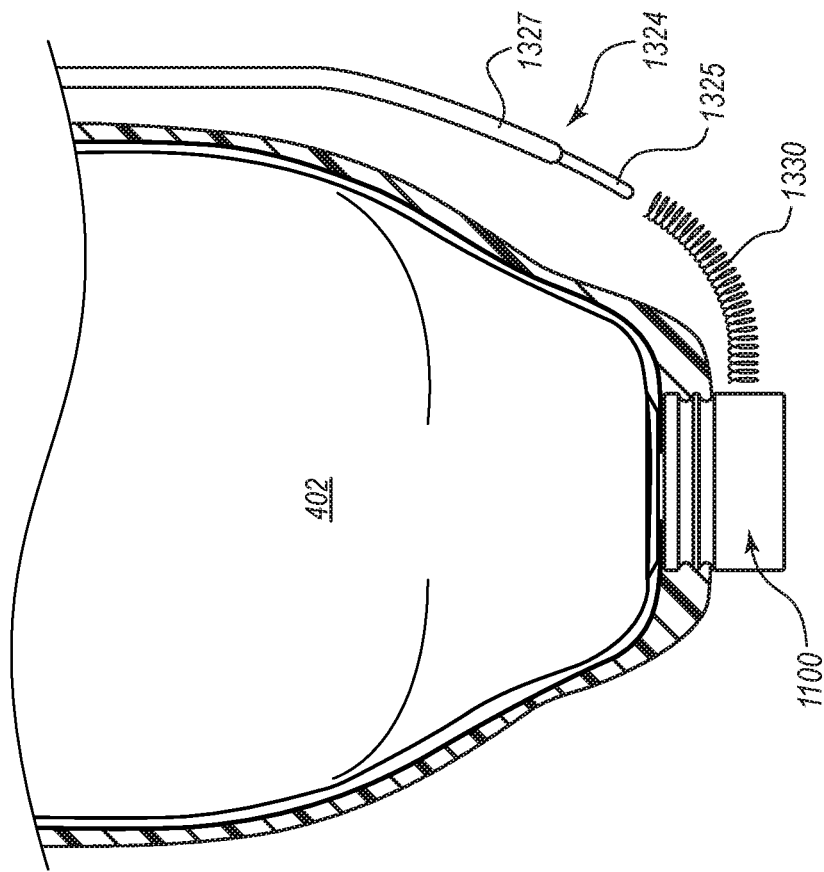
FIG. 29D is an elevation view such as that of FIG. 29C that depicts a conduit and a kink-resistant member in close proximity to the lanyard housing.
Figure 29C:
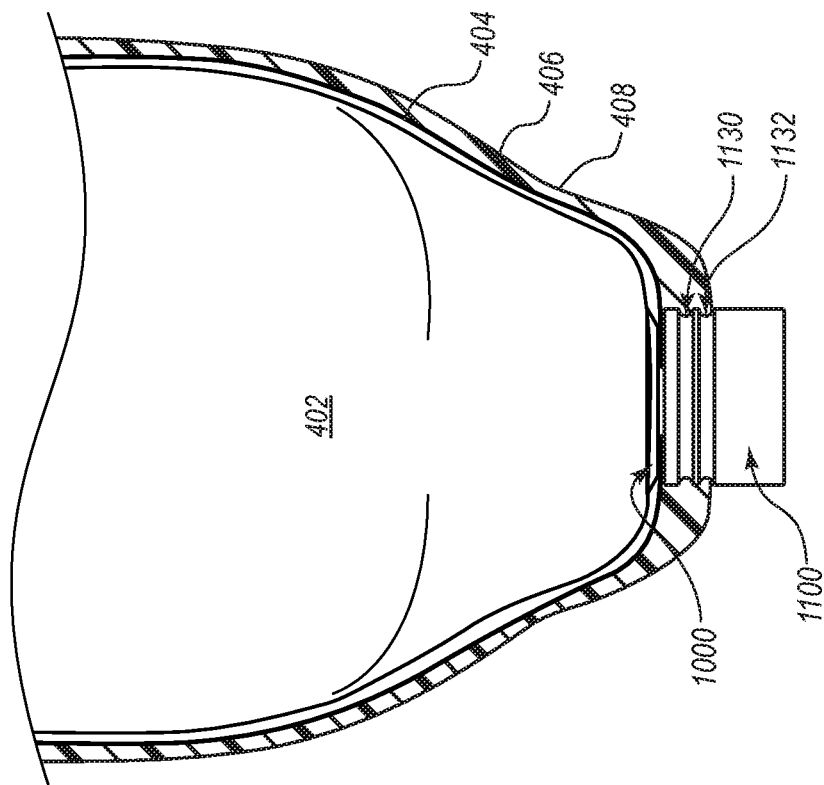
FIG. 29C is an elevation view of the model with the lanyard housing mounted thereon via the post that further depicts multiple layers of material (shown in cross section) that are positioned over the model and are coupled to an external surface of the lanyard housing.
Figure 29G:
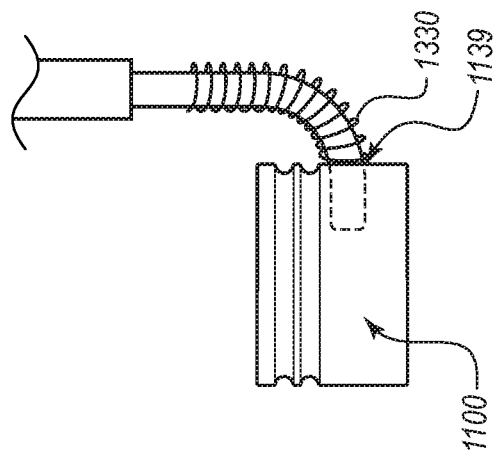
FIG. 29G is another detailed elevation view that omits certain features depicted in FIG. 29D and shows a distal end of the kink-resistant member being coupled with the lanyard housing.
Figure 29F:
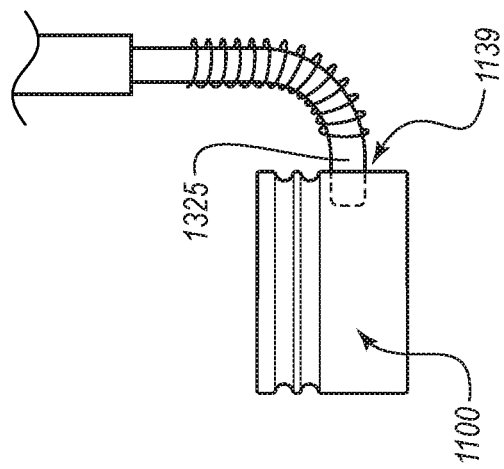
FIG. 29F is another detailed elevation view that omits certain features depicted in FIG. 29D and shows the distal end of the conduit being coupled with the lanyard housing.
Figure 29E:
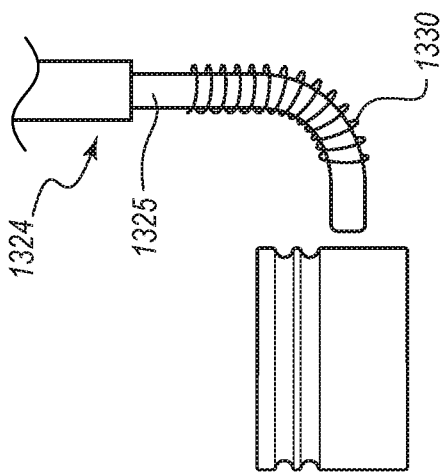
FIG. 29E is a detailed elevation view that omits certain features depicted in FIG. 29D and shows the kink-resistant member being coupled with a distal end of the conduit.
Figure 29L:
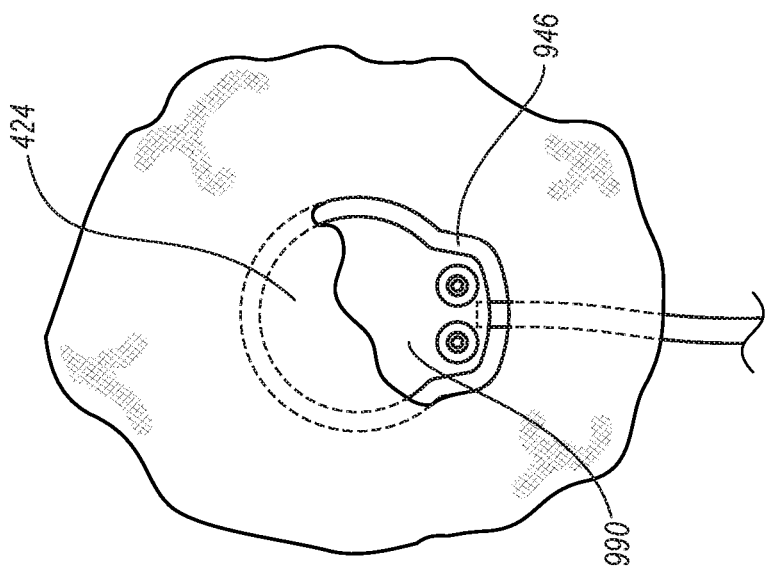
FIG. 29L is a detailed elevation view that omits certain features depicted in FIG. 29K and shows the use of a grinding tool to remove a portion of the lamination material to expose the mounting-plate-and-dummy assembly.
Figure 29K:
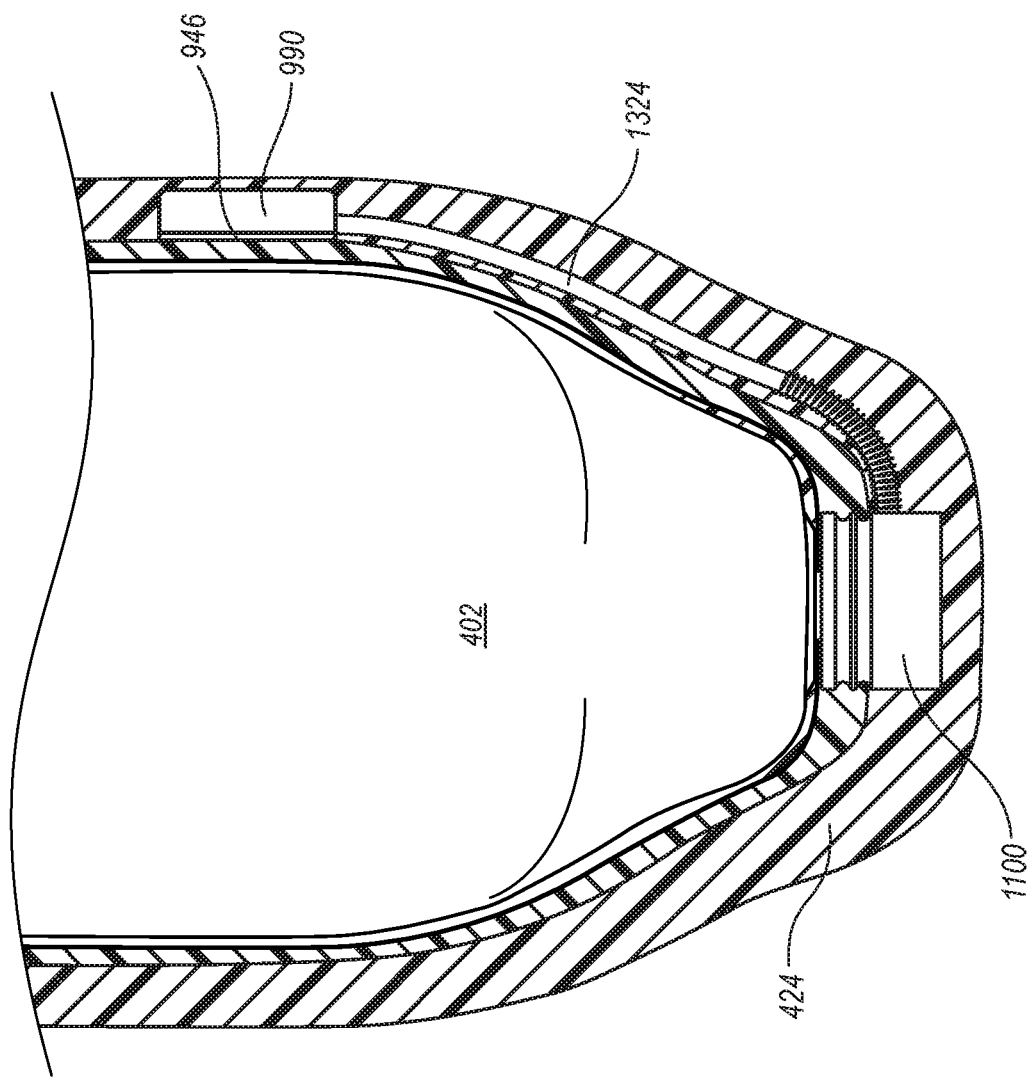
FIG. 29K is an elevation view such as that of FIG. 29C that depicts the lamination of a further layer of material over the lanyard housing, the conduit, and the mounting-plate-and-dummy assembly.
Figure 29N:
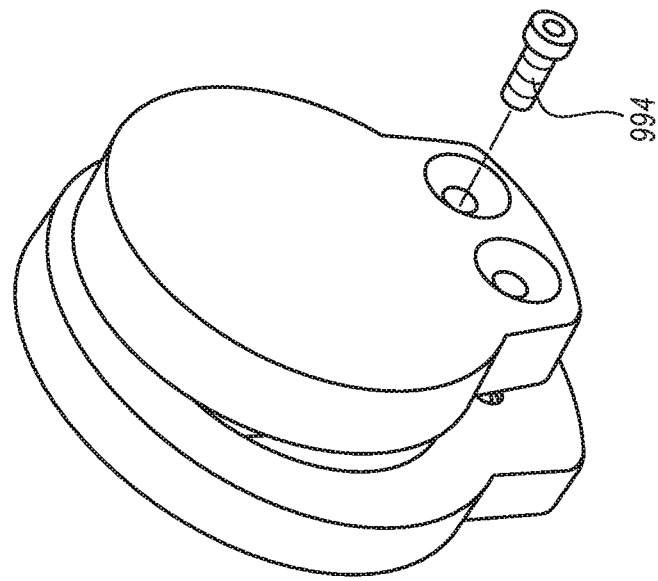
FIG. 29N is a detailed perspective view that omits certain features depicted in FIG. 29K and depicts the advancement of a dummy extraction bolt through the dummy to effect separation of the dummy from the base mounting plate.
Figure 29M:
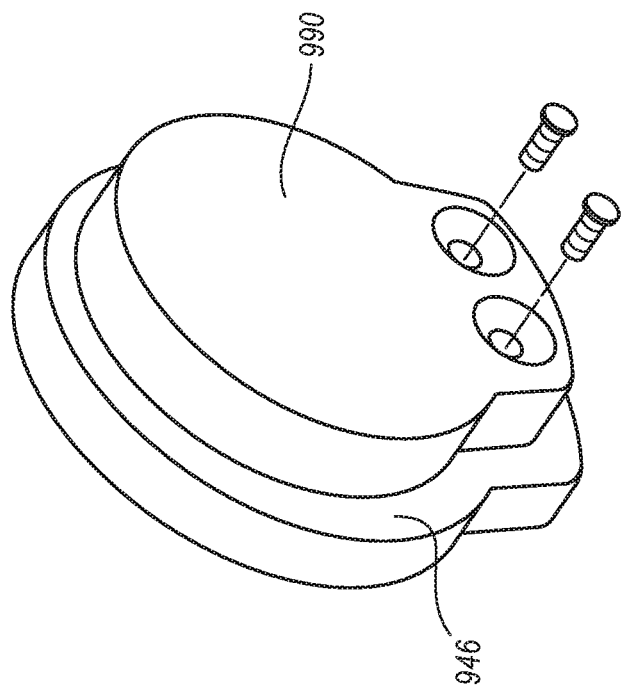
FIG. 29M is a detailed perspective view that omits certain features depicted in FIG. 29K and shows the removal of fasteners from the mounting-plate-and-dummy assembly.
Figure 29P:
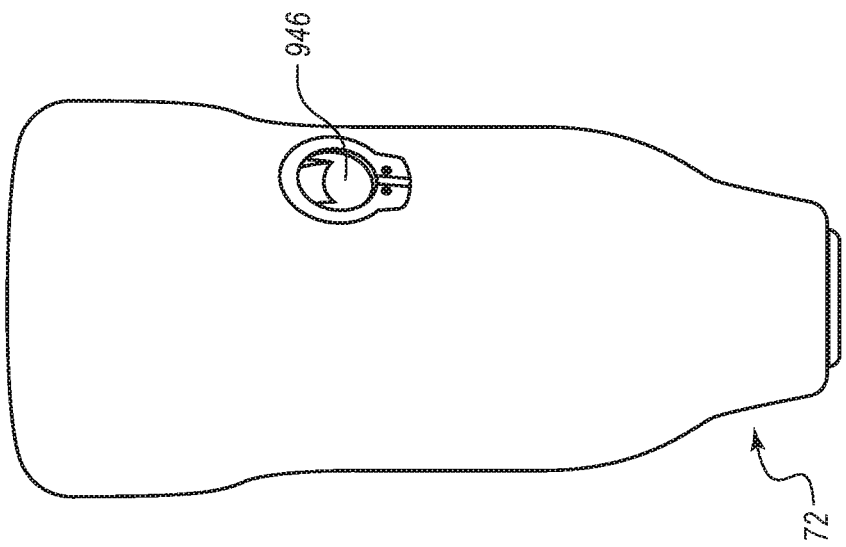
FIG. 29P is a perspective view of a socket that includes the base mounting plate coupled therewith.
Figure 29O:
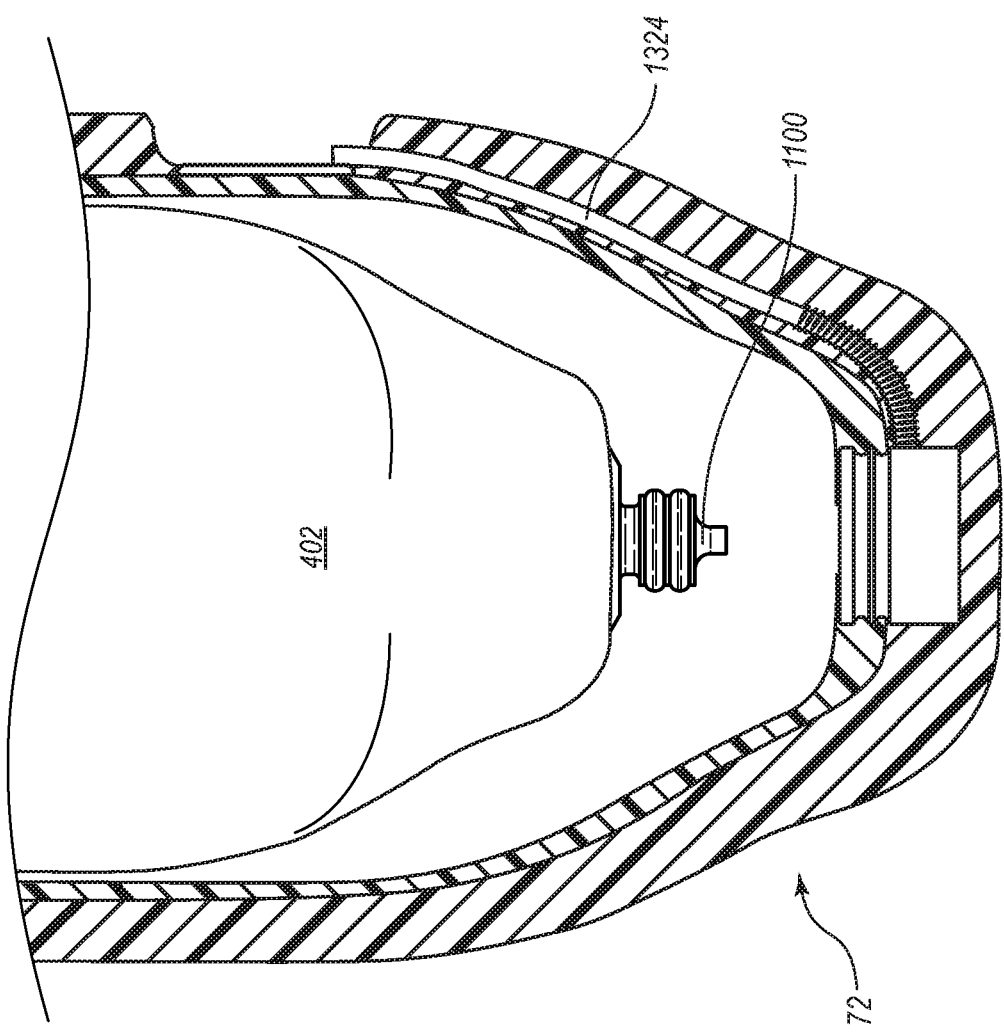
FIG. 29O is an elevation view similar to that of FIG. 29C, with portions thereof not shown or treated as transparent to show features that would otherwise be hidden, that depicts removal of the model and the post from the socket.
Figure 29Q:
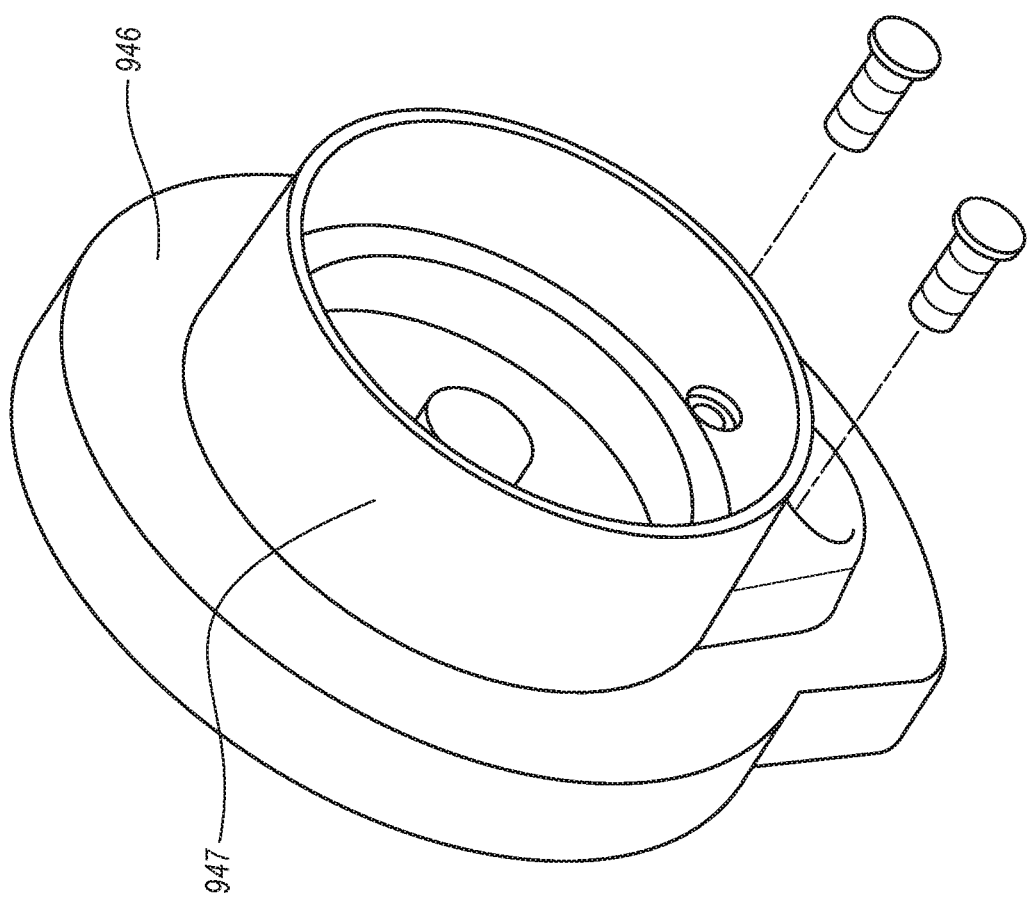
FIG. 29Q is a detailed perspective view that omits certain features depicted in FIG. 29P and shows the coupling of the reel housing to the base mounting plate.
Figure 29R:
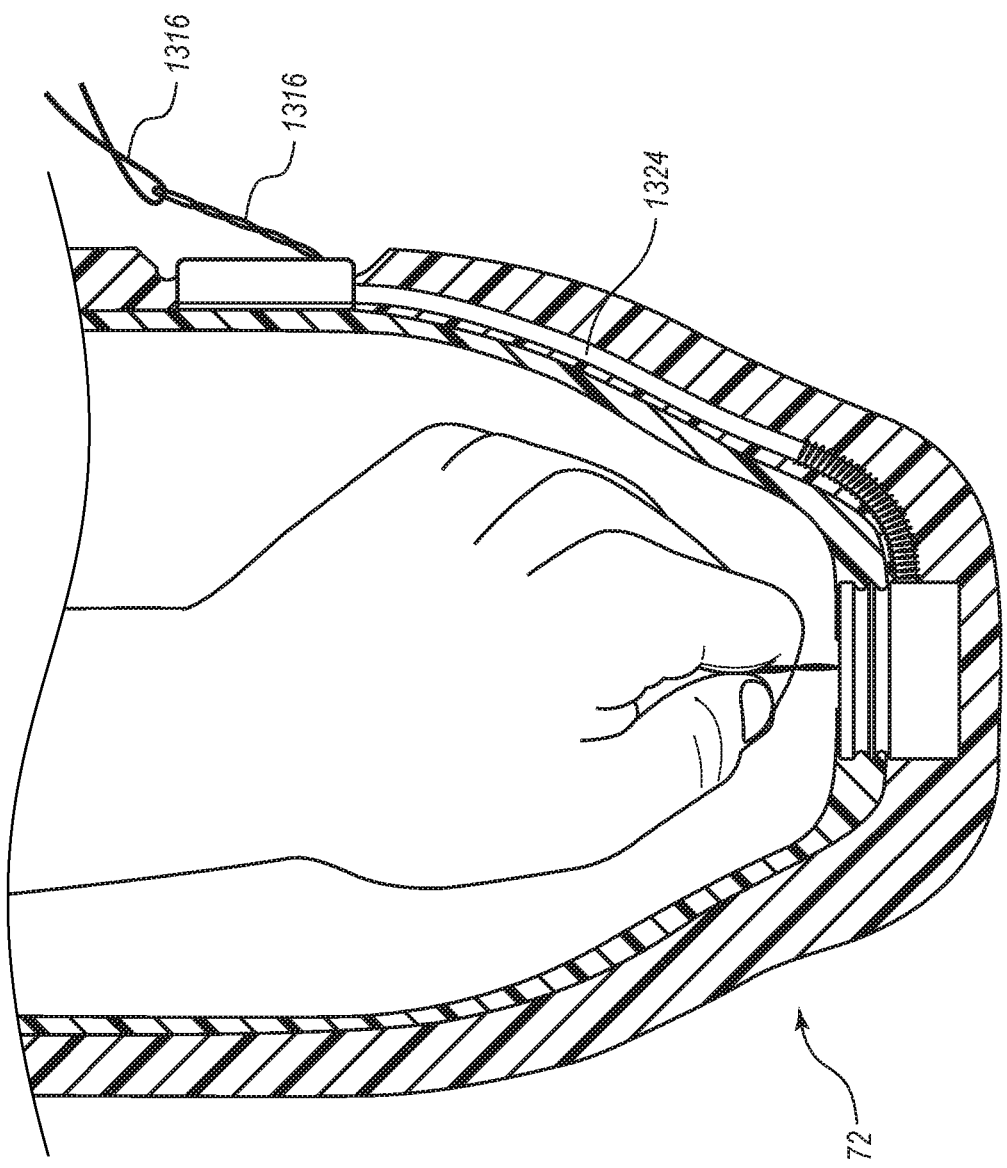
FIG. 29R is an elevation view similar to that of FIG. 29C, with portions thereof not shown or treated as transparent to show features that would otherwise be hidden, that depicts the use of a lace feeder to introduce a tensioning line into the conduit.
Figure 29S:
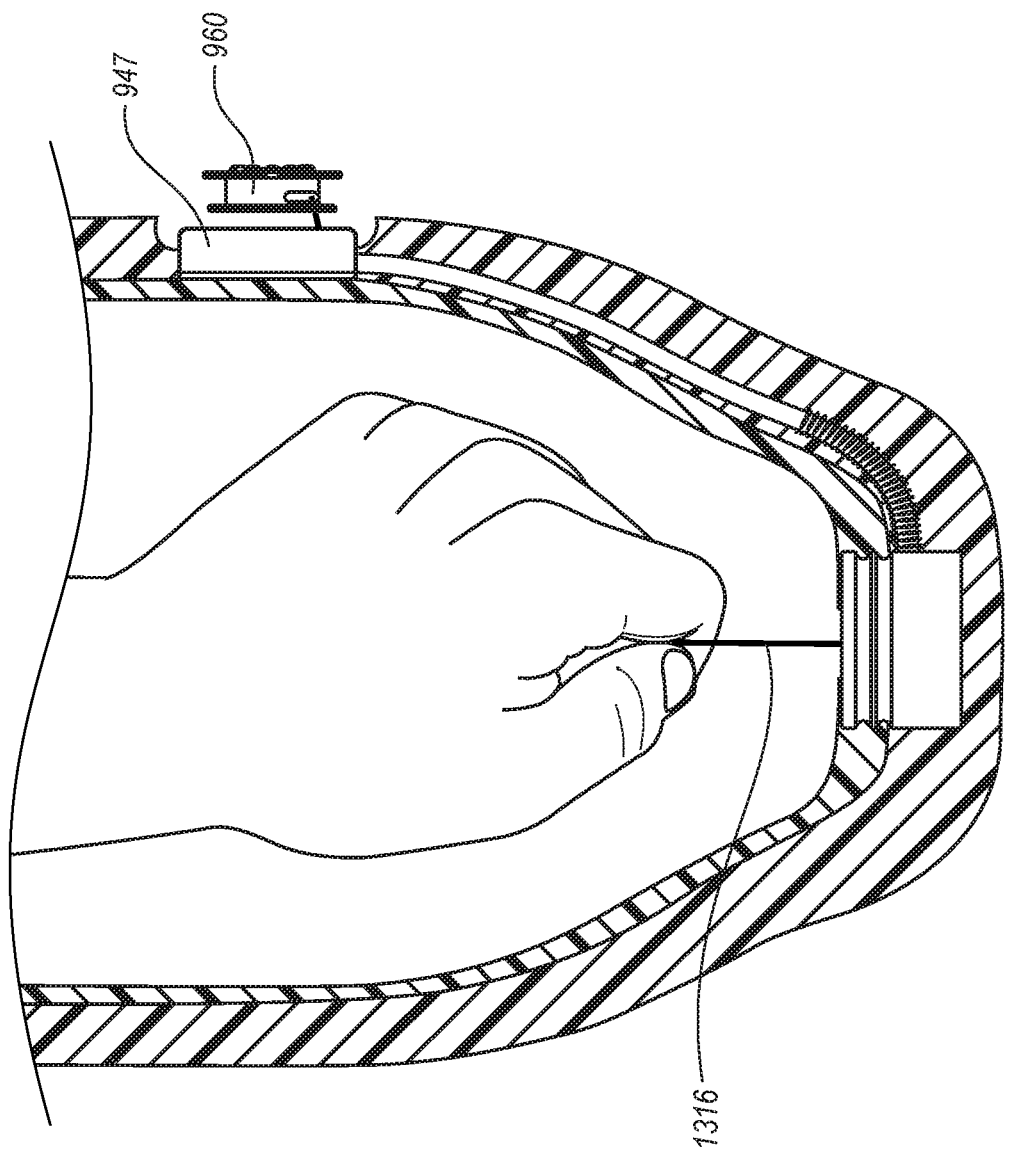
FIG. 29S is an elevation view similar to that of FIG. 29C, with portions thereof not shown or treated as transparent to show features that would otherwise be hidden, that depicts a user pulling one end of the tensioning line into an interior of the socket to draw a reel that is coupled to the other end of the tensioning line into the reel housing.
Figure 29V:
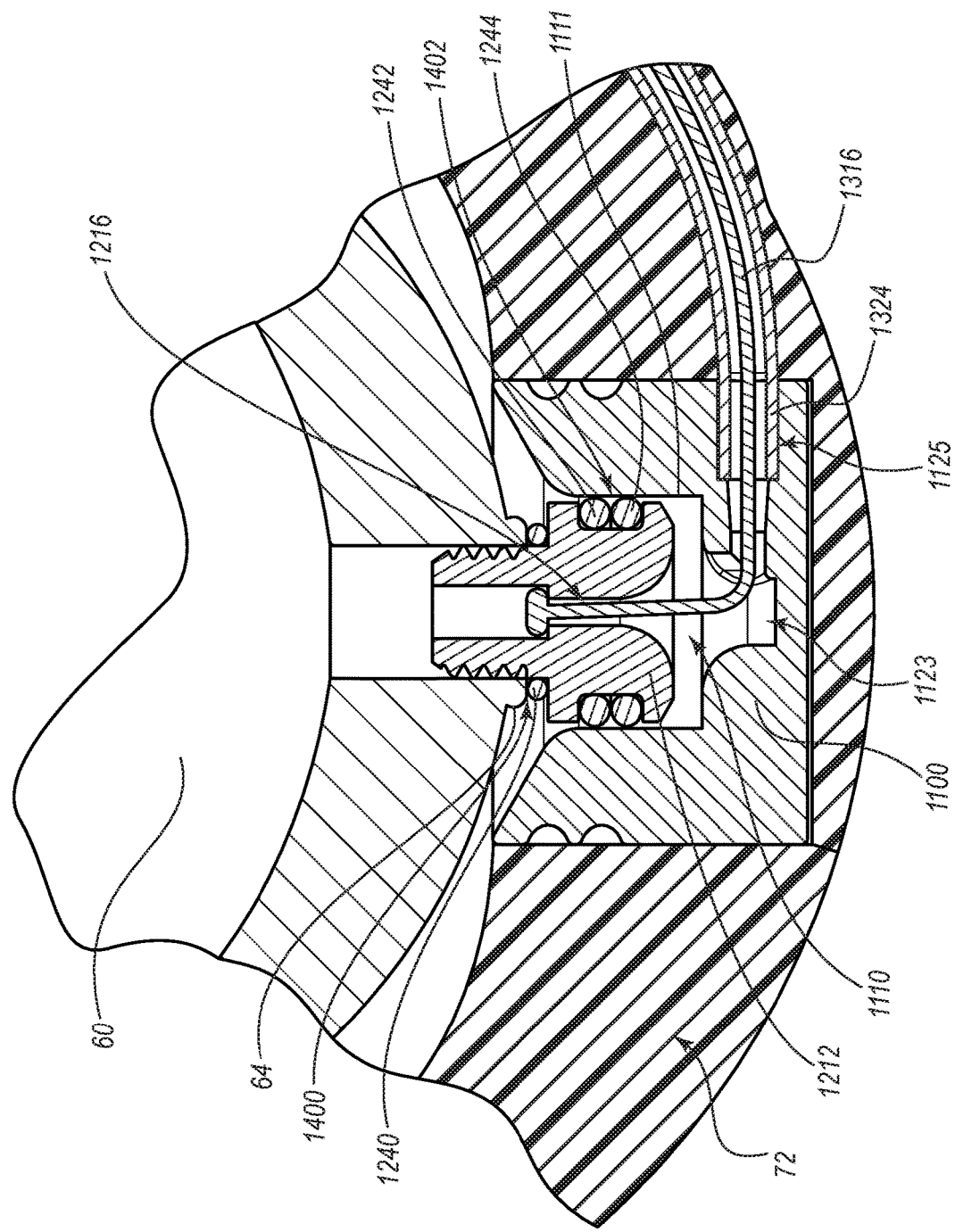

FIGS. 29A-29V depict various stages of illustrative methods for manufacturing a socket using components of the kit 1300. Other procedures may include more, fewer, and/or different stages. Moreover, any combination of sub-processes disclosed herein can form a standalone process having patentable features. Any of the illustrative methods or sub-methods may be included in various embodiments of the instructions 1303.

FIG. 29A is an elevation view of the post 1000 mounted to a distal end of a plaster model 402 of a residuum. In some embodiments, it can be desirable to seal the plaster mold 402 or prepare a flexible liner with a tapered distal hole to accept the lamination post 1000. In some implementations, the distal end of the plaster mold 402 may be flattened, such as with Sureform® tools available from Stanley Tools. In some implementations, a ½ inch hole can be drilled in a center of the distal end of the plaster mold 402 and filled with any suitable adhesive. The fastener 1042 of the post 1000 can then be inserted into the adhesive-filled hole and the resultant assembly held until the adhesive is set.

FIG. 29B is an elevation view of the plaster model 402 and the post 1000 with a barrier layer 404, such as a PVA bag, mounted to the post 1000. In particular, the PVA bag is tied off around the groove 1020 of the post 1000 via a string 405. The lamination housing 1100 is then coupled to the post 1000, with the conduit port 1139 oriented in the direction of the eventual placement of the tightening mechanism 906. Once the coupling is complete, a bead of silicone or the like can be applied about the connection to form a seal to prevent epoxy from leading into the lamination housing 1100.

FIG. 29C is an elevation view of the plaster model 402 with the lanyard housing 1100 mounted thereon via the post 1000. In this stage, multiple layers of material 406, 408 are positioned over the barrier layer 404 and the plaster model 402 and are coupled to the grooves 1130, 1132 of the lanyard housing 1100. Any suitable material is contemplated. In the illustrated embodiment, the layer 406 includes Nyglass, and the layer 408 includes carbon.

FIG. 29D is an elevation view such as that of FIG. 29C that depicts the conduit 1324 and the kink-resistant member 1324 in close proximity to the lanyard housing 1100 prior to coupling therewith. As previously discussed, the conduit 1324 can comprise any suitable configuration. In the illustrated embodiment, the conduit 1324 includes tubing 1325 (e.g., Teflon tubing) and an kink-resistant sheath 1327. In the illustrated embodiment, a distal end of the tubing 1325 extends distally beyond a distal end of the sheath 1327, which may facilitate coupling of the conduit 1324 and the kink-resistant member 1330 with the lanyard housing 1100. As used herein, the terms "proximal" and "distal" are used in an anatomical sense. Accordingly, the distal end of the residuum, as well as the plaster representation thereof 402, is the end of that is furthest from the core of the prosthetic user.

In some embodiments, the plug 1140 is coupled with the port 1139 (FIG. 26B) prior to coupling the lanyard housing 1100 with the post 1000 (FIG. 29B) or before or after laying up material, as depicted in FIG. 29C. For a two-stage lamination procedure, the a connection interface of the plug 1140 may be filled with clay to preserve its accessibility. The assembly can then be laminated with any suitable resin. Thereafter, the plug 1140 may be accessed by grinding down to expose the head of the bolt. The clay can be removed, and the bolt can then be extracted, thus providing access to the port 1139.

In a single-stage lamination procedure, the plug 1140 may be omitted. If used, however, the plug 1140 can be removed at any of the stages depicted in FIGS. 29B-29E to provide access to the port 1139.

FIG. 29E is a detailed elevation view that omits certain features depicted in FIG. 29D. In the illustrated stage, the kink-resistant member 1130 is positioned over a distal end of the conduit 1324. In particular, the kink-resistant member 1130 is positioned over the distal, unsheathed end of the tubing 1325.

FIG. 29F is another detailed elevation view that omits certain features depicted in FIG. 29D. In the illustrated stage, the distal end of the tubing 1325 is inserted into the port 1139 of the lanyard housing 1100. In some instances, it may be desirable to fill the distal end of the tubing 1325 with clay as a precaution against lamination material entering therein.

FIG. 29G is another detailed elevation view that omits certain features depicted in FIG. 29D. In the illustrated stage, the distal end of the kink-resistant member 1130 is inserted into the port 1139 of the lanyard housing 1100 over the distal end of the tubing 1325.

FIG. 29H depicts another stage at which a proximal end of the conduit 1324 is cut to a desired length. The conduit 1324 ends at the position where the tightening mechanism will be installed. At this stage, in some implementations, one can ensure that the kink-resistant member 1130 has a rounded bend and is not kinked.

FIG. 29I depicts a stage at which the proximal end of the conduit 1324 is coupled with the dummy 990. The dummy 990 is coupled with the base mounting plate 946, which coupling may occur before or after attachment of the base mounting plate 946 to the layer 408. In some instances, it may be desirable to fill the proximal end of the tubing 1325 with clay as a precaution against lamination material entering therein. The proximal end of the tubing 1325 can be inserted into the port or recess 997 of the dummy 990.

FIG. 29J depicts a stage at which the mounting-plate-and-dummy assembly is coupled to the outer layer 408 of material that has been laid up on the plaster model 402. The proximal end of the conduit 1324 is shown as having been coupled with the dummy 990.

FIG. 29K depicts lamination of one or more further layers of material 424 over the lanyard housing 1100, the conduit 1324, the base mounting plate 946, and the dummy 990.

FIG. 29L shows removal of a portion of the lamination material 424 to expose the base mounting plate 946 and the dummy 990, such as via any suitable grinding tool.

FIG. 29M depicts removal of fasteners from the mounting plate 946 and the dummy 990, in a manner such as previously described.

FIG. 29N depicts insertion of the extraction device 994 through the dummy 990 to assist in removal of the dummy 990 from the base mounting plate 946, in a manner such as previously described.

FIG. 29O depicts removal of the plaster model 402 and the post 1000 from the formed socket 72.

FIG. 29P is a perspective view of the socket 72 with the base mounting plate 946 coupled therewith.

FIG. 29Q shows the coupling of the reel housing 947 to the base mounting plate 946 in manners such as previously discussed.

FIG. 29R depicts the use of the lace feeder 1310 to introduce the tensioning line 1316 into the conduit 1324.

FIG. 29S depicts a user pulling one end of the tensioning line 1316 into an interior of the socket 72 to draw the reel 960 that is coupled to the other end of the tensioning line into the reel housing 947.

FIG. 29T depicts the coupling of the actuator 930 to the reel housing 947 using the tool 1306.

FIG. 29U depicts the coupling of the connector 1212 to the tensioning line 1316 in a manner such as previously disclosed.

FIG. 29V is a cross-sectional view of a distal end of the socket 72 that depicts the lanyard connector 1212 having been drawn into the receptacle 1110 of the lanyard housing 1100 via the tensioning device 906 (FIG. 29T). The lanyard connector 1212 is attached to the connector 64 of the liner 60, and thus the liner 60 has been drawn to the distal end of the socket 72.

As previously discussed, the sealing member 1240 can form a fluid-tight seal 1400 with the liner connector 64. This seal 1400 can prevent air from flowing from an environment in the vicinity of the external surfaces of the connectors 64, 1212 to the channel 1216 of the connector 1212. Likewise, the seal 1400 can prevent air from flowing from the channel 1216 outwardly to the environment in the vicinity of the external surfaces of the connectors 64, 1212.

Further, as previously discussed, the sealing members 1242, 1244 can form a seal 1402 with the sidewall 1111 of the lanyard housing 1100. This seal 1402 can prevent air from flowing from an environment in the vicinity of the external surfaces of the connector 1212 and the lanyard housing 1100 to receptacle 1110 of the lanyard housing 1100. Likewise, the seal 1402 can prevent air from flowing from the receptacle 1110 outwardly to the environment in the vicinity of the external surfaces of the connector 1212 and the lanyard housing 1100.

In many instances, the arrangement just discussed and depicted in FIG. 29V is the configuration in which the wearer of the liner 60 and socket 72 will use the prosthetic device of which these form a part. For example, if the socket 72 is coupled with a prosthetic foot/ankle attachment, the user may walk, run, or otherwise move about with the assembly in the configuration illustrated here. In the absence of the fluid-tight seals 1400, 1402, such movement could force air through one or more of the channel 1216 of the lanyard connector 1216; the receptacle 1110, the recess 1123, or the passageway 1125 of the lanyard housing 1100; or through a lumen defined by the conduit 1324. Air movement through such regions could potentially make noises, such as hissing, whistling, whooshing, etc. The fluid-tight seals 1400, 1402 can inhibit or prevent such air movement and reduce or eliminate undesired sounds.

Other embodiments of kits and methods may differ somewhat from those just discussed. For example, in some embodiments, the kit does not include a base mounting plate 946. In certain of such embodiments, the instructions 1303 include directions to couple the reel housing 947 with a base mounting portion that is formed directly in the socket 72. For example, in some embodiments, the socket 72 may be formed by additive manufacturing (e.g., 3D printing), and may include a base mounting portion that is configured to couple with the housing 947.

Figure 30:
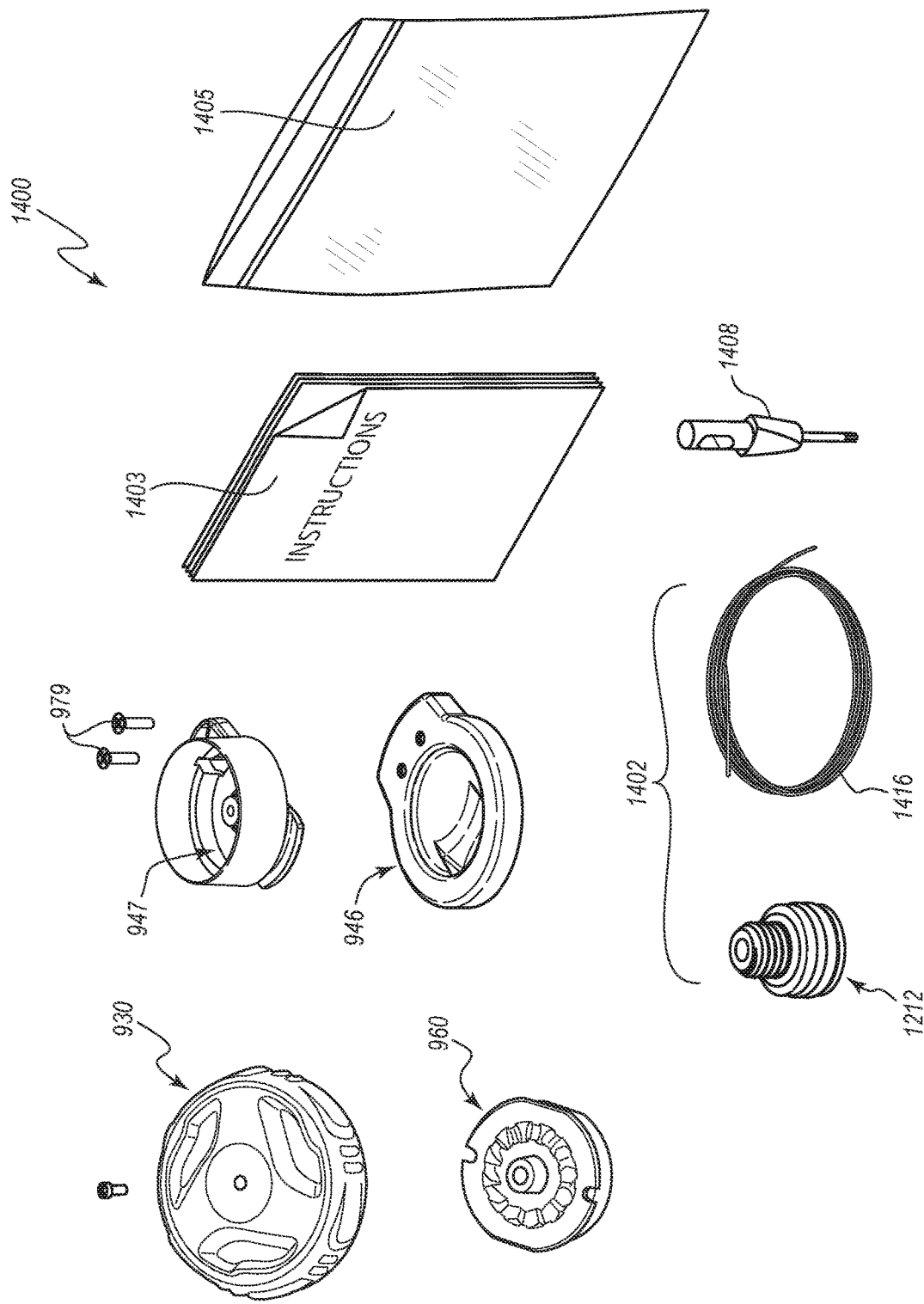
FIG. 30 is a perspective view of another embodiment of a kit that is configured to be used in the manufacture of a socket.

FIG. 30 illustrates an embodiment of a kit 1400 that includes materials for use in a socket-formation procedure. For example, in some embodiments, the kit 1400 may be particularly well-suited for use with thermoformed/vacuum formed sockets (see, e.g., FIG. 22). In some instances, the kit 1400 may be used for retrofitting a socket that has already been formed.

In some instances, rather than laminating the base mounting plate 946 within the wall of the socket, the base mounting plate 946 is instead attached to an external surface of the socket. Any suitable fasteners for such attachment are contemplated, including, for example, screws, rivets, etc. The kit 1400 may include fewer components than the kit 1300. For example, the kit 1400 can include any suitable combination of the following components: the various elements of the tightening device 906, including the base mounting plate 946, the reel housing 947, the fasteners 979, the reel 960, and the actuator 930; a lanyard 1302, which can include the connector 1212 and a tensioning line 1416; and instructions 1403. Further, in the illustrated embodiment, the kit 1400 includes a tool 1408 for use in assembling or disassembling the tightening device 906, such as for mounting or removing the actuator 930.

The instructions 1303 can include directions for performing any and/or all of the steps of a method for creating a socket that includes a lanyard suspension system, such as any of the procedures or sub-processes thereof discussed above and/or below. In other or further embodiments, the instructions 1303 may provide directions for accessing such directions. For example, the instructions may list a web address, a mailing address, and/or a telephone number that can be used to locate instructions for preparing a socket. One or more of the foregoing items can be included in and/or on (e.g., in the case of the instructions) packaging 1305 for the kit. Any suitable form of packaging 1305 is contemplated.

Figure 31:
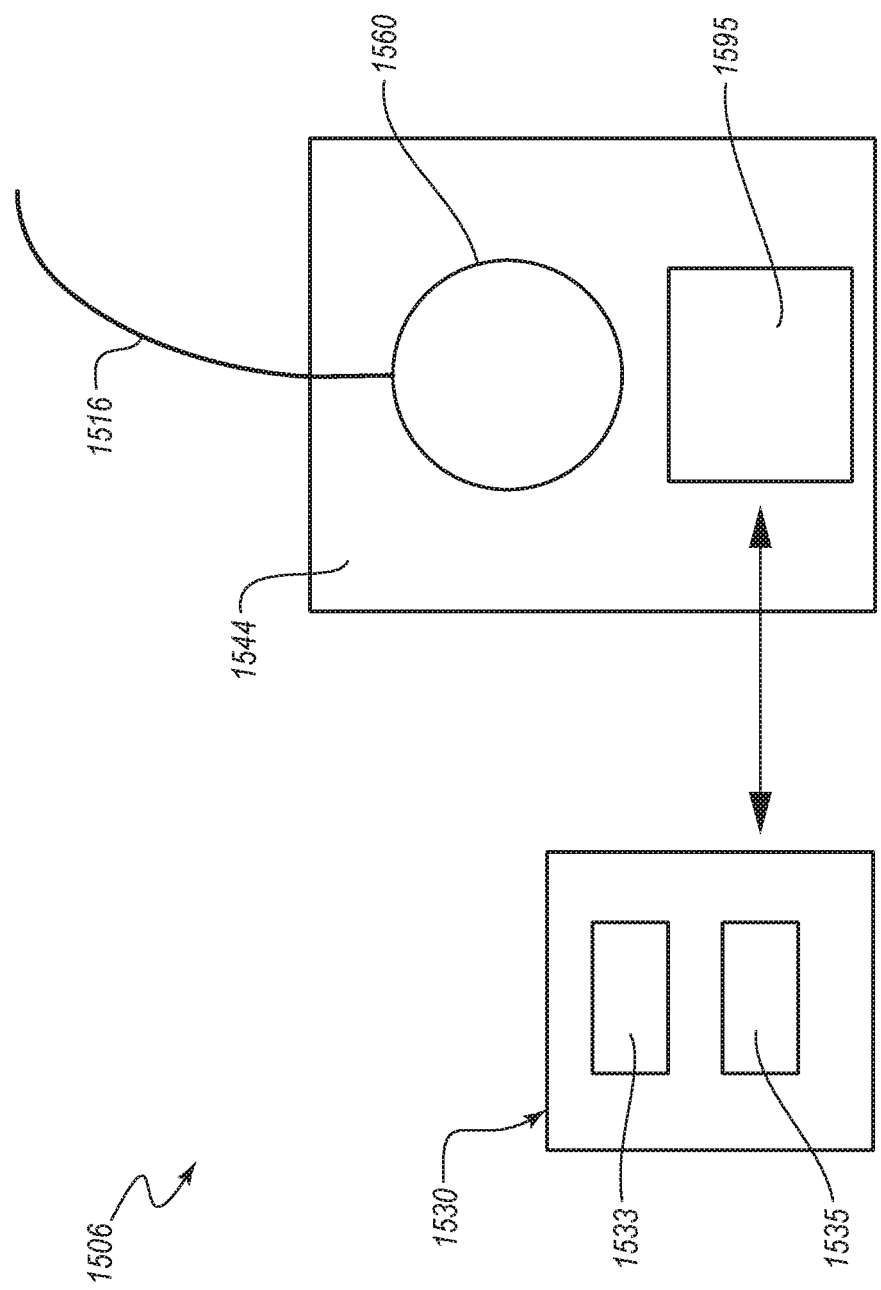
FIG. 31 is a schematic view of another embodiment of a tightening mechanism that is compatible with embodiments disclosed herein.

FIG. 31 schematically depicts another embodiment of a tightening mechanism 1506 that may be used with embodiments disclosed herein. The tightening mechanism is configured for automated and/or motorized tightening and/or loosening of a tensioning line 1516. As with other embodiments discussed herein, the tightening mechanism 1506 may, in some embodiments, include a housing or base 1544, whether of integral or multi-part construction. The tightening mechanism 1506 can include a spool or reel 1560 about which the tensioning line 1516 may be wound or unwound. The reel 1560 can be controlled by a motor 1595. For example, the motor 1595 may be coupled with the reel 1560 so as to wind or unwind with the reel without the user mechanically interacting with the reel 1560. Such winding or unwinding may be referred to as automated tensioning or motorized tensioning.

In the illustrated embodiment, the tightening mechanism 1506 includes an actuator 1530 via which the motor 1595 can be controlled. In the illustrated embodiment, the actuator 1530 includes input interfaces 1533, 1535 via which controls are provided to the motor 1595. For example, in some embodiments, the interface 1533, 1535 may be buttons, whether dedicated mechanical buttons or buttons that appear on a touch screen of an electronic device, such as a smart phone. Use of either input interface 1533, 1535 may be termed actuation of the actuator 1530. Moreover, for sake of illustration, the input interfaces 1533, 1535 may be referred to as buttons.

The buttons 1533, 1535 may be pressed to effect tightening or loosening of the tensioning line 1516, respectively. For example, in some instances, the button 1533 may be pressed or actuated to effect gathering of at least a portion of the tensioning line 1516 into the housing or base 1544 and/or tightening of the tensioning line 1516. In other or further instances, the button 1535 may be pressed or actuated to effect release of at least a portion of the tensioning line 1516 from the housing or base 1544 and/or loosening of the tensioning line 1516. Actuation of the button 1536 may also be considered movement of the actuator 1530 to a tension-release state.

The motor 1595 and/or any local electronics that control the motor (e.g., controllers or other electronics that reside within the housing or base 1544) may also be referred to as an actuator. In certain embodiments, such a localized actuator positioned on or within the housing or base 1544 can communicate with the actuator 1530.

Any suitable arrangement of an automated and/or motorized tightening mechanism 1506 and actuator 1530 is contemplated. For example, illustrative embodiments of suitable tightening mechanisms and/or actuators are disclosed in U.S. Pat. No. 9,248,040 B2, titled MOTORIZED TENSIONING SYSTEM FOR MEDICAL BRACES AND DEVICES, which issued on Feb. 2, 2016, the entire contents of which are hereby incorporated by reference herein.

Figure 32B:
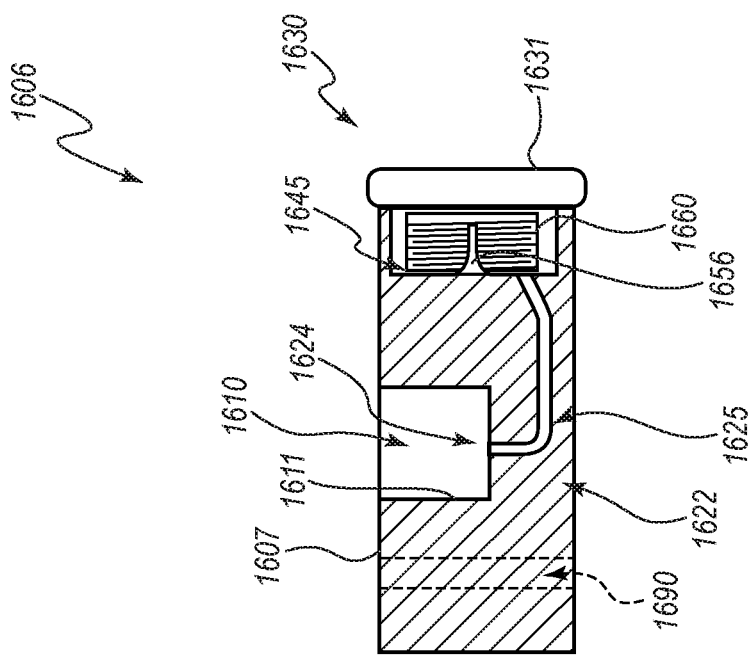
FIG. 32B is cross-sectional view of the housing element with the integrated tightening mechanism of FIG. 32A.
Figure 32A:
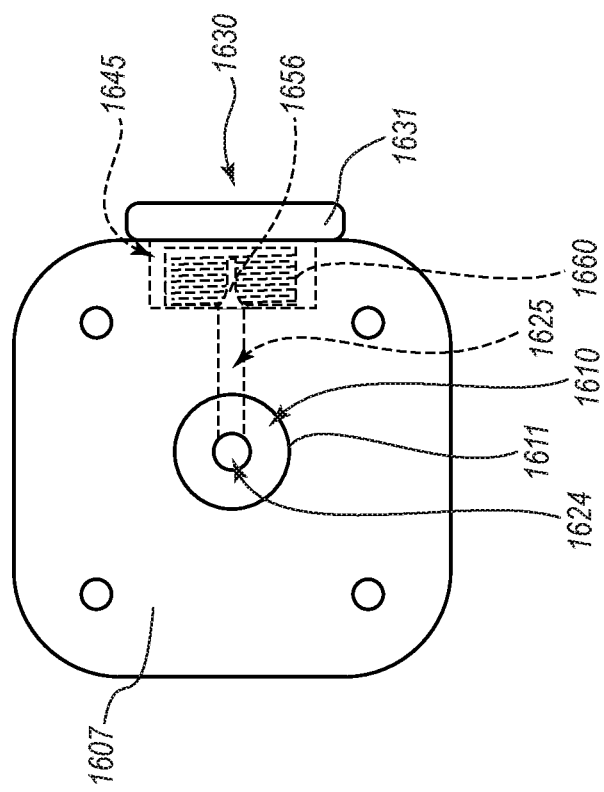
FIG. 32A is a top plan view of another embodiment of a lanyard housing that includes an integrated tightening mechanism.

FIGS. 32A and 32B depict another embodiment of a tightening mechanism 1606 for a lanyard. The tightening mechanism 1606 resembles the tightening mechanisms discussed above in many respects, and thus includes similarly numbered features. For example, the tightening mechanism 1606 can include an actuator 1630 that is configured to wind and/or unwind (or tighten and/or untighten) a tensioning line about a spool 1660 that is rotationally mounted on a post 1656 in manners such as previously discussed. The actuator 1630 comprises a dial or cover 1631 in the illustrated embodiment.

As with other tightening mechanisms, the tightening mechanism 1606 comprises a housing 1607 into which the tensioning line is gathered. In the illustrated embodiment, the housing 1607 includes many features that are the same as or similar to those of housings described above, and in particular, the lanyard housing 1100 discussed above. Accordingly, the base or housing 1607 may also be referred to as a lanyard housing 1607. Stated otherwise, a housing portion of the tightening mechanism 1606 and a lanyard housing region of the housing 1607 that may function in manners such as described above with respect to similarly identified features may be integrated into a single component. For example, both housing elements may be defined by a unitary piece of material, such as shown in FIGS. 32A and 32B. It may also be stated that the housing of the tightening mechanism 1606 defines the lanyard housing, or that the lanyard housing defines the housing portion of the tightening mechanism 1606.

The lanyard housing 1607 includes a receptacle 1610 at least partially defined by a sidewall 1611. The lanyard housing 1607 includes a diverter portion 1622 at a base thereof that can redirect the tensioning line toward the spool 1660. The lanyard housing 1607 defines a passageway 1625 through which the tensioning line is conducted. An opening 1624 at an end of the passageway 1625 is positioned at a bottom of the receptacle 1624. The foregoing features can be the same as or closely resemble those of similarly numbered features of the lanyard housing 1100.

In the illustrated embodiment, the opening 1624 is positioned along a central longitudinal axis of the receptacle 1610. In other embodiments, the opening 1624 may be offset from the central longitudinal axis, such as in manners discussed above with respect to the lanyard housing 1100.

The lanyard housing 1607 can have a profile that is substantially square with rounded corners. The housing 1607 may be substantially disk-shaped, with upper and lower faces that may be substantially planar and/or substantially parallel to each other. The housing 1607 may also be said to be substantially puck-shaped, with four flattened sides. The illustrated housing 1607 may be particularly well-suited for coupling with standard mounting hardware for prosthetic limbs. For example, the illustrated lanyard housing 1607 defines a plurality of attachment channels 1690 for coupling with fasteners, such as bolts. The illustrated lanyard housing 1607 defines four such attachment channels 1690 that can be arranged for ready attachment to standard four-hole mounting hardware for prosthetic limbs. In some embodiments, the channels 1690 include any suitable attachment interface. For example, in the illustrated embodiment, the channels 1690 are internally threaded. Any other suitable shape or configuration of the lanyard housing 1607 is contemplated. The portion of the lanyard housing 1607 that defines the channels 1690 is the portion by which the lanyard housing 1607 is secured to a socket. This portion may also be referred to herein as a base or as base portion 1692. In the illustrated embodiment, the base portion 1692 is encompasses a portion of the receptacle 1610 and includes the corners of the lanyard housing 1607.

Figure 33:
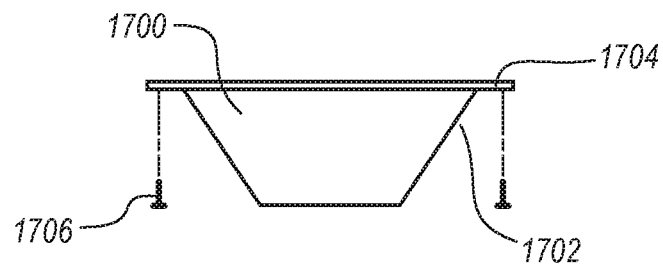
FIG. 33 is a side elevation view of an embodiment of a mounting element.

FIG. 33 depicts an attachment key 1700 that can be used in preparing a socket for eventual coupling with the tightening mechanism 1607. The attachment key 1700 may be substantially rigid and may be formed of any suitable material. In some embodiments, the attachment key 1700 is formed of Delrin®. The attachment key 1700 can include an alignment surface 1702 that can be complementary to a surface of a mounting plate 1710 (FIGS. 34A and 34B), which is described further below. In the illustrated embodiment, the alignment surface 1702 is substantially frustoconical in shape.

The attachment key 1700 can be configured to be attached to a model of a residuum in any suitable manner. In the illustrated embodiment, the attachment key 1700 comprises a flange 1704 that may include a plurality of openings (not shown) through which a plurality of fasteners 1706 (e.g., nails) may be advanced into coupled arrangement with the mold. For example, in some instances, a plaster mold may be flattened at a distal end thereof, and the attachment key 1700 may be secured to the flattened region of the mold via the fasteners 1706.

Figure 34A:
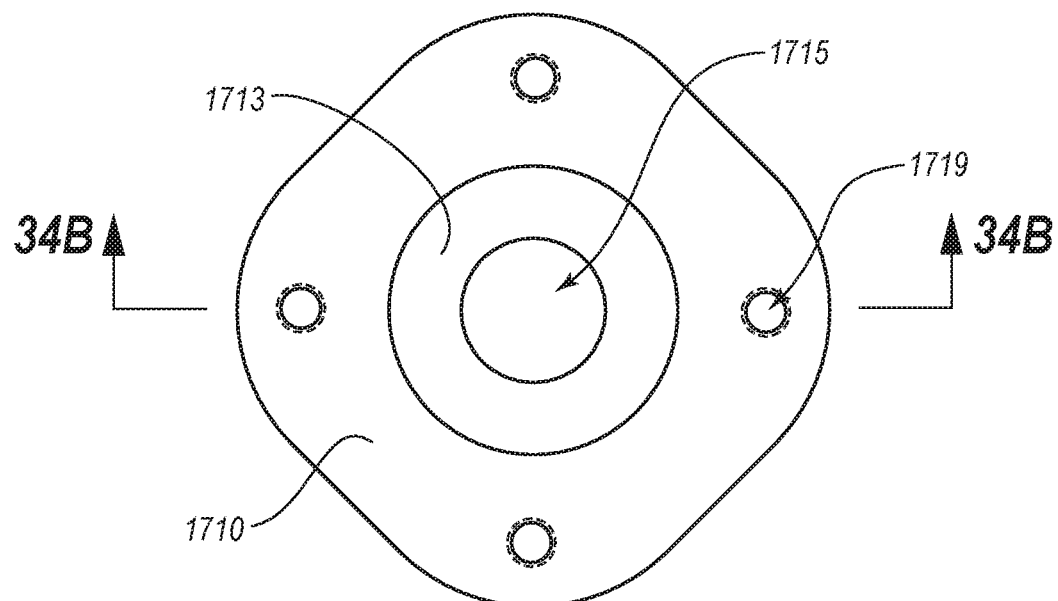
FIG. 34A is a top plan view of an embodiment of an anchor configured for use with the mounting element of FIG. 33.
Figure 34B:
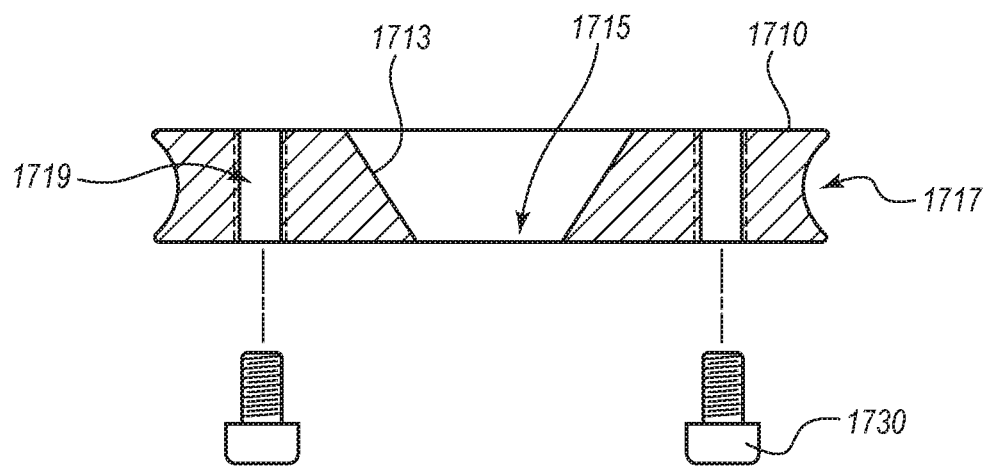
FIG. 34B is a cross-sectional view of the anchor of FIG. 34A taken along the view line 34B-34B in FIG. 34A that also depicts a side elevation view of mounting hardware.

FIGS. 34A and 34B depict an embodiment of a mounting plate 1710 that can be used to secure the tightening mechanism 1606 to a socket. In various embodiments, the mounting plate 1710 may be suitable for use with laminated or thermoformed sockets. The mounting plate 1710 may be substantially rigid and may be formed of any suitable material. In some embodiments, the mounting plate 1710 is formed of aluminum.

In the illustrated embodiment, the mounting plate 1710 includes a funnel region 1713 that is shaped substantially as a frustocone. The funnel region 1713 may be shaped and may function substantially the same as the funnel region 1113 described above when used with a lanyard. Moreover, in the illustrated embodiment, the funnel region 1713 may be shaped complementarily to the alignment surface 1702 of the attachment key 1700. Mating the funnel region 1713 and the attachment key 1700 can help achieve a desired orientation of the mounting plate 1710 during formation of the socket.

The mounting plate 1710 can define any suitable shape. In the illustrated embodiment, the mounting plate 1710 defines an outmost perimeter that is identical to that of the lanyard housing 1607. In particular, the mounting plate 1710 has a perimeter that is substantially square with rounded corners. The mounting plate 1710 may be substantially disk-shaped, with upper and lower faces that may be substantially planar and/or substantially parallel to each other. The illustrated mounting plate 1710 may be particularly well-suited for coupling with standard mounting hardware for prosthetic limbs. For example, the illustrated mounting plate 1710 defines a plurality of attachment channels 1719 for coupling with fasteners, such as bolts. The illustrated mounting plate 1710 defines four such attachment channels 1719 that can be arranged for ready attachment to standard four-hole mounting hardware for prosthetic limbs. In some embodiments, the channels 1719 include any suitable attachment interface. For example, in the illustrated embodiment, the channels 1719 are internally threaded. Any other suitable shape or configuration of the mounting plate 1710 is contemplated.

In the illustrated embodiment, the mounting plate 1710 includes a tie-off channel or groove 1717 that may be useful in certain socket formation procedures. For example, in some embodiments, the groove 1717 may be used for securely tying one or more layers of material to the mounting plate 1710 during layup of the material for a lamination procedure. The groove 1717 may extend about a full perimeter of the mounting plate 1710, or in other embodiments, along only a portion thereof.

In some embodiments, plugs 1730 may be coupled with the channels 1719 during formation of the socket to prevent material (e.g., resin) from entering into the channels 1719. In the illustrated embodiment, the plugs 1730 are bolts.

The mounting plate 1710 can define an opening 1715 at a distal end of the funnel region 1713. This opening 1713 can be aligned with an opening at the proximal end of the receptacle 1610 of the lanyard housing 1607. In some embodiments, these openings are substantially the same size and shape as each other. When the lanyard housing 1607 is coupled to the mounting plate 1710, the funnel region 1713 and the receptacle 1610 can closely resemble, both in form and function, the receptacle 1110 of the lanyard housing 1100 discussed above.

Figure 35:
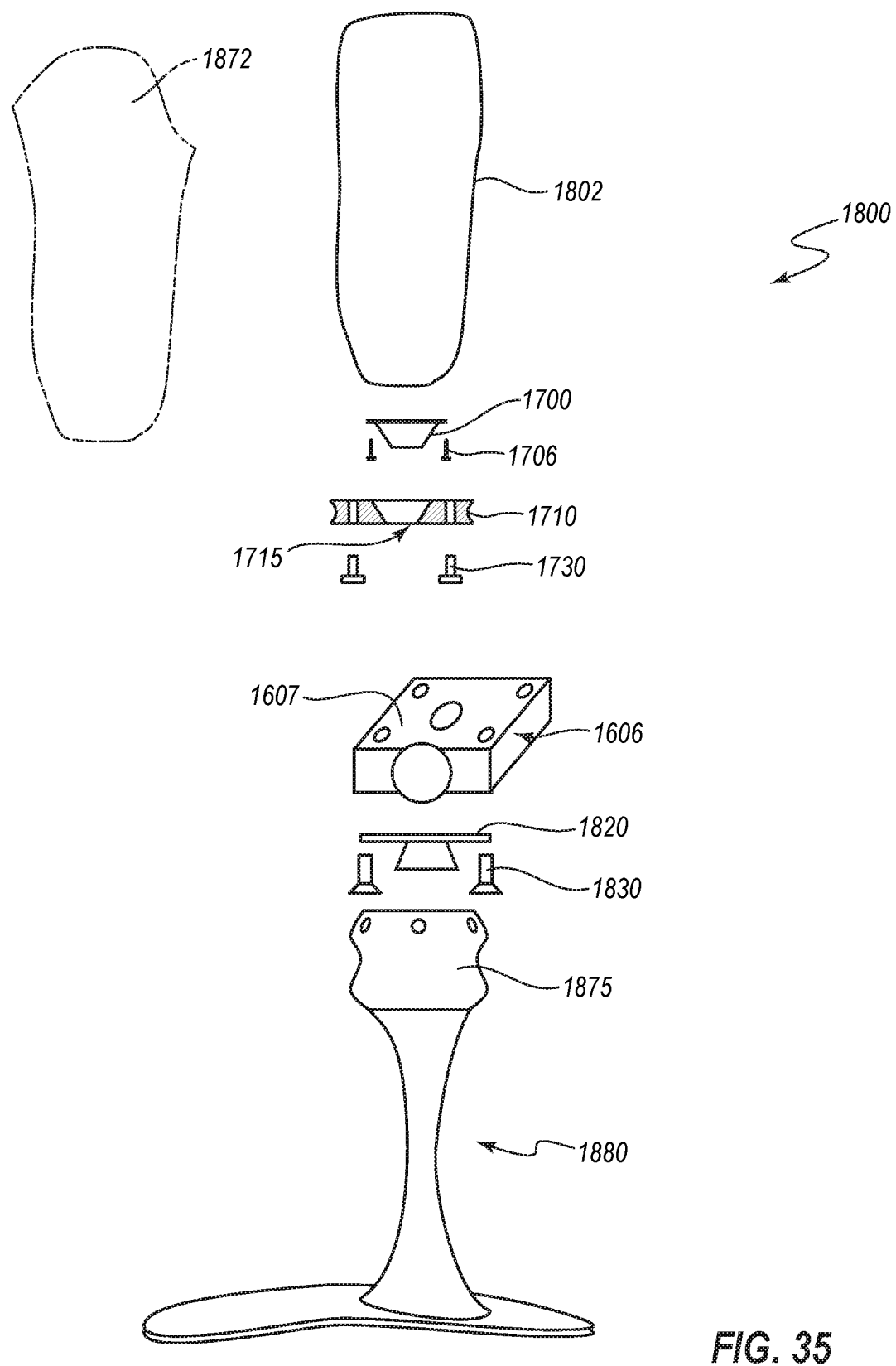
FIG. 35 is an exploded perspective view of an embodiment of a prosthetic assembly that includes the housing and the tightening mechanism of FIG. 32A, the mounting element of FIG. 33 (shown in cross-section, and rotated approximately 45 degrees), and the anchor of FIG. 34A.

FIG. 35 depicts a prosthetic system 1800 that can include the mounting plate 1710 and the tightening mechanism 1606. As further discussed hereafter, in some embodiments, the mounting plate 1710 is incorporated into a thermoplastic socket 1872 during a thermoforming or vacuum-forming procedure. In other embodiments, the mounting plate 1710 is incorporated into a laminated socket 1872. For either types of procedure, the socket 1872 that may be formed during the procedure is depicted in broken lines 1872. In still other instances, one or more of the mounting plate 1710 or the tightening mechanism 1606 may be secured to a preformed socket 1872, such as, for example, in a retrofitting operation. The mounting plate 1710 is shown in cross-section in FIG. 35, rather than in perspective like other components, and is rotated approximately 45 degrees relative to an orientation in which it would couple with the tightening mechanism 1606.

Various illustrative methods for securing the tightening mechanism 1606 to the socket 1872 will now be described. In some methods, a distal end of a mold 1802 is flattened to provide a base for the attachment key 1700. The attachment key 1700 is then secured to the base of the mold 1802 via the fasteners 1706. The stages of socket formation that follow can vary, depending on the type of procedure used.

In certain thermoforming procedures, the mounting plate 1710 is then positioned over the attachment key 1700 with the plugs 1730 in place. A heated layer of thermoplastic material may then be positioned over the assembly and vacuum formed thereto in manners known in the art to form the socket 1872. The mold 1802 and the attachment key 1700 may then be removed from the socket 1872. The plugs 1730 may also be exposed (e.g., via grinding) and removed.

In certain lamination procedures, a barrier layer, such as a PVA bag, is positioned over the mold 1802 and the attachment key 1700. The end of the bag is inserted through the opening 1715 of the mounting plate 1710, and the mounting plate 1710 is then positioned over the attachment key 1700. In some instances, at least a portion of the bag that extends past the mounting plate 1710 can be removed. One of more layers of materials suitable for use in a laminated socket, such as any of the materials previously disclosed, can then be positioned over the assembly. One or more layers of material may extend over a distal face of the mounting plate 1710. Another barrier layer may be applied to the exterior of the layup, and then resin may be introduced between the two barrier layers and lamination may proceed in any suitable manner, such as those known in the art. After lamination is complete and the resin has hardened to form the socket 1872, the mold 1802 and the attachment key 1700 are removed from the socket 1872. The plugs 1730 may also be exposed (e.g., via grinding) and removed.

In either case, the tightening mechanism 1606 may then be secured to the mounting plate 1710. In many embodiments, the tightening mechanism 1606—in particular, the lanyard housing 1607 thereof—may be sandwiched between the mounting plate 1710 and interface hardware for a prosthetic extremity 1820, which is also referred to as interface 1820. Some of the socket material may be sandwiched between the mounting plate 1710 and the lanyard housing 1607, such as some of the thermoplastic material or some of the laminated material, in view of the procedures previously discussed. The interface 1820 can be coupled with the lanyard housing 1607 and/or the mounting plate 1710 in any suitable manner. In the illustrated embodiment, a plurality of (e.g., four) fasteners 1830 (e.g., bolts) are advanced through channels (not shown) in the interface 1820 that are aligned with the channels 1690 of the lanyard housing 1607 and the channels 1719 of the mounting plate 1710, which were previously described. In the illustrated embodiment, the interface 1820 is shown in elevation, rather than in perspective like other components).

The interface 1820 may be of any suitable variety. Many types of interfaces 1820 are known in the art. The illustrated interface 1820 is of the pyramid variety, but other varieties may be used. The interface 1820 can be configured for coupling with a support attachment or adapter 1875 for a prosthetic extremity 1880 in any suitable manner.

A lanyard may be attached to the system in manners such as described above. In particular, a tensioning line may be fed through the passageway 1625 of the lanyard housing 1607 (e.g., via a feeder) and coupled with the spool 1660. The cover 1631 may be removed and/or fastened to the housing 1607 in any suitable manner. At its other end, the tensioning line may be coupled with a connector, such as the connector 1212 discussed above.

Kits for manufacturing a socket may include any suitable combination of the components described above. For example, in some embodiments, a kit can include any suitable combination of the following components: the attachment key 1700; the fasteners 1706; the tightening mechanism 1606 and its constituent components; the plugs 1730; an interface 1820 of any suitable variety; fasteners 1830; and a lanyard, such as a lanyard that includes a connector (e.g., the connector 1212) and a tensioning line.

In certain embodiments, the kits can include directions for performing any and/or all of the steps of a method for creating a socket that includes a lanyard suspension system, such as any of the procedures or sub-processes thereof discussed above. In other or further embodiments, the instructions may provide directions for accessing such directions. For example, the instructions may list a web address, a mailing address, and/or a telephone number that can be used to locate instructions for preparing a socket. One or more of the foregoing items can be included in and/or on (e.g., in the case of the instructions) packaging for the kit. Any suitable form of packaging is contemplated.

With reference to FIGS. 32A, 32B, and 35, the tensioning member 1606 can increase tension in a tensioning line, such as the tensioning line 1316 (see FIGS. 28 and 29V), that is coupled to the spool 1660. Advantageously, due to the manner in which the tightening member 1606 operates (which can resemble that discussed above with respect to FIGS. 7-9), at least a portion of the forces that arise due to this increased tension are distributed within the lanyard housing 1607.

For example, in the illustrated embodiment, the tensioning line 1316 is wrapped about the spool 1660 that is pivotally mounted to the post 1656, which is coupled to (e.g., attached to or integrally formed with) the lanyard housing 1607. As tension in the tensioning line increases, forces are distributed from the post 1656, which assists in keeping one end of the tensioning line 1316 taut, to other portions of the lanyard housing 1607. In some instances, these forces may be further distributed to components coupled to the lanyard housing 1607, such as the mounting plate 1710, the socket 1872, the interface 1820, and/or the prosthetic extremity 1880. The lanyard housing 1607 and/or other components are able to counter these forces that are distributed to them in order to maintain the tensioning line 1316 in tension. Such an arrangement can facilitate tensioning of the tensioning line, as a user is not required to provide all of the force that might otherwise be necessary to snugly secure a liner 60 in the socket 1872. Further, in view of the discussion above regarding operation of the tightening member 106, which resembles the tightening member 1606 in many respects, the tightening member 1606 can distribute force, which is due to tension in the tensioning line, into the lanyard housing 1607 throughout an entirety of an actuation event by which actuation of the actuator 1630 increases tension in the tensioning line 1316. For example, the post 1656 can distribute forces from the reel 1660, which forces arise from the tensioning line, to the lanyard housing 1607 throughout an entirety of an actuation event in which the knob 1631 is rotated, or repeatedly rotated, to increase the tension on the tensioning line 1316.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Only those elements that are specifically recited in means-plus-function format by use of the term "means," to the extent any exist, are intended to be construed in accordance with 35 U.S.C. § 112(f). Embodiments of the invention in which an exclusive property or privilege is claimed are defined as follows.

The invention claimed is:

1. A method of fabricating a prosthetic socket, comprising:

forming a socket comprising a sidewall, a cavity configured to receive a liner, a distal end, and a guide path, wherein the guide path extends proximally from the distal end of the socket;

inserting a tensioning line through the guide path;

coupling a tightening mechanism to the socket, wherein an entire length of the guide path extends within the sidewall from the distal end of the socket to the tightening mechanism;

wherein the tightening mechanism is configured to control movement of the tensioning line such that the tensioning line is configured to draw the liner into the cavity of the socket and towards the distal end of the socket.

2. The method of claim 1, wherein the guide path comprises a diverter disposed at the distal end of the socket, wherein the diverter is configured to redirect the tensioning line from a first direction in which the tensioning line enters the diverter to a second direction that is substantially perpendicular to the first direction.

3. The method of claim 2, wherein the guide path further comprises a conduit coupled to the diverter, the conduit defining a duct, wherein the conduit is continuously embedded in the sidewall of the socket from the diverter to the tightening device.

4. The method of claim 1, wherein the tightening mechanism comprises an actuator configured to control movement of the tensioning line, wherein actuation of the actuator increases or decreases tension in the tensioning line.

5. The method of claim 4, wherein the tightening mechanism further comprises a housing that is configured to be selectively attached to a base and selectively removed from the base.

6. The method of claim 1, wherein the socket comprises one or more laminated layers.

7. The method of claim 1, wherein the socket comprises one or more plastic resins.

8. The method of claim 1, wherein the socket comprises one or more 3D printed structures.

9. The method of claim 1, wherein the tightening mechanism is configured to apply a tension force to the tensioning line to displace the liner downwardly into the cavity of the socket along a longitudinal axis of the socket.

10. The method of claim 1, wherein the tightening mechanism comprises a dial coupled to a spool, wherein rotation of the dial effects rotation of the spool to wind or unwind the tensioning line about the spool to increase or decrease tension in the tensioning line.

11. The method of claim 1, wherein the tightening mechanism comprises a motor to effect automated tightening or loosening of the tensioning line.

12. A method of fabricating a prosthetic socket, comprising:

forming a socket comprising a sidewall, a cavity configured to receive a liner, a distal end, a diverter, and a guide path, wherein an entire length of the guide path is disposed within the sidewall and extends proximally from the diverter disposed at the distal end of the socket;

inserting a tensioning line through the diverter and through the guide path, wherein the diverter is configured to redirect the tensioning line from a first direction in which the tensioning line enters the diverter to a second direction that is substantially perpendicular to the first direction;

coupling a tightening mechanism to the socket, wherein the guide path extends within the sidewall from the diverter to the tightening mechanism;

wherein the tightening mechanism is configured to apply a tension force to the tensioning line to displace the liner downwardly into the cavity of the socket along a longitudinal axis of the socket.

13. The method of claim 12, wherein the tightening mechanism comprises an actuator configured to control movement of the tensioning line, wherein actuation of the actuator increases or decreases tension in the tensioning line.

14. The method of claim 13, wherein the tightening mechanism further comprises a housing that is configured to be selectively attached to a base and selectively removed from the base.

15. The method of claim 12, wherein the socket comprises one or more laminated layers.

16. The method of claim 12, wherein the socket comprises one or more plastic resins.

17. The method of claim 12, wherein the socket comprises one or more 3D printed structures.

18. A method of fabricating a prosthetic socket, comprising:

forming a socket comprising a sidewall, a cavity configured to receive a liner, a distal end, and a guide path, wherein the guide path extends proximally from the distal end of the socket;

inserting a tensioning line through the guide path;

coupling a tightening mechanism to the socket, wherein the guide path extends within the sidewall from the distal end of the socket toward the tightening mechanism;

wherein the tightening mechanism is configured to control movement of the tensioning line such that the tensioning line is configured to draw the liner into the cavity of the socket and towards the distal end of the socket, the sidewall of the socket being substantially rigid so as to maintain a form of the sidewall when forces are applied during use.

19. The method of claim 18, wherein the socket comprises one or more laminated layers.

20. The method of claim 18, wherein the socket comprises one or more 3D printed structures.

* * * * *